US008338376B2

(12) United States Patent
Beckman et al.

(10) Patent No.: US 8,338,376 B2
(45) Date of Patent: Dec. 25, 2012

(54) COMPOSITIONS COMPRISING VARIANT LT-B-R-IG FUSION PROTEINS

(75) Inventors: Evan Beckman, Newton, MA (US); Graham K. Farrington, Acton, MA (US); Werner Meier, Burlington, MA (US); Jeffrey L. Browning, Brookline, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 94 days.

(21) Appl. No.: 12/560,257

(22) Filed: Sep. 15, 2009

(65) Prior Publication Data

US 2010/0111952 A1    May 6, 2010

Related U.S. Application Data

(63) Continuation of application No. PCT/US2008/003548, filed on Mar. 17, 2008, and a continuation-in-part of application No. 12/446,041, filed as application No. PCT/US2007/081761 on Oct. 18, 2007, now Pat. No. 8,067,375.

(60) Provisional application No. 60/918,518, filed on Mar. 15, 2007, provisional application No. 60/862,343, filed on Oct. 20, 2006.

(51) Int. Cl.
*A61K 38/00* (2006.01)
*A61K 38/16* (2006.01)
*A61K 45/00* (2006.01)
*C12P 21/06* (2006.01)
*C12P 21/04* (2006.01)
*C12N 15/00* (2006.01)
*C12N 5/00* (2006.01)
*C07H 21/04* (2006.01)
*C07K 1/00* (2006.01)
*C07K 14/00* (2006.01)

(52) U.S. Cl. ............... 514/16.6; 514/21.2; 424/278.1; 435/69.1; 435/69.7; 435/70.3; 435/320.1; 435/325; 536/23.4; 536/23.5; 530/350; 530/402

(58) Field of Classification Search ............... None
See application file for complete search history.

(56) References Cited

U.S. PATENT DOCUMENTS

| | | |
|---|---|---|
| 3,773,919 A | 11/1973 | Boswell et al. |
| 4,338,397 A | 7/1982 | Gilbert et al. |
| 4,485,045 A | 11/1984 | Regen |
| 4,544,545 A | 10/1985 | Ryan et al. |
| 4,758,549 A | 7/1988 | Mitsuhashi et al. |
| 4,816,567 A | 3/1989 | Cabilly et al. |
| 4,822,605 A | 4/1989 | Powell |
| 4,849,509 A | 7/1989 | Thurin et al. |
| 4,959,457 A | 9/1990 | Bringman |
| 5,082,783 A | 1/1992 | Ernst et al. |
| 5,225,538 A | 7/1993 | Capon et al. |
| 5,447,851 A | 9/1995 | Beutler et al. |
| 5,541,087 A | 7/1996 | Lo et al. |
| 5,605,690 A | 2/1997 | Jacobs et al. |
| 5,661,004 A | 8/1997 | Browning et al. |
| 5,670,149 A | 9/1997 | Browning et al. |
| 5,721,121 A | 2/1998 | Etcheverry et al. |
| 5,726,039 A | 3/1998 | Oppenheim et al. |
| 5,795,964 A | 8/1998 | Browning et al. |
| 5,856,179 A | 1/1999 | Chen et al. |
| 5,925,351 A | 7/1999 | Browning et al. |
| 5,976,833 A | 11/1999 | Furukawa et al. |
| 6,087,126 A | 7/2000 | Horwitz et al. |
| 6,312,691 B1 | 11/2001 | Browning et al. |
| 6,403,087 B1 | 6/2002 | Browning et al. |
| 6,669,941 B1 * | 12/2003 | Browning et al. ......... 424/192.1 |
| 7,001,598 B2 | 2/2006 | Browning et al. |
| 7,030,080 B2 | 4/2006 | Browning et al. |
| 7,060,667 B1 | 6/2006 | Browning et al. |
| 7,255,854 B1 * | 8/2007 | Browning et al. ........... 424/85.1 |
| 7,294,481 B1 | 11/2007 | Fung |
| 7,309,492 B2 * | 12/2007 | Browning et al. ......... 424/198.1 |
| 7,427,403 B2 | 9/2008 | Browning et al. |
| 7,452,530 B2 | 11/2008 | Browning et al. |
| 7,459,537 B2 | 12/2008 | Browning et al. |
| 7,700,317 B2 * | 4/2010 | Ambrose et al. ............. 435/69.1 |
| 7,744,891 B2 * | 6/2010 | Browning et al. ......... 424/178.1 |
| 2002/0001585 A1 | 1/2002 | Browning et al. |
| 2002/0039580 A1 | 4/2002 | Browning et al. |
| 2002/0197254 A1 | 12/2002 | Browning et al. |
| 2004/0058394 A1 | 3/2004 | Garber et al. |
| 2004/0198635 A1 | 10/2004 | Browning et al. |
| 2005/0037003 A1 | 2/2005 | Browning et al. |
| 2005/0281811 A1 | 12/2005 | Browning et al. |
| 2006/0104971 A1 | 5/2006 | Garber et al. |

(Continued)

FOREIGN PATENT DOCUMENTS

| | | |
|---|---|---|
| DE | 3218121 A1 | 11/1983 |
| EP | 0058481 B1 | 8/1982 |
| EP | 0367575 A1 | 5/1990 |
| EP | 0496973 B1 | 8/1992 |
| EP | 0509553 B1 | 10/1992 |
| EP | 0608532 A2 | 8/1994 |
| EP | 0873998 A2 | 10/1998 |
| WO | 91/00347 A1 | 1/1991 |
| WO | 92/00329 A1 | 1/1992 |
| WO | 94/04679 A1 | 3/1994 |

(Continued)

OTHER PUBLICATIONS

Phillips, A., J Pharm Pharmacology 53: 1169-1174, 2001.*
Khandke, Kiran M. et al., "Influence of ions on cyclization of the amino terminal glutamine residues of tryptic of streptococcal PepM49 protein," Int. J. Peptide Protein Res., vol. 34:118-123 (1989).

(Continued)

*Primary Examiner* — Shulamith H Shafer
(74) *Attorney, Agent, or Firm* — Nelson Mullins Riley & Scarborough LLP; Debra J. Milasincic, Esq.

(57) ABSTRACT

This invention relates to methods of treating disease with soluble inhibitors of the lymphotoxin pathway having improved properties. This invention also relates to improved LTBR-Ig fusion proteins, and pharmaceutical compositions thereof.

77 Claims, 15 Drawing Sheets

U.S. PATENT DOCUMENTS

| | | |
|---|---|---|
| 2006/0134102 A1 | 6/2006 | LePage et al. |
| 2006/0222644 A1 | 10/2006 | Garber et al. |
| 2006/0280722 A1 | 12/2006 | Browning et al. |
| 2007/0036806 A1 | 2/2007 | Glaesner et al. |
| 2007/0116668 A1 | 5/2007 | Browning et al. |
| 2007/0154476 A1 | 7/2007 | Browning et al. |
| 2008/0076155 A1 | 3/2008 | Fung |
| 2008/0219967 A1 | 9/2008 | Browning et al. |

FOREIGN PATENT DOCUMENTS

| | | |
|---|---|---|
| WO | 94/06476 A1 | 3/1994 |
| WO | 94/13808 A2 | 6/1994 |
| WO | 96/01121 A1 | 1/1996 |
| WO | 96/22788 A1 | 8/1996 |
| WO | 96/23071 A2 | 8/1996 |
| WO | 97/03678 A1 | 2/1997 |
| WO | 97/03687 A1 | 2/1997 |
| WO | 97/04658 A1 | 2/1997 |
| WO | 97/41895 A2 | 11/1997 |
| WO | 98/17313 A2 | 4/1998 |
| WO | 98/18928 A1 | 5/1998 |
| WO | 98/25967 A1 | 6/1998 |
| WO | 99/53059 A1 | 10/1999 |
| WO | 00/36092 A2 | 6/2000 |
| WO | 00/36092 A3 | 6/2000 |
| WO | 2006/007853 A2 | 1/2006 |
| WO | 2007/146414 A2 | 12/2007 |
| WO | 2008/049053 A2 | 4/2008 |

OTHER PUBLICATIONS

Plant, Sheila R. et al., "Astroglial-Derived Lymphotoxin-alpha Exacerbates Inflammation and Demyelination, But Not Remyelination," Glia, vol. 49:1-14 (2004).

Plant, Sheila R. et al., "Lymphotoxin Beta Receptor (LtBetaR):Dual Roles in Demyelination and Remyelination and Successful Therapeutic Intervention Using LtBetaR-Ig Protein," The Journal of Neuroscience, vol. 27(28):7429-7437 (2007).

International Search Report for Application No. PCT/US2008/003548, dated Nov. 11, 2009.

International Preliminary Report on Patentability for Application No. PCT/US2008/003548, dated Nov. 17, 2009.

Written Opinion for Application No. PCT/US2008/003548, dated Nov. 17, 2009.

International Search Report for Application No. PCT/US2007/081761, dated Aug. 25, 2008.

International Preliminary Report on Patentability for Application No. PCT/US2007/081761, dated Apr. 22, 2009.

Written Opinion for Application No. PCT/US2007/081761, dated Apr. 22, 2009.

Paul, Nina L. et al., "Lymphotoxin," Ann. Rev. Immunol., vol. 6:407-438 (1988).

Pennica, Diane et al., "Human tumour necrosis factor: precursor structure, expression and homology to lymphotoxin," Nature, vol. 312:724-729 (1984).

Peppel, Karsten et al., "A Tumor Necrosis Factor (TNF) Receptor-IgG Heavy Chain Chimeric Protein as a Bivalent Antagonist of TNF Activity," J. Exp. Med., vol. 171:1483-1489 (1991).

Peterson, Andrew et al., "Monoclonal antibody and ligand binding sites of the T cell erythrocyte receptor (CD2)," Nature, vol. 329:842-846 (1987).

Pfeffer, Klaus et al., "Mice Deficient for the 55 kd Tumor Necrosis Factor Receptor Are Resistant to Endotoxic Shock, yet Succumb to *L. monocytogenes* Infection," Cell, vol. 73:457-467 (1993).

Picarella, Dominic E. et al., "Insulitis in transgenic mice expressing tumor necrosis factor b (lymphotoxin) in the pancreas," Proc. Natl. Acad. Sci. USA, vol. 89:10036-10040 (1992).

Picker, Louis J. et al., "Physiological and Molecular Mechanisms of Lymphocyte Homing," Annu. Rev. Immunol., vol. 10:561-591 (1992).

Plant, S.R. et al., "Differential role of lymphotoxin in demyelination and remyelination," retrieved online at: http://www.sfn.org/abarchive/abstract.aspx2?print=on, Society for Neuroscience, Poster Presentation 213.2 (2003).

Pleskov, V.M. et al., "The receptor-mediated endocytosis of influenza viruses and low-density lipoproteins by tissue cells," Vopr. Virusol., vol. 39(3):121-125 (1994).

Pociot, F. et al., "A Tumour Necrosis Factor Beta Gene Polymorphism in Relation to Monokine Secretion and Insulin-Dependent Diabetes Mellitus," Scand. J. Immunol., vol. 33:37-49 (1991).

Ponzio, Nicholas M. et al., "Host-Tumor Interactions in the SJL Lymphoma Model," Intern. Rev. Immunol., vol. 1:273-301 (1986).

Powell, Kenneth L. et al., "The antiviral effects of nitric oxide," Trends in Microbiology, vol. 3(3):81-88 (1995).

Powrie, Fiona et al., "Inhibition of Th1 Responses Prevents Inflammatory Bowel Disease in scid Mice Reconstituted with CD45RBhi CD4+ T Cells," Immunity, vol. 1:553-562 (1994).

Powrie, Fiona et al., "Phenotypically distinct subsets of CD4+ T cells induce or protect from chronic intestinal inflammation in C. B-17 scid mice," International Immunology, vol. 5(11):1461-1471 (1993).

Qin, Zhihai et al., "Human Lymphotoxin Has at Least Equal Antitumor Activity in Comparison to Human Tumor Necrosis Factor But Is Less Toxic in Mice," Blood, vol. 85(10):2779-2785 (1995).

Queen, Cary et al., "A humanized antibody that binds to the interleukin 2 receptor," Proc. Natl. Acad. Sci. USA, vol. 86:10029-10033 (1989).

Raitano, Arthur B. et al., "Tumor Necrosis Factor Up-regulates g-Interferon Binding in a Human Carcinoma Cell Line," The Journal of Biological Chemistry, vol. 265(16):10466-10472 (1990).

Ranges, Gerald E. et al., "Tumor Necrosis Factor-a As a Proliferative Signal for an IL-2-Dependent T Cell Line: Strict Species Specificity of Action," The Journal of Immunology, vol. 142:1203-1208 (1989).

Ranges, Gerald E. et al., "Tumor Necrosis Factor a/Cachectin is a Growth Factor for Thymocytes, Synergistic Interactions with Other Cytokines," J. Exp. Med., vol. 167:1472-1478 (1988).

Reed, Steven G. et al., "T-cell and cytokine responses in leishmaniasis," Current Opinion in Immunology, vol. 5:524-531 (1993).

Reisfeld, Ralph A. et al., "Involvement of B Lymphocytes in the Growth Inhibition of Human Pulmonary Melanoma Metastases in Athymic nu/nu Mice by an Antibody-Lymphotoxin Fusion Protein," Cancer Research, vol. 56:1707-1712 (1996).

Rennert, P.D. et al., "Normal Development of Lymph Nodes is Disrupted by Soluble LT beta Receptor—Ig Fusion Protein," European Cytokine Network, vol. 7(2):167, No. 17 (1996).

Rennert, Paul D. et al., "Surface Lymphotoxin a/b Complex Is Required for the Development of Peripheral Lymphoid Organs," J. Exp. Med., vol. 184:1999-2006 (1996).

Renshaw, Blair R. et al., "Humoral Immune Response in CD40 Ligand-deficient Mice," J. Exp. Med., vol. 180:1889-1900 (1994).

Reutershealth, "Systemic Lupus Erythematosus," retrieved online at http://www.reutershealth.com/wellconnected/doc63.html (2002).

Roitt, Ivan M. et al., "Antibody Effector Functions," Immunology, Third Edition, Mosby, p. 4.8 (1993).

Roitt, Ivan M. et al., "Introduction to the Immune System," Immunology, Third Edition, Mosby, Chpt. 1, pp. 1.1-1.12 (1993).

Roitt, Ivan M. et al., "Hypersensitivity—Type I," Immunology, Third Edition, Mosby, Chpt. 19, pp. 19.1-19.22 (1993).

Romagnani, Sergio, "Lymphokine Production by Human T Cells in Disease States," Annu. Rev. Immunol., vol. 12:227-257 (1994).

Roodman, G. David et al., "Tumor Necrosis Factor-alpha and Hematopoietic Progenitors: Effects of Tumor Necrosis Factor on the Growth of Erythroid Progenitors CFU-E and BFU-E and the Hematopoietic Cell Lines K562, HL60, and HEL Cells," Exp. Hematol., vol. 15:928-935 (1987).

Rosenberg, Steven A. et al., "Use of Tumor-infiltrating Lymphocytes and Interleukin-2 in the Immunotherapy of Patients with Metastatic Melanoma," The New England Journal of Medicine, vol. 319(25):1676-1680 (1988).

Rothe, Joachim et al., "Mice lacking the tumour necrosis factor receptor 1 are resistant to TNF-mediated toxicity but highly susceptible to infection by *Listeria monocytogenes*," Nature, vol. 364:798-802 (1993).

Ruddle, Nancy H. et al., "An Antibody to Lymphotoxin and Tumor Necrosis Factor Prevents Transfer of Experimetnal Allergic Encephalomyelitis," J. Exp. Med., vol. 172:1193-1200 (1990).

Ruddle, Nancy H. et al., "Cytotoxicity Mediated by Soluble Antigen and Lymphocytes in Delayed Hypersensitivity, III. Analysis of Mechanism," The Journal of Experimental Medicine, vol. 128:1267-1279 (1968).

Ruddle, Nancy H., "Lymphotoxin redux," Immunology Today, vol. 6(5):156-159 (1985).

Ruddle, Nancy H. et al., "The Role of Lymphotoxin in Inflammation," Prog. Allergy, vol. 40:162-182 (1988).

Rudikoff, Stuart et al., "Single amino acid substitution altering antigen-binding specificity," Proc. Natl. Acad. Sci. USA, vol. 79:1979-1983 (1982).

Sanchez, Anthony et al., "Analysis of Human Peripheral Blood Samples from Fatal and Nonfatal Cases of Ebola (Sudan) Hemorrhagic Fever: Cellular Responses, Virus Load, and Nitric Oxide Levels," Journal of Virology, vol. 78 (19):10370-10377 (2004).

Sastry, K. Jagannadha et al., "HIV-1 tat Gene Induces Tumor Necrosis Factor-b (Lymphotoxin) in a Human B-lymphoblastoid Cell Line," The Journal of Biological Chemistry, vol. 265(33):20091-20093 (1990).

Sautes, Catherine et al., "Murine Soluble Fcgamma Receptors/IgG-Binding Factors (IGG-BF): Analysis of the Relation to FcgammaRII and Production of Milligram Quantities of Biologically Active Recombinant IgG-Bf," Immunol. Res., vol. 11:181-190 (1992).

Sayegh, Mohamed H. et al., "CD28-B7 Blockade after Alloantigenic Challenge In Vivo Inhibits Th1 Cytokines but Spares Th2," J. Exp. Med., vol. 181:1869-1874 (1995).

Scallon, Bernard J. et al., "Functional Comparisons of Different Tumour Necrosis Factor Receptor/IgG Fusion Proteins," Cytokine, vol. 7(8):759-770 (1995).

Schall, Thomas J. et al., "Molecular Cloning and Expression of a Receptor for Human Tumor Necrosis Factor," Cell, vol. 61:361-370 (1990).

Scheurich, Peter et al., "Immunoregulatory Activity of Recombinant Human Tumor Necrosis Factor (TNF)-a: Induction of TNF Receptors on Human T Cells and TNF-a-Mediated Enhancement of T Cell Responses," The Journal of Immunology, vol. 138(6)1786-1790 (1987).

Schiller, Joan H. et al., "Biological and Clinical Effects of Intravenous Tumor Necrosis Factor-a Administered Three Times Weekly," Cancer Research, vol. 51:1651-1658 (1991).

Schoenfeld, Hans-Joachim et al., "Efficient Purification of Recombinant Human Tumor Necrosis Factor b from *Escherichia coli* Yields Biologically Active Protein with a Trimeric Structure That Binds to Both Tumor Necrosis Factor Receptors," The Journal of Biological Chemistry, vol. 266(6):3863-3869 (1991).

Schriever, Folke et al., "The Central Role of Follicular Dendritic Cells in Lymphoid Tissues," Advances in Immunology, vol. 51:243-284 (1992).

Scott, Daryl A. et al., "The Pendred syndrome gene encodes a chloride-iodide transport system," Nature Genetics, vol. 21:440-443 (1999).

Séité, Paule et al., "BCL2 Gene Activation and Protein Expression in Follicular Lymphoma: a Report on 64 Cases," Leukemia, vol. 7(3):410-417 (1993).

Selmaj, Krzysztof et al., "Identification of Lymphotoxin and Tumor Necrosis Factor in Multiple Sclerosis Lesions," J. Clin. Invest., vol. 87:949-954 (1991).

Zhou, M. et al., "Real-Time Measurements of Kinetics of EGF Binding to Soluble EGF Receptor Monomers and Dimers Support the Dimerization Model for Receptor Activation," Biochemistry, vol. 32:8193-8198 (1993).

Ziff, Morris, "Emigration of Lymphocytes in Rheumatoid Synovitis," Advances in Inflammation Research, vol. 12:1-9 (1988).

International Search Report for Application No. PCT/US2008/003548, 8 pages, dated Nov. 11, 2009.

International Preliminary Report on Patentability and Written Opinion for Application No. PCT/US2008/003548, 10 pages, dated Nov. 17, 2009.

European Office Action for Application No. 08742126.9, 5 pages, dated Aug. 22, 2011.

European Office Action for Application No. 08742126.9, 5 pages, dated May 18, 2012.

Rudikoff, Stuart et al., "Functional antibody lacking a variable-region disulfide bridge," Proc. Natl. Acad. Sci. USA, vol. 83:7875-7878 (1986).

Rennert, Paul D. et al., "Selective disruptoin of lymphotoxin ligands reveals a novel set of mucosal lymph nodes and unique effects on lymph node cellular organization," International Immunology, vol. 9(11):1627-1639 (1997).

Reuveny, S. et al., "Effect of temparature and oxygen on cell growth and recombinant protein production in insect cell culture," Appl. Microbiol. Biotechnol., vol. 38:619-623 (1993).

Shalaby, M. Rafaat et al., "The Involvement of Human Tumor Necrosis Factors-a and -b in the Mixed Lymphocyte Reaction," The Journal of Immunology, vol. 141(2):499-503 (1988).

Sheehan, Kathleen C.F. et al., "Generation and Characterization of Hamster Monoclonal Antibodies that Neutralize Murine Tumor Necrosis Factors," The Journal of Immunology, vol. 142(11):3884-3893 (1989).

Shehadeh, Naim N. et al., "Altered Cytokine Activity in Adjuvant Inhibition of Autoimmune Diabetes," Journal of Autoimmunity, vol. 6:291-300 (1993).

Sidman, Kenneth R. et al., "Controlled Release of Macromolecules and Pharmaceuticals from Synthetic Polypeptides Based on Glutamic Acid," Biopolymers, vol. 22:547-556 (1983).

Sigel, Morton B. et al., "Production of Antibodies by Inoculation into Lymph Nodes," Methods in Enzymology, vol. 93:3-12 (1983).

Simonet, W.S. et al., "Osteoprotegerin: A Novel Secreted Protein Involved in the Regulation of Bone Density," Cell, vol. 89:309-319 (1997).

Slepushkin, A.N. et al., "A comparative study of live and inactivated influenza vaccines: the organization of the observation and the results of a study of their reactogenicity and immunogenicity," Vopr. Virusol., vol. 39(3):128-131 (1994).

Smith, Craig A. et al., "A Receptor for Tumor Necrosis Factor Defines an Unusual Family of Cellular and Viral Proteins," Science, vol. 248:1019-1023 (1990).

Smith, Craig A. et al., "CD30 Antigen, a Marker for Hodgkin's Lymphoma, Is a Receptor Whose Ligand Defines an Emerging Family of Cytokines with Homology to TNF," Cell, vol. 73:1349-1360 (1993).

Smith, Craig A. et al., "The TNF Receptor Superfamily of Cellular and Viral Proteins: Activation, Costimulation, and Death," Cell, vol. 76(6):959-962 (1994).

Spriggs, David R. et al., "Tumor Necrosis Factor Expression in Human Epithelial Tumor Cell Lines," J. Clin. Invest., vol. 81:455-460 (1988).

Stevenson, George T. et al., "Conjugation of Human Fcgamma in Closed-Hinge or Open-Hinge Configuration to Fab'gamma and Analogous Ligands," The Journal of Immunology, vol. 158:2242-2250 (1997).

Suda, Takashi et al., "Molecular Cloning and Expression of the Fas Ligand, a Novel Member of the Tumor Necrosis Factor Family," Cell, vol. 75:1169-1178 (1993).

Sureshkumar, G.K. et al., "The Influence of Temperature on the Mouse-Mouse Hybridoma Growth and Monoclonal Antibody Production," Biotechnology and Bioengineering, vol. 37:292-295 (1991).

Tartaglia, Louis A. et al., "Two TNF receptors," Immunology Today, vol. 13(5):151-153 (1992).

Tavernier, Jan et al., "Conserved residues of tumour necrosis factor and lymphotoxin constitute the framework of the trimeric structure," FEBS, vol. 257(2):315-318 (1989).

Tew, John G. et al., "Follicular Dendritic Cells as Accessory Cells," Immunological Reviews, vol. 117:185-211 (1990).

Thomas, H. et al., "Biological Approaches to Cancer Therapy," The Journal of International Medical Research, vol. 17:191-204 (1989).

Tibbetts, Randal S. et al., "Cardiac Antigen-Specific Autoantibody Production is Associated with Cardiomyopathy in *Trypanosoma cruzi*-infected mice," Journal of Immunology, vol. 152:1493-1499 (1994).

Toellner, Kai-Michael et al., "Immunoglobulin Swith Transcript Production In Vivo Related to the Site and Time of Antigen-specific B Cell Activation," J. Exp. Med., vol. 183:2303-2312 (1996).

Traunecker, André et al., "Highly efficient neutralization of HIV with recombinant CD4-immunoglobulin molecules," Nature, vol. 339:68-70 (1989).

Trethewey, Pat, "Systemic Lupus Erythematosus," Dimensions of Critical Care Nursing, vol. 23(3):111-115 (2004).

Trueb, Ralph et al., "Expression of an Adenovirally Encoded Lymphotoxin-beta Inhibitor Prevents Clearance of Listeria monocytogenes in Mice," Journal of Inflammation, vol. 45:239-247 (1995).

Tschachler, Erwin et al., "Constitutive Expression of Lymphotoxin (Tumor Necrosis Factor b) in HTLV-I-Infected Cell Lines," Human Retrovirology HTLV, Raven Press, Ltd., William A. Blattner (Ed.), pp. 105-113 (1990).

Tsiagbe, V.K. et al., "Syngeneic Response to SJL Follicular Center B Cell Lymphoma (Reticular Cell Sarcoma) Cells Is Primarily in Vb16+ CD4+ T Cells," The Journal of Immunology, vol. 150:5519-5528 (1993).

Tsiagbe, V.K. et al., "The Physiology of Germinal Centers," Critical Reviews in Immunology, vol. 16:381-421 (1996).

Turner, Martin et al., "Human T cells from autoimmune and normal individuals can produce tumor necrosis factor," Eur. J. Immunol., vol. 17:1807-1814 (1987).

Ullrich, Axel et al., "Signal Transduction by Receptors with Tyrosine Kinase Activity," Cell, vol. 61:203-212 (1990).

Van Dullemen, Hendrik M. et al., "Treatment of Crohn's Disease With Anti-Tumor Necrosis Factor Chimeric Monoclonal Antibody (cA2)," Gastroenterology, vol. 109:129-135 (1995).

Van Kooten, Cees et al., "CD40-CD40 Ligand: A Multifunctional Receptor—Ligand Pair," Advances in Immunology, vol. 61:1-77 (1996).

Van Vliet, Els et al., "Reticular Fibroblasts in Peripheral Lymphoid Organs Identified by a Monoclonal Antibody," The Journal of Histochemistry and Cytochemistry, vol. 34(7):883-890 (1986).

Ware, Carl F. et al., "Expression of Surface Lymphotoxin and Tumor Necrosis Factor on Activated T, B, and Natural Killer Cells," The Journal of Immunology, vol. 149(12):3881-3888 (1992).

Ware, Carl F. et al., "Human T Cell Hybridomas Producing Cytotoxic Lymphokines: Induction of Lymphotoxin Release and Killer Cell Activity by Anti-CD3 Monoclonal Antibody or Lectins and Phorbol Ester," Lymphokine Research, vol. 5 (4):313-324 (1986).

Ware, Carl F. et al., "Mechanisms of Lymphocyte-mediated Cytotoxicity II. Biochemical and Serologic Identification of a Precursor Lymphotoxin Form (pre-LT) Produced by MLC-Sensitized Human T Lymphocytes in Vitro," The Journal of Immunology, vol. 126(5):1927-1933 (1981).

Ware, Carl F. et al., "Regulation of the CTL Lytic Pathway by Tumor Necrosis Factor," Cellular Immunity and the Immunotherapy of Cancer, pp. 121-128 (1990).

Ware, C.F. et al., "The Ligands and Receptors of the Lymphotoxin System," Curr. Top. Microbiol. Immunol., vol. 198:175-218 (1995).

Warfield, Kelly L. et al., "Induction of Humoral and CD8+ T Cell Responses Are Required for Protection against Lethal Ebola Virus Infection," The Journal of Immunology, vol. 175:1184-1191 (2005).

Warzocha, Krzysztof et al., "Mechanisms of action of the tumor necrosis factor and lymphotoxin ligand-receptor system," Eur. Cytokine Netw., vol. 5(6):83-96 (1994).

Watanabe-Fukunaga, Rie et al., "Lymphoproliferation disorder in mice explained by defects in Fas antigen that mediates apoptosis," Nature, vol. 356:314-317 (1992).

Weickert, Michael J. et al., "Stabilization of Apoglobin by Low Temperature Increases Yield of Soluble Recombinant Hemoglobin in *Escherichia coli*," Applied and Environmental Microbiology, vol. 63(11):4313-4320 (1997).

Weidemann, Ralph et al., "Low temperature cultivation—A step towards process optimisation," Cytotechnology, vol. 15:111-126 (1997).

Williams, Richard O. et al., "Successful therapy of collagen-induced arthritis with TNF receptor-IgG fusion protein and combination with anti-CD4," Immunology, vol. 84:433-439 (1995).

Winter, Greg et al., "Man-made antibodies," Nature, vol. 349:293-299 (1991).

Wong, G.H.W. et al., "Strategies for Manipulating Apoptosis for Cancer Therapy With Tumor Necrosis Factor and Lymphotoxin," Journal of Cellular Biochemistry, vol. 60:56-60 (1996).

Wong, Grace H.W. et al., "Tumour necrosis factor a and b inhibit virus replication and synergize with interferons," Nature, vol. 323:819-822 (1986).

Wu, Qiang et al., "The Requirement of Membrane Lymphotoxin for the Presence of Dendritic Cells in Lymphoid Tissues," J. Exp. Med., vol. 190(5):629-638 (1999).

Wysocki, L.J. et al., "'Panning' for lymphocytes: A method for cell selection," Proc. Natl. Acad. Sci. USA, vol. 75 (6):2844-2848 (1978).

Xu, Jianchao et al., "Mice Deficient for teh CD40 Ligand," Immunity, vol. 1:423-431 (1994).

Yonehara, Shin et al., "A Cell-killing monoclonal antibody (Anti-Fas) to a Cell Surface Antigen Co-downregulated with the Receptor of Tumor Necrosis Factor," J. Exp. Med., vol. 169:1747-1756 (1989).

Zhai, Yifan et al., "Light, a Novel Ligand for Lymphotoxin beta Receptor and TR2/HVEM Induces Apoptosis and Suppresses in Vivo Tumor Formation Via Gene Transfer," J. Clin. Invest., vol. 102(6):1142-1151 (1998).

Cher, Daniel J. et al., "Two Types of Murine Helper T Cell Clone, II. Delayed-Type Hypersensitivity is Mediated by TH1 Clones," The Journal of Immunology, vol. 138(11):3688-3694 (1987).

Chicheportiche, Yves et al., "TWEAK, a New Secreted Ligand in the Tumor Necrosis Factor Family That Weakly Induces Apoptosis," The Journal of Biological Chemistry, vol. 272(51):32401-32410 (1997).

Chisholm, Patricia L. et al., "Monoclonal antibodies to the integrin a-4 subunit inhibit the murine contact hypersensitivity response," Eur. J. Immunol., vol. 23:682-688 (1993).

Chuppa, Sandra et al., "Fermentor Temperature as a Tool for Control of High-Density Perfusion Cultures of Mammalian Cells," Biotechnol. Bioeng., vol. 55:328-338 (1997).

Corcoran, Anne E. et al., "Characterization of ligand binding by the human p55 tumour-necrosis-factor receptor, Involvement of individual cysteine-rich repeats," Eur. J. Biochem., vol. 223:831-840 (1994).

Corcoran, A.E. et al., "Minimal tumor necrosis factor receptor binding protein: optimum biological activity of a truncated p55 soluble tumor necrosis factor receptor-IgG fusion protein," European Cytokine Network, vol. 9 (3):255-262 (1998).

Cotran, Ramzi S. et al., "Endothelial Activation, Its Role in Inflammatory and Immune Reactions," Endothelial Cell Biology in Health and Disease, Chpt. 15, pp. 335-347 (1988).

Crowe, Paul D. et al., "A Lymphotoxin-b-Specific Receptor," Science, vol. 264:707-708 (1994).

Crowe, Paul D. et al., "Production of lymphotoxin (LTa) and a soluble dimeric form of its receptor using the baculovirus expression system," Journal of Immunological Methods, vol. 168:79-89 (1994).

Damle, Nitin K. et al., "Distinct Regulatory Effects of IL-4 and TNF-a During CD3-Dependent and CD3-Independent Initiation of Human T-Cell Activation," Lymphokine Research, vol. 8(2):85-97 (1989).

Degli-Esposti, Mariapia A. et al., "Activation of the Lymphotoxin b Receptor by Cross-Linking Induces Chemokine Production and Growth Arrest in A375 Melanoma Cells," The Journal of Immunology, vol. 158:1756-1762 (1997).

Dermer, Gerald B., "Another Anniversary for the War on Cancer," BioTechnology, vol. 12:320 (1994).

De Togni, Pietro et al., "Abnormal Development of Peripheral Lymphoid Organs in Mice Deficient in Lymphotoxin," Science, vol. 264:703-707 (1994).

Dhein, Jens et al., "Induction of Apoptosis by Monoclonal Antibody Anti-APO-1 Class Switch Variants is Dependent on Cross-linking of APO-1 Cell Surface Antigens," The Journal of Immunology, vol. 149(10):3166-3173 (1992).

Dighe, Anand S. et al., "Enhanced in Vivo Growth and Resistance to Rejection of Tumor Cells Expressing Dominant Negative IFNg Receptors," Immunity, vol. 1:447-456 (1994).

Dijkstra, Christine D. et al., "Marginal zone macrophages identified by a monoclonal antibody: characterization of immuno- and enzyme-histochemical properties and functional capacities," Immunology, vol. 55:23-30 (1985).

Doumbou, Cyr Lézin et al., "Selection and Characterization of Microorganisms Utilizing THaxtomin A, a Phytotoxin Produced by Streptomyces scabies," Applied and Environmental Microbiology, vol. 64(11):4313-4316 (1998).

Düzgünes, Nejat et al., "Liposome Targeting to HIV-Infected Cells Via Recombinant Soluble CD4 and CD4-IgG (Immunoadhesin)," Journal of Cellular Biochemistry, vol. 16:77, No. Q514 (1992).

Eason, James D. et al., "Evaluation of Recombinant Human Soluble Dimeric Tumor Necrosis Factor Receptor for Prevention of OKT3-Associated Acute Clinical Syndrome," Transplantation, vol. 61(2):224-228 (1996).

Eck, Michael J. et al., "The Structure of Tumor Necrosis Factor-a at 2.6 Å Resolution, Implications for Receptor Binding," The Journal of Biological Chemistry, vol. 264(29):17595-17605 (1989).

Eck, Michael J. et al., "The Structure of Human Lymphotoxin (Tumor Necrosis Factor-b) at 1.9-Å Resolution," The Journal of Biological Chemistry, vol. 267(4):2119-2122 (1992).

Eggermont, Alexander M.M. et al., "Isolated Limb Perfusion With High-Dose Tumor Necrosis Factor-a in Combination With Interferon-g and Melphalan for Nonresectable Extremity Soft Tissue Sarcomas: A Multicenter Trial," Journal of Clinical Oncology, vol. 14(10):2653-2665 (1996).

Endres, Robert et al., "Mature Follicular Dendritic Cell Networks Depend on Expression of Lymphotoxin b Receptor by Radioresistant Stromal Cells and of Lymphotoxin b and Tumor Necrosis Factor by B Cells," J. Exp. Med., vol. 189 (1):159-167 (1999).

Eppstein, Deborah A. et al., "Biological activity of liposome-encapsulated murine interferon g is mediated by a cell membrane receptor," Proc. Natl. Acad. Sci. USA, vol. 82:3688-3692 (1985).

Erickson, Sharon L. et al., "Decreased sensitivity to tumour-necrosis factor but normal T-cell development in TNF receptor-2-deficient mice," Nature, vol. 372:560-563 (1994).

Ettinger, Rachel et al., "Disrupted splenic architecture, but normal lymph node development in mice expressing a soluble lymphotoxin-b receptor-IgG1 fusion protein," Proc. Natl. Acad. Sci. USA, vol. 93:13102-13107 (1996).

Fägerstam, Lars G. et al., "Surface Plasmon Resonance Detection in Affinity Technologies," Handbook of Affinity Chromatography, Chpt. 9, pp. 229-252 (1993).

Fanslow, William C. et al., "Soluble Forms of CD40 Inhibit Biologic Responses of Human B Cells," The Journal of Immunology, vol. 149(2):655-660 (1992).

Farrah, Terry et al., "Emerging cytokine family," Nature, vol. 358:26 (1992).

Feldmann, Marc et al., "Anti-Tumor Necrosis Factor-a Therapy of Rheumatoid Arthritis," Advances in Immunology, vol. 64:283-350 (1997).

Fitch, F.W. et al., "Differential Regulation of Murine T Lymphocyte Subsets," Annu. Rev. Immunol., vol. 11:29-48 (1993).

Flier, Jeffrey S. et al., "The Tumor Necrosis Factor Ligand and Receptor Families," Seminars in Medicine of the Beth Israel Hospital, Boston, vol. 334(26)1717-1725 (1996).

Force, Walker R. et al., "Mouse Lymphotoxin-b Receptor," The Journal of Immunology, vol. 155:5280-5288 (1995).

Forster, Simon J. et al., "Expression of Foreign Genes in Mammalian Cells Using an Antibody Fusion System," Molecular Biotechnology, vol. 1:251-263 (1994).

Foy, Teresa M. et al., "gp39-CD40 Interactions Are Essential for Germinal Center Formation and the Development of B Cell Memory," J. Exp. Med., vol. 180:157-163 (1994).

Freshney, R. Ian et al., Culture of Animal Cells, A Manual of Basic Technique, Second Edition, Alan R. Liss, Inc., New York, Chpt. 1, p. 4 (1987).

Fu, Yang-Xin et al., "B Lymphocytes Induce the Formation of Follicular Dendritic Cell Clusters in a Lymphotoxin a-dependent Fashion," J. Exp. Med., vol. 187(7):1009-1018 (1998).

Fu, Yang-Xin et al., "Development and Maturation of Secondary Lymphoid Tissues," Annu. Rev. Immunol., vol. 17:399-433 (1999).

Fu, Yang-Xin et al., "Lymphotoxin-a (LTa) Supports Development of Splenic Follicular Structure That Is Required for IgG Responses," J. Exp. Med., vol. 185(12):2111-2120 (1997).

Fuh, Germaine et al., "Rational Design of Potent Antagonists to the Human Growth Hormone Receptor," Science, vol. 256:1677-1680 (1992).

Fukushima, Keiko et al., "N-Linked Sugar Chain Structure of Recombinant Human Lymphotoxin Produced by CHO Cells: The Functional Role of Carbohydrate as to Its Lectin-like Character and Clearance Velocity," Archives of Biochemistry and Biophysics, vol. 304(1):144-153 (1993).

Furukawa, Kazuaki et al., "Effect of culture temperature on a recombinant CHO cell line producing a C-terminal a-amidating enzyme," Cytotechnology, vol. 26:153-164 (1998).

Fütterer, Agnes et al., "The Lymphotoxin b Receptor Controls Organogenesis and Affinity Maturation in Peripheral Lymphoid Tissues," Immunity, vol. 9:59-70 (1998).

Gatanaga, Tetsuya et al., "Purification and characterization of an inhibitor (soluble tumor necrosis factor receptor) for tumor necrosis factor and lymphotoxin obtained from the serum ultrafiltrates of human cancer patients," Proc. Natl. Acad. Sci. USA, vol. 87:8781-8784 (1990).

Giard, Donald J. et al., "Effect of Temperature on the Production of Human Fibroblast Interferon (41411)," Proceedings of the Society for Experimental Biology and Medicine, vol. 170:155-159 (1982).

Goeddel, D.V. et al., "Tumor Necrosis Factors: Gene Structure and Biological Activities," Cold Spring Harbor Symposia Quantitative Biology, vol. LI:597-609 (1986).

Gommerman, Jennifer L. et al., "A role for surface lymphotoxin in experimental autoimmune encephalomyelitis independent of Light," Journal of Clinical Investigation, vol. 112(5):755-767 (2003).

Gommerman, Jennifer L. et al., "Lymphotoxin/Light, Lymphoid Microenvironments and Autoimmune Disease," Nat. Rev. Immunol., vol. 3(8):642-655 (2003).

Gonzalez, Mercedes et al., "The Sequential Role of Lymphotoxin and B Cells in the Development of Splenic Follicles," J. Exp. Med., vol. 187(7):997-1007 (1998).

Goodwin, Raymond G. et al., "Molecular and Biological Characterization of a Ligand for CD27 Defines a New Family of Cytokines with Homology to Tumor Necrosis Factor," Cell, vol. 73:447-456 (1993).

Granger, Gale A. et al., "Lymphocyte in Vitro Cytotoxicity: Mechanisms of Immune and Non-Immune Small Lymphocyte Mediated Target L Cell Destruction," The Journal of Immunology, vol. 101(1):111-120 (1968).

Gray, Patrick W. et al., "Cloning and expression of cDNA for human lymphotoxin, a lymphokine with tumour necrosis activity," Nature, vol. 312:721-724 (1984).

Gray, Patrick W., "Molecular Characterization of Human Lymphotoxin," Lymphokines, vol. 13:199-208 (1987).

Green, Douglas R. et al., "Fas-ligand: Privilege and peril," Proc. Natl. Acad. Sci. USA, vol. 94:5986-5990 (1997).

Green, Lora M. et al., "Cytotoxic Lymphokines Produced by Cloned Human Cytotoxic T Lymphocytes, I. Cytotoxins Produced by Antigen-Specific and Natural Killer-Like CTL Are Dissimilar to Classical Lymphotoxins," The Journal of Immunology, vol. 135(6):4034-4043 (1985).

Green, Lora M. et al., "Rapid Colormetric Assay for Cell Viability: Application to the Quantitation of Cytotoxic and Growth Inhibitory Lymphokines," Journal of Immunological Methods, vol. 70:257-268 (1984).

Gupta, Manisha et al., "CD8-Mediated Protection against Evola Virus Infection Is Perforin Dependent," The Journal of Immunology, vol. 174:4198-4202 (2005).

Györfy, Z. et al., "Alteration of the TNF Sensitivity and Membrane Viscosity of Target Cells," Eur. Cytokine Netw., vol. 7(2):167 (1996).

Hagemeijer, A., "Cytogenics and oncogenes," Leukemia, vol. 6(Suppl. 4):16-18 (1992).

Han, Shuhua et al., "Cellular Interaction in Germinal Centers, Roles of CD40 Ligand and B7-2 in Established Germinal Centers," The Journal of Immunology, vol. 155:556-567 (1995).

Harris, William J. et al., "Therapeutic antibodies—the coming of age," TibTech, vol. 11:42-44 (1993).

Harrop, Jeremy A. et al., "Herpesvirus Entry Mediator Ligand (HVEM-L), a Novel Ligand for HVEM/TR2, Stimulates Proliferation of T Cells and Inhibits HT29 Cell Growth," The Journal of Biological Chemistry, vol. 273(42):27548-27556 (1998).

Havell, Edward A. et al., "The Antitumor Function of Tumor Necrosis Factor (TNF) I. Therapeutic Action of TNF against an Established Murine Sarcoma Is Indirect, Immunologically Dependent, and Limited by Severe Toxicity," J. Exp. Med., vol. 167:1067-1085 (1988).

Heath, Sonya L. et al., "Follicular dendritic cells and human immunodeficiency virus infectivity," Nature, vol. 377:740-744 (1995).

Higuchi, Masahiro et al., "Inhibition of Ligand Binding and Antiproliferative Effects of Tumor Necrosis Factor and Lymphotoxin by Soluble Forms of Recombinant P60 and P80 Receptors," Biochemical and Biophysical Research Communications, vol. 182(2):638-643 (1992).

Hipp, Jason D. et al., "Cancer Vaccines: An Update," In Vivo, vol. 14:571-585 (2000).

Hiserodt, John C. et al., "Identification of Membrane-Associated Lymphotoxin (LT) on Mitogen-Activated Human Lymphocytes Using Heterologous Anti-LT Antisera in Vitro," Cellular Immunology, vol. 34:326-339 (1977).

Hober, Didier et al., "Serum Levels of Tumor Necrosis Factor-a (TNF-a), Interleukin-6 (IL-6), and Interleukin-1b (IL-1b) in Dengue-Infected Patients," Am. J. Trop. Med. Hyg., vol. 48(3):324-331 (1993).

Huang, Sui et al., "Immune Response in Mice That Lack the Interferon-g Receptor," Science, vol. 259:1742-1745 (1993).

Hudde, T. et al., "Activated polyamidoamine dendrimers, a non-viral vector for gene trasfer to the corneal endothelium," Gene Therapy, vol. 6:939-943 (1999).

Hwang, Karl J. et al., "Hepatic uptake and degradation of unilamellar sphingomyelin/cholesterol liposomes: A kinetic study," Proc. Natl. Acad. Sci. USA, vol. 77(7):4030-4034 (1980).

Invitrogen life technologies, "BaculoDirect™ Baculovirus Expression Systems," Instruction Manual, Version F (2004).

Itoh, Naoto et al., "The Polypeptide Encoded by the cDNA for Human Cell Surface Antigen Fas Can Mediate Apoptosis," Cell, vol. 66:233-243 (1991).

Jain, Rakesh K., "Vascular and interstitial barriers to delivery of therapeutic agents in tumors," Cancer and Metastasis Reviews, vol. 9:753-766 (1990).

Jalkanen, S. et al., "A Distinct Endothelial Cell Recognition System That Controls Lymphocyte Traffic into Inflamed Synovium," Science, vol. 233:556-558 (1986).

Jenkins, Nitel et al., "Temperature Control of Growth and Productivity in Mutant Chinese Hamster Ovary Cells Synthesizing a Recombinant Protein," Biotechnology and Bioengineering, vol. 42:1029-1036 (1993).

Johne, Berit et al., "Epitope mapping and binding kinetics of monoclonal antibodies studied by real time biospecific interaction analysis using surface plasmon resonance," Journal of Immunological Methods, vol. 160:191-198 (1993).

Jones, E.Y. et al., "Structure of tumour necrosis factor," Nature, vol. 338:225-228 (1989).

Juráková, Vera et al., "Interferon inducer, polyriboguanylic—polyribocytidylic acid, inhibits experimental hepatic metastases in mice," European Journal of Pharmacology, vol. 221:107-111 (1992).

Kasid, Attan et al., "Human gene transfer: Characterization of human tumor-infiltrating lymphocytes as vehicles for retroviral-mediated gene trasfer in man," Proc. Natl. Acad. Sci. USA, vol. 87:473-477 (1990).

Katz, Irene R. et al., "Growth of SJL/J-Derived Transplantable Reticulum Cell Sarcoma as Related to Its Ability to Induce T-Cell Proliferation in the Host. III. Studies on Thymectomized and Congenitally Athymic SJL Mice," Cellular Immunology, vol. 65:84-92 (1981).

Katz, Jonathan D. et al., "T Helper Cell Subsets in Insulin-Dependent Diabetes," Science, vol. 268:1185-1188 (1995).

Kaufmann, Hitto et al., "Influence of Low Temperature on Productivity, Proteome and Protein Phosphorylation of CHO Cells," Biotechnol. Bioeng., vol. 63:573-582 (1999).

Kawabe, Tsutomu et al., "The Immune Responses in CD40-Deficient Mice: Impaired Immunoglobulin Class Switching and Germinal Center Formation," Immunity, vol. 1:167-178 (1994).

Khandke, Kiran M. et al., "Influence of ions on cyclization of the amino terminal glutamine residues of tryptic peptides of streptococcal PepM49 protein," Int. J. Peptide Protein Res., vol. 34:118-123 (1989).

Kinkhabwala, M. et al., "A Novel Addition to the T Cell Repertory Cell Surface Expression of Tumor Necrosis Factor/Cachectin by Activated Normal Human T Cells," J. Exp. Med., vol. 171:941-946 (1990).

Kohno, Tadahiko et al., "A second tumor necrosis factor receptor gene product can shed a naturally occurring tumor necrosis factor inhibitor," Proc. Natl. Acad. Sci. USA, vol. 87:8331-8335 (1990).

Kolanus, Waldemar et al., "T Cell Activation by Clustered Tyrosine Kinases," Cell, vol. 74:171-183 (1993).

Kopp, William C. et al., "Immunomodulatory Effects of Interferon-g in Patients with Metastatic Malignant Melanoma," J. Immunother, vol. 13(3):181-190 (1993).

Kraal, Georg, "Cells in the Marginal Zone of the Spleen," International Review of Cytology, vol. 132:31-74 (1992).

Kraal, Georg et al., "Expression of the Mucosal Vascular Addressin, MAdCAM-1, on Sinus-Lining Cells in the Spleen," American Journal of Pathology, vol. 147(3):763-771 (1995).

Kraal, G. et al., "Lymphocyte migration in the spleen: the effect of macrophage elimination," Immunology, vol. 68:227-232 (1989).

Kraal, G. et al., "Marginal metallophilic cells of the mouse spleen identified by a monoclonal antibody," Immunology, vol. 58:665-669 (1986).

Kratz, Alexander et al., "Chronic Inflammation Caused by Lymphotoxin Is Lymphoid Neogenesis," J. Exp. Med., vol. 183:1461-1472 (1996).

Kriegler, M. et al., "A Novel Form of TNF/Cachectin Is a Cell Surface Cytotoxic Transmembrane Protein: Ramifications for the Complex Physiology of TNF," Cell, vol. 53:45-53 (1988).

Kwon, Byoung S. et al., "A Newly Identified Member of the Tumor Necrosis Factor Receptor Superfamily with a Wide Tissue Distribution and Involvement in Lymphocyte Activation," The Journal of Biological Chemistry, vol. 272 (22):14272-14276 (1997).

Lacy, Mark D. et al., "Viral Hemorrhagic Fevers," Advances in Pediatric Infectious Diseases, vol. 12:21-53 (1997).

Laman, Jon D. et al., "Functions of CD40 and Its Ligand, gp39 (CD40L)," Critical Reviews in Immunology, vol. 16:59-108 (1996).

Lane, Peter et al., "Activated human T cells express a ligand for the human B cell-associated antigen CD40 which participates in T cell-dependent activation of B lymphocytes," Eur. J. Immunol., vol. 22:2573-2578 (1992).

Langer, Robert et al., "Biocompatibility of polymeric delivery systems for macromolecules," Journal of Biomedical Materials Research, vol. 15:267-277 (1981).

Langer, Robert, "Controlled release of macromolecules," Chemtech, pp. 98-105 (1982).

Lasky, J.L. et al., "Characterization and Growth Factor Requirements of SJL Lymphoma, I. Development of a B Cell Growth Factor-Dependent in Vitro Cell Line, cRCS-X," The Journal of Immunology, vol. 14:679-687 (1988).

Lasky, Jennifer L. et al., "Characterization and growth factor requirements of SJL lymphomas II. Interleukin 5 dependence on the in vitro cell line, cRCS-X, and influence of other cytokines," Eur. J. Immunol., vol. 19:365-371 (1989).

Lawton, Pornsri et al., "Characterization of the Mouse Lymphotoxin-b Gene," The Journal of Immunology, vol. 154:239-246 (1995).

Lazar, Eliane et al., "Transforming Growth Factor a: Mutation of Aspartic Acid 47 and Leucine 48 Results in Different Biological Activities," Molecular and Cellular Biology, vol. 8(3):1247-1252 (1988).

Le Hir, Michel et al., "Differentiation of Follicular Dendritic Cells and Full Antibody Responses Require Tumor Necrosis Factor Receptor-1 Signaling," J. Exp. Med., vol. 183:2367-2372 (1996).

Lee, Won-Ha et al., "Tumor Necrosis Factor Receptor Superfamily 14 Is Involved in Atherogenesis by Inducing Proinflammatory Cytokines and Matrix Metalloproteinases," Arterioscler. Thromb. Vasc. Biol., vol. 21:2004-2010 (2001).

Lin, Xiaoqi et al., "Membrane lymphotoxin is required for resistance to Theiler's virus infection," International Immunology, vol. 15(8):955-962 (2003).

Luettig, Birgit et al., "Evidence for the Existence of Two Forms of Membrane Tumor Necrosis Factor: An Integral Protein and a Molecule Attached to its Receptor," The Journal of Immunology, vol. 143(12):4034-4038 (1989).

Liang, Chi-Ming et al., "Production and Characterization of Monoclonal Antibodies Against Recombinant Human Tumor Necrosis Factor/Cachectin," Biochemical and Biophysical Research Communications, vol. 137(2):847-854 (1986).

Ling, Leona E. et al., "Human Type I Interferon Receptor, IFNAR, Is a Heavily Glycosylated 120-130 kD Membrane Protein," Journal of Interferon and Cytokine Research, vol. 15:55-61 (1995).

Liu, Chau-Ching et al., "Identification and characterization of a membrane-bound cytotoxin of murine cytolytic lymphocytes that is related to tumor necrosis factor/cachectin," Proc Natl. Acad. Sci. USA, vol. 86:3286-3290 (1989).

Liu, Chau-Ching et al., "Identification, Isolation, and Characterization of a Novel Cytotoxin in Murine Cytolytic Lymphocytes," Cell, vol. 51:393-403 (1987).

Loetscher, Hansruedi et al., "Recombinant 55-kDa Tumor Necrosis Factor (TNF) Receptor," The Journal of Biological Chemistry, vol. 266(27):18324-18329 (1991).

Ludwig, Andreas et al., "Influence of the temperature on the shear stress sensitivity of adherent BHK 21 cells," Appl. Microbiol. Biotechnol., vol. 38:323-327 (1992).

MacKay, Fabienne et al., "Both the Lymphotoxin and Tumor Necrosis Factor Pathways Are Involved in Experimental Murine Models of Colitis," Gastroenterology, vol. 115:1464-1475 (1998).

MacKay, Fabienne et al., "Cytotoxic Activities of Recombinant Soluble Murine Lymphotoxin-a and Lymphotoxin-ab Complexes," The Journal of Immunology, vol. 159:3299-3310 (1997).

MacKay, Fabienne et al., "Lymphotoxin but not tumor necrosis factor functions to maintain splenic architecture and humoral responsiveness in adult mice," Eur. J. Immunol., vol. 27:2033-2042 (1997).

MacKay, Fabienne et al., "Turning off follicular dendritic cells," Nature, vol. 395:26-27 (1998).

MacLennan, I.C.M. et al., "The Structure and Function of Secondary Lymphoid Tissues," Clinical Aspects of Immunology, Blackwell Scientific Publications, 5th Edition, vol. 1, Chpt. 2, pp. 13-30 (1993).

Maeda, Kunihiko et al., "Murine Follicular Dendritic Cells and Low Affinity Fc Receptors for IgE (FceRII)," The Journal of Immunology, vol. 148(8):2340-2347 (1992).

Mallett, Susan et al., "A new superfamily of cell surface proteins related to the nerve growth factor receptor," Immunology Today, vol. 12(7):220-223 (1991).

Marsters, Scot A. et al., "Identification of Cysteine-rich Domains of the Type 1 Tumor Necrosis Factor Receptor Involved in Ligand Binding," The Journal of Biological Chemistry, vol. 267(9):5747-5750 (1992).

Matsumoto, Mitsuru et al., "Affinity maturation without germinal centres in lymphotoxin-a-deficient mice," Nature, vol. 382:462-466 (1996).

Matsumoto, Mitsuru et al., "Distinct Roles of Lymphotoxin a and the Type 1 Tumor Necrosis Factor (TNF) Receptor in the Establishment of Follicular Dendritic Cells from the Non-Bone Marrow-derived Cells," J. Exp. Med., vol. 186 (12):1997-2004 (1997).

Matsumoto, Mitsuru et al., "Lymphotoxin-a-deficient and TNF receptor-I-deficient mice define developmental and functional characteristics of germinal centers," Immunological Reviews, vol. 156:137-144 (1997).

Matsumoto, Mitsuru et al., "Role of Lymphotoxin and the Type I TNF Receptor in the Formation of Germinal Centers," Science, vol. 271:1289-1291 (1996).

Mauri, Davide N. et al., "LIGHT, a New Member of the TNF Superfamily, and Lymphotoxin a Are Ligands for Herpesvirus Entry Mediator," Immunity, vol. 8:21-30 (1998).

Mendlovic, Shlomo et al., "Induction of a systemic lupus erythematosus-like disease in mice by a common human anti-DNA idiotype," Proc. Natl. Acad. Sci. USA, vol. 85:2260-2264 (1988).

Merriam-Webster Online Dictionary, "composition," (2004).

Miller, Glenn T. et al., "Specific Interaction of Lymphocyte Function-associated Antigen 3 with CD2 Can Inhibit T Cell Responses," J. Exp. Med., vol. 178:211-222 (1993).

Modlin, Robert L. et al., "Type 2 cytokines and negative immune regulation in human infections," Current Opinion in Immunology, vol. 5:511-517 (1993).

Mohan, Chandra et al., "Interaction Between CD40 and Its Ligand gp39 in the Development of Murine Lupus Nephritis," The Journal of Immunology, vol. 154:1470-1480 (1995).

Mohler, Kendall M. et al., "Suluble Tumor Necrosis Factor (TNF) Receptors Are Effective Therapeutic Agents in Lethal Endotoxemia and Function Simultaneously as Both TNF Carriers and TNF Antagonists," Journal of Immunology, vol. 151:1548-1561 (1993).

Montgomery, Rebecca I. et al., "Herpes Simplex Virus-1 Entry into Cells Mediated by a Novel Member of the TNF/NGF Receptor Family," Cell, vol. 87:427-436 (1996).

Morrison, Sherie L. et al., "Chimeric human antibody molecules: Mouse antigen-binding domains with human constant region domains," Proc. Natl. Acad. Sci. USA, vol. 81:6851-6855 (1984).

Morrison, Sherie L., "In Vitro Antibodies: Strategies for Production and Application," Annu. Rev. Immunol., vol. 10:239-265 (1992).

Morrissey, Philip J. et al., "CD4+ T Cells That Expess High Levels of CD45RB Induce Wasting Disease When Transferred into Congenic Severe Combined Immunodeficient Mice. Disease Development Is Prevented by Cotrasfer of Purified CD4+ T Cells," J. Exp. Med., vol. 178:237-244 (1993).

Naismith, James H. et al., "Seeing Double: Crystal Structures of the Type I TNF Receptor," Journal of Molecular Recognition, vol. 9:113-117 (1996).

Nakache, Maurice et al., "The mucosal vascular addressin is a tissue-specific endothelial cell adhesion molecule for circulating lymphocytes," Nature, vol. 337:179-181 (1989).

Neumann, Brigitte et al., "Defective Peyer's Patch Organogenesis in Mice Lacking the 55-kD Receptor for Tumor Necrosis Factor," J. Exp. Med., vol. 184:259-264 (1996).

Ngo, J. Thomas et al., "Computational Complexity, Protein Structure Prediction, and the Levinthal Paradox," The Protein Folding Problem and Tertiary Structure Prediction, Birkhauer, Kenneth M. Merz, Jr. (Ed.), Chpt. 14, pp. 433-506 (1994).

Nicola, Anthony V. et al., "Monoclonal Antibodies to Distinct Sites on Herpes Simplex Virus (HSV) Glycoprotein D Block HSV Binding to HVEM," Journal of Virology, vol. 72(5):3595-3601 (1998).

Niederle, Norbert et al., "Long-Term Treatment of Chronic Myelogenous Leukemia with Different Interferons: Results from Three Studies," Leukemia and Lymphoma, vol. 9:111-119 (1993).

Nilsson, Joakim et al., "Affinity Fusion Strategies for Detection, Purification, and Immobilization of Recombinant Proteins," Protein Expression and Purification, vol. 11:1-16 (1997).

Old, Lloyd J., "Tumor Necrosis Factor (TNF)," Science, vol. 230:630-632 (1985).

Onishi, Tetsuro et al., "A Study on Direct Antitumor Activity of Bropirimine (Oral Interferon Inducer) for Renal Cell Carcinoma," Acta Urol. Jpn., vol. 40:195-200 (1994).

Pasparakis, Manolis et al., "Immune and Inflammatory Responses to TNFa Deficient Mice: A Critical Requirement for TNFa in Germinal Centre Formation and in the Maturation of the Humoral Immune Response," Eur. Cytokine Network, vol. 7(2):239, No. 132 (1996).

Pass, Harvey I. et al., "The Macrophage, TNF, and Other Cytokines," Basic Biology for the Thoracic Surgeon, vol. 5 (1):73-90 (1995).

Paul, Nina L. et al., "Lymphotoxin Activation by Human T-Cell Leukemia Virus Type I-Infected Cell Lines: Role of NF-kB," Journal of Virology, vol. 64(11):5412-5419 (1990).

Abe, Yasuhito et al., "Expression of Membraine-associated Lymphotoxin/Tumor Necrosis Factor-b on Human Lymphokine-activated Killer Cells," Jpn. J. Cancer Res., vol. 82:23-26 (1991).

Abe, Yasuhito et al., "Studies of Membrane-Associated and Soluble (Secreted) Lymphotoxin in Human Lymphokine-Activated T-Killer Cells in Vitro," Lymphokine and Cytokine Research, vol. 11(2):115-121 (1992).

Acharya, S.K. et al., "A preliminary open trial on interferon stimulator (SNMC) derived from *Glycyrrhiza glabra* in the treatment of subacute hepatic failure," Indian J. Med. Res. [B], vol. 98:69-74 (1993).

Aebersold, Ruedi H. et al., "Internal amino acid sequence analysis of proteins separated by one- or two-dimensional gel electrophoresis after in situ protease digestion on nitrocellulose," Proc. Natl. Acad. Sci. USA, vol. 84:6970-6974 (1987).

Aggarwal, Bharat B. et al., "Human Lymphotoxin," The Journal of Biological Chemistry, vol. 259(1):686-691 (1984).

Aggarwal, Bharat B. et al., "Primary Structure of Human Lymphotoxin Derived from 1788 Lymphoblastoid Cell Line," The Journal of Biological Chemistry, vol. 260(4):2334-2344 (1985).

Aggarwal, Bharat B. et al., "Tumor necrosis factors: Developments during the last decade," Eur. Cytokine Netw., vol. 7(2):93-124 (1996).

Akashi, Makoto et al., "Lymphotoxin: Stimulation and Regulation of Colony-Stimulating Factors in Fibroblasts," Blood, vol. 74(7):2383-2390 (1989).

Alderson, Mark R. et al., "Molecular and biological characterization of human 4-1BB and its ligand," Eur. J. Immunol., vol. 24:2219-2227 (1994).

Alderson, Mark R. et al., "Regulation of apoptosis and T cell activation by Fas-specific mAb," International Immunology, vol. 6(11):1799-1806 (1994).

Alexopoulou, Lena et al., "Immunoregulatory Activities of Transmembrane TNF Revealed in Transgenic and Mutant Mice," 6th International TNF Congress, p. 228, No. 110 (1996).

Alimzhanov, Marat B. et al., "Abnormal development of secondary lymphoid tissues in lymphotoxin b-deficient mice," Proc. Natl. Acad. Sci. USA, vol. 94:9302-9307 (1997).

Amiri, Payman et al., "Tumour necrosis factor a restores granulomas and induces parasite egg-laying in schistosome-infected infected SCID mice," Nature, vol. 356:604-607 (1992).

Anderson, W. French, "Human gene therapy," Nature, vol. 392:25-30 (1998).

Andersson, Ulf et al., "Characterization of individual tumor necrosis factor a- and b-producing cells after polyclonal T cell activation," Journal of Immunological Methods, vol. 123:233-240 (1989).

Andrews, Janet S. et al., "Characterization of the Receptor for Tumor Necrosis Factor (TNF) and Lymphotoxin (LT) on Human T Lymphocytes, TNF and LT Differ in Their Receptor Binding Properties and the Induction of MHC Class I Proteins on a Human CD4+ T Cell Hybridoma," The Journal of Immunology, vol. 144(7):2582-2591 (1990).

Androlewicz, Matthew J. et al., "Lymphotoxin Is Expressed as a Hetermeric Complex with a Distinct 33-kDa Glycoprotein on the Surface of an Activated Human T Cell Hybridoma," The Journal of Biological Chemistry, vol. 267 (4):2542-2547 (1992).

Armitage, Richard J. et al., "Molecular and biological characterization of a murine ligand for CD40," Nature, vol. 357:80-82 (1992).

Arulanandam, Antonio R.N. et al., "A Soluble Multimeric Recombinant CD2 Protein Identifies CD48 as a Low Affinity Ligand for Human CD2: Divergence of CD2 Ligands during the Evolution of Humans and Mice," J. Exp. Med., vol. 177:1439-1450 (1993).

Ashkenazi, Avi et al., "Protection against endotoxic shock by a tumor necrosis factor receptor immunoadhesin," Proc. Natl. Acad. Sci. USA, vol. 88:10535-10539 (1991).

Badenhoop, K. et al., "TNF-a gene polymorphisms in Type 1 (insulin-dependent) diabetes mellitus," Diabetologia, vol. 32:445-448 (1989).

Baens, Mathijs et al., "Construction and Evaluation of a hncDNA Library of Human 12p Transcribed Sequences Derived from a Somatic Cell Hybrid," Genomics, vol. 16:214-218 (1993).

Banks, Theresa A. et al., "Lymphotoxin-a-Deficient Mice," The Journal of Immunology, vol. 155:1685-1693 (1995).

Banner, David W. et al., "Crystal Structure of the Soluble Human 55 kd TNF Receptor-Human TNFb Complex: Implications for TNF Receptor Activation," Cell, vol. 73:431-445 (1993).

Barnetson, "Hypersensitivity—Type IV," Mosby-Year Book Europe Ltd., Chpt. 22, pp. 22.1-22.12 (1993).

Baum, Peter R. et al., "Molecular characterization of murine and human OX40/OX40 ligand systems: identification of a human OX40 ligand as the HTLV0-1-regulated protein gp34," The EMBO Journal, vol. 13(17):3992-4001 (1994).

Bernstein, David I. et al., "Effects of therapy with an immunomodulator (imiquimod, R-837) alone with the acyclovir on genital HSV-2 infection in guinea-pigs when begun after lesion development," Antiviral Research, vol. 20:45-55 (1993).

Bethell, Delia B. et al., "Pathophysiologic and Prognostic Role of Cytokines in Dengue Hemorrhagic Fever," JID, vol. 177:778-782 (1998).

Beutler, B. et al., "Passive Immunization Against Cachectin/Tumor Necrosis Factor Protects Mice from Lethal Effect of Endotoxin," Science, vol. 229:869-871 (1985).

Beutler, Bruce et al., "The History, Properties, and Biological Effects of Cachectin," Biochemistry, vol. 27 (20):7575-7582 (1988).

Bloemkolk, Jan-Willem et al., "Effect of Temperature on Hybridoma Cell Cycle and MAb Production," Biotechnology and Bioengineering, vol. 40:427-431 (1992).

Bork, Peer, "Powers and Pitfalls in Sequence Analysis: The 70% Hurdle," Genome Research, vol. 10:398-400 (2000).

Borth, Nicole et al., "Growth and production kinetics of human X mouse and mouse hybridoma cells at reduced temperature and serum content," Journal of Biotechnology, vol. 25:319-331 (1992).

Bowen, Michael A. et al., "Structure and Expression of Murine CD30 and Its Role in Cytokine Production," The Journal of Immunology, vol. 156:442-449 (1996).

Bowie, James U. et al., "Deciphering the Message in Protein Sequences: Tolerance to Amino Acid Substitutions," Science, vol. 247:1306-1310 (1990).

Bringman, Timothy S. et al., "Monoclonal Antibodies to Human Tumor Necrosis Factors Alpha and Beta: Application for Affinity Purification, Immunoassays, adn as Structural Probes," Hybridoma, vol. 6(5):489-507 (1987).

Briskin, Michael J. et al., "MAdCAM-1 has homology to immunoglobulin and mucin-like adhesion receptors and to IgA1," Nature, vol. 363:461-464 (1993).

Browning, Jeffrey L. et al., "Characterization of Surface Lymphotoxin Forms, Use of Specific Monoclonal Antibodies and Soluble Receptors," The Journal of Immunology, vol. 154:33-46 (1995).

Browning, Jeffrey L. et al., "Lymphotoxin and an Associated 33-kDa Glycoprotein Are Expressed on the Surface of an Activated Human T Cell Hybridoma," The Journal of Immunology, vol. 147(4):1230-1237 (1991).

Browning, Jeffrey L. et al., "Lymphotoxin b, a Novel Member of the TNF Family That Forms a Heteromeric Complex with Lymphotoxin on the Cell Surface," Cell, vol. 72:847-856 (1993).

Browning, Jeffrey L. et al., "Preparation and Characterization of Soluble Recombinant Heterotrimeric Complexes of Human Lymphotoxins a and b," The Journal of Biological Chemistry, vol. 271(15):8618-8626 (1996).

Browning, Jeffrey L. et al., "Signaling through the Lymphotoxin b Receptor Induces the Death of Some Adenocarcinoma Tumor Lines," J. Exp. Med., vol. 183:867-878 (1996).

Browning, Jeffrey et al., "Studies on the Differing Effects of Tumor Necrosis Factor and Lymphotoxin on the Growth of Several Human Tumor Lines," The Journal of Immunology, vol. 143(6):1859-1867 (1989).

Bucay, Nathan et al., "Osteoprotegerin-deficient mice develop early onset osteoporosis and arterial calcification," Genes & Development, vol. 12:1260-1268 (1998).

Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, vol. 111:2129-2138 (1990).

Cavender, Druie E. et al., "Endothelial Cell Activation Induced by Tumor Necrosis Factor and Lymphotoxin," American Journal of Pathology, vol. 134(3):551-560 (1989).

Cavender, Druie et al., "Pathways to chronic inflammation in rheumatoid synovitis," Federation Proceedings, vol. 46:113-117 (1987).

Cavert, Winston et al., "Kinetics of Response in Lymphoid Tissues to Antiretroviral Therapy of HIV-1 Infection," Science, vol. 276:960-964 (1997).

Chaplin, David D. et al., "Cytokine regulation of secondary lymphoid organ development," Current Opinion in Immunology, vol. 10:289-297 (1998).

Chen, Chyi-Ying A. et al., "AU-rich elements: characterization and importance in mRNA degradation," TIBS, vol. 20:465-470 (1995).

* cited by examiner

MLLPWATSAP GLAWGPLVLG LFGLLAA SQDQAVP PYASENQTCR DQEKEYYEPQ
HRICCSRCPP GTYVSAKCSR IRDTVCATCA ENSYNEHWNY LTICQLCRPC
DPVMGLEEIA PCTSKRKTQC RCQPGMFCAA WALECTHCEL LSDCPPGTEA
ELKDEVGKGN NHCVPCKAGH FQNTSSPSAR CQPHTRCENQ GLVEAAPGTA
QSDTTCKNPL EPLPPEMSGT MVDKTHTCPP CPAPELLGGP SVFLFPPKPK
DTLMISRTPE VTCVVVDVSH EDPEVKFNWY VDGVEVHNAK TKPREEQYNS
TYRVVSVLTV LHQDWLNGKE YKCKVSNKAL PAPIEKTISK AKGQPREPQV
YTLPPSRDEL TKNQVSLTCL VKGFYPSDIA VEWESNGQPE NNYKTTPPVL
DSDGSFFLYS KLTVDKSRWQ QGNVFSCSVM HEALHNHYTQ KSLSLSPGK
(SEQ ID NO: 6)

MLLPWATSAP GLAWGPLVLG LFGLLAA AVPPYASENQTCR DQEKEYYEPQ
HRICCSRCPP GTYVSAKCSR IRDTVCATCA ENSYNEHWNY LTICQLCRPC
DPVMGLEEIA PCTSKRKTQC RCQPGMFCAA WALECTHCEL LSDCPPGTEA
ELKDEVGKGN NHCVPCKAGH FQNTSSPSAR CQPHTRCENQ GLVEAAPGTA
QSDTTCKNPL EPLPPEMSGT MVDKTHTCPP CPAPELLGGP SVFLFPPKPK
DTLMISRTPE VTCVVVDVSH EDPEVKFNWY VDGVEVHNAK TKPREEQYNS
TYRVVSVLTV LHQDWLNGKE YKCKVSNKAL PAPIEKTISK AKGQPREPQV
YTLPPSRDEL TRNQVSLTCL VKGFYPSDIA VEWESNGQPE NNYKTTPPVL
DSDGSFFLYS KLTVDKSRWQ QGNVFSCSVM HEALHNHYTQ KSLSLSPG
(SEQ ID NO: 8)

```
                                                1tbR095 + wt ALIGNMENTS.apr 329                340        350        360        370        380        390        400       410
LTBR01  (329)  TLPPSRDHFLTKNQVSLTCLVKGFYPSDIAVEWESNGQPENNYKTTPPVLDSDGSFFLYSKLTVDKSRWQQGNVFSCSVMHEA
LTBR05  (329)  TLPPSRDHFLTKNQVSLTCLVKGFYPSDIAVEWESNGQPENNYKTTPPVLDSDGSFFLYSKLTVDKSRWQQGNVFSCSVMHEA
LTBR06  (325)  TLPPSRDHFLTKNQVSLTCLVKGFYPSDIAVEWESNGQPENNYKTTPPVLDSDGSFFLYSKLTVDKSRWQQGNVFSCSVMHEA
LTBR09  (325)  TLPPSRDHFLTKNQVSLTCLVKGFYPSDIAVEWESNGQPENNYKTTPPVLDSDGSFFLYSKLTVDKSRWQQGNVFSCSVMHEA
                                                                                                Section 6
                     411                426
LTBR01  (411)  LHNHYTQKSLSLSPGK
LTBR05  (411)  LHNHYTQKSLSLSPG-
LTBR06  (407)  LHNHYTQKSLSLSPG-
LTBR09  (407)  LHNHYTQKSLSLSPG-
```

*Fig. 2B*

```
AVPPYASENQ TCRDQEKEYY EPQHRICCSR CPPGTYVSAK CSRIRDTVCA TCAENSYNEH    60
WNYLTICQLC RPCDPVMGLE EIAPCTSKRK TQCRCQPGMF CAAWALECTH CELLSDCPPG   120
TEAELKDEVG KGNNHCVPCK AGHFQNTSSP SARCQPHTRC ENQGLVEAAP GTAQSDTTCK   180
NPLEPLPPEW SGTMVDKTHT CPPCPAPELL GGPSVFLFPP KPKDTLMISR TPEVTCVVVD   240
VSHEDPEVKF NWYVDGVEVH NAKTKFREEQ YNSTYRVVSV LTVLHQDWLN GKEYKCKVSN   300
KALPAPIEKT ISKAKGQFRE PQVVTLPPSR DELTKNQVSL TCLVKGFYPS DIAVEWESNG   360
QPENNYKTTP PVLDSDGSFF LYSKLTVDKS RWQQGNVFSC SVMHEALHNH YTQKSLSLSP   420
G                                                                  421

(SEQ ID NO: 5)
```

Fig. 4

AVPPYASEQQ TCRDQEKEYY EPQHRICCSR CPPGTYVSAK CSRIRDTVCA

TCAENSYNEH WNYLTICQLC RPCDPVMGLE EIAPCTSKRK TQCRCQPGMF

CAAWALECTH CELLSDCPPG TEAELKDEVG KGNNHCVPCK AGHFQQTSSP

SARCQPHTRC ENQGLVEAAP GTAQSDTTCK NPLEPLPPEM SGTMVDKTHT

CPPCPAPELL GGPSVFLFPP KPKDTLMISR TPEVTCVVVD VSHEDPEVKF

NWYVDGVEVH NAKTKPREEQ YNSTYRVVSV LTVLHQDWLN GKEYKCKVSN

KALPAPIEKT ISKAKGQPRE PQVYTLPPSR DELTKNQVSL TCLVKGFYPS

DIAVEWESNG QPENNYKTTP PVLDSDGSFF LYSKLTVDKS RWQQGNVFSC

SVMHEALHNH YTQKSLSLSP G (SEQ ID NO: 10)

*Fig. 5*

| Plasmid # | Molecule | Hinge designs | Comments |
|---|---|---|---|
| pXLTBR.9 | LTBRIgG | ~VDKTHTCPPCPAP~ | LTBR/6 hinge |
| 2211 D196N<br>2212 T198N | Glycosylation mutants -G1Fc | ~VNKTHTCPPCPAP~<br>~VDKNHTCPPCPAP~ | Glycosylation site |
| 2221 | Valine deletion -G1Fc | ~DKTHTCPPCPAP~ | Deleted V |
| 2217 | Full length -G1Fc | ~EPKSCDKTHTCPPCPAP~ | Complete IgG1 hinge exon |
| 2219 | G4-hinge-G4Fc | ~ESKYGPPCPPCPAP~ | S228P no scrambling |
| 2218 | G2-hinge-G2Fc | ~CCVECPPCPAPPVAGP~ | G2 hinge exon |
| 2220 | Short hinge -G1Fc | ~CPPCPAP~ | |

*Fig. 6*

Bold highlights changes from in hinge sequence from initial molecule

| Hinge, Construct # | Yield Protein A total mg (1L culture) | Percent Aggregate Analytical GF | Affinity evaluation | Live/Dead | Post S-200 SEC Total mg |
|---|---|---|---|---|---|
| LTBR06 | 184**** | 23 | wt | ~10 | ND |
| Gly mutant D196N, 2211 | 49 | 20 | wt | ND | 25.0 |
| Gly mutant T198N, 2212 | 14.3 | 20 | fair | ND | 4.7 |
| Full length 2217 | 23.3 | 20 | wt | ND | 13.1 |
| G2-G2Fc, 2218 | 9.5 | 20 * | fair | ND | 4.4 |
| S228P-G4-Fc, 2219 | 21.2 | 44 ** | fair | ND | 6.9 |
| Truncated G1, 2220 | 38.7 | 15 | wt | ND | 22.6 |
| Y-deletion, 2221 | 28.6 | 23 | ND | ND | 10.2 |

*multiple LTBRIgG peaks, ** included some fore foot off protein A
ND= not determined, fair= less than wt apparent affinity, Wt= equivalent to wt apparent affinity.
*** Selected clone is responsible for higher titer.

*Fig. 7*

COMPOSITIONS COMPRISING VARIANT LT-B-R-IG FUSION PROTEINS

RELATED APPLICATIONS

This application is a Continuation of PCT Appln. No. PCT/US2008/003548, filed on Mar. 17, 2008 which claims the benefit of U.S. Provisional Application. No. 60/918,518, filed on Mar. 15, 2007. This application is also a Continuation-in-Part of U.S. application Ser. No. 12/446,041, filed Apr. 17, 2009 which claims benefit of PCT Application No. PCT/US007/081761, filed on Oct. 18, 2007 and U.S. Provisional Application No. 60/862,343, filed Oct. 20, 2006. Each of these applications is incorporated in its entirety herein.

BACKGROUND

Protein heterogeneity can be caused by a range of post-translational modifications. Protein heterogeneity often results from different types of post-translational modifications, including carboxylation, hydroxylation, proteolytic processing, sulfation, and glycosylation, the latter of which is the most common modification (Walsh and Jefferis (2006) *Nat Biotech* 24(10): 1241). Post-translational modifications can potentially affect product production levels (by influencing, for example, the degree of proper protein folding), stability, and a range of pharmacokinetic and pharmacodynamic parameters, as well as safety and immunogenicity. Post-translational modifications of therapeutic biologics, or protein-based biopharmaceuticals, may affect protein properties relevant to their therapeutic application.

N and/or C-terminal heterogeneity is an example of protein heterogeneity which must be considered in the manufacture of protein-based biopharmaceuticals. N-terminal heterogeneity results from proteolytic processing at the amino terminal portion of the protein, where such processing may result in a population of proteins having different sizes. Variations in N-terminal proteolysis may occur in proteins comprising a signal sequence. In addition, N-terminal glutamine residues can undergo spontaneous cyclization to form pyroglutamic acid. Thus, obtaining a homogenous population of proteins which can be used for therapeutic purposes often presents a challenge.

Lymphotoxin beta receptor (LTBR) is a member of the tumor necrosis factor receptor (TNFR) family. The receptor is expressed on the surface of cells in the parenchyma and stroma of most lymphoid organs but is absent on T- and B-lymphocytes. Signaling through LTBR by the LTα/β heterotrimer (LT) is important during lymphoid development. LTBR is also known to bind the ligand LIGHT (homologous to lymphotoxins, exhibits inducible expression, and competes with herpes simplex virus glycoprotein D for HVEM, a receptor expressed by T lymphocytes), which has been implicated in T-cell driven events, both in the periphery and in the thymus. LT and LIGHT are expressed on the surface of activated lymphocytes. Blocking the LT pathway with a soluble decoy LTBR has been shown to be effective to treat autoimmune disease in various animal models.

The development of soluble forms of LTBR having reduced heterogeneity and optimal dosing regimens for administration of these molecules would be of great benefit.

SUMMARY OF THE INVENTION

In one aspect the invention pertains to a composition comprising a population of lymphotoxin-β receptor (LT-β-R)-Ig-fusion proteins which comprise a variant LT-β-R extracellular domain of 193 or 194 amino acids in length and a variant Ig portion of 227 amino acids in length, wherein at least 90% of the LT-β-R-Ig-fusion proteins are missing no more than 5 amino acids from the N-terminus of the mature form of the wild type LT-β-R extracellular domain set forth in SEQ ID NO:21 and wherein the LT-β-R-Ig-fusion proteins lack N-terminal pyroglutamic acid.

In one embodiment, the N-terminal amino acid of the variant LT-β-R-Ig fusion protein is a non-polar amino acid.

In one embodiment, the non polar amino acid is either a valine (amino acid six of the mature form of the wild type LT-β-R extracellular domain of SEQ ID NO:21) or an alanine (amino acid five of the mature form of the wild type LT-β-R extracellular domain of SEQ ID NO:21).

In one embodiment, the N-terminal amino acid of at least 95% of the LT-β-R-Ig-fusion proteins is either a valine (amino acid six of the mature form of the wild type LT-β-R extracellular domain of SEQ ID NO:21) or an alanine (amino acid five of the mature form of the wild type LT-β-R extracellular domain of SEQ ID NO:21).

In one embodiment, the composition is made by expressing a nucleic acid molecule comprising a nucleotide sequence encoding the extracellular domain of LTBR set forth in SEQ ID NO:4 in a mammalian cell.

In one embodiment, the nucleic acid molecule comprises the sequence set forth in SEQ ID NO:3.

In one embodiment, variant Ig portion comprises Fc regions of an IgG1 isotype.

In one embodiment, the variant Ig portion comprises the amino acid sequence set forth in SEQ ID NO:2.

In one embodiment, the Ig portion is non-glycosylated.

In one embodiment, the composition is made by expressing a nucleic acid molecule encoding the LT-β-R-Ig fusion protein set forth in SEQ ID NO:5 in a mammalian cell.

In one embodiment, the nucleic acid molecule comprises the sequence set forth in SEQ ID NO:7.

In one embodiment, the step of expressing is done at manufacturing scale.

In one aspect, the invention pertain to a composition comprising a population of lymphotoxin-β receptor-immunoglobulin (LT-β-R-Ig)-fusion proteins comprising a variant LT-β-R extracellular domain and a variant Ig portion, wherein the variant LT-β-R extracellular domain is aglycosylated.

In one embodiment, the aglycosylated extracellular domain of LTBR comprises amino acids 1 to 194 of SEQ ID NO: 10.

In another aspect, the invention pertains to a composition comprising a population of lymphotoxin-β receptor-immunoglobulin (LT-β-R-Ig)-fusion proteins, the fusion proteins comprising a variant LT-β-R extracellular domain of 193 or 194 amino acids in length and a variant Ig portion, wherein the population has reduced N-terminal pyroglutamic acid formation, and reduced C-terminal heterogeneity compared to wild-type LT-β-R-Ig fusion proteins.

In one embodiment, at least 90% of the LT-β-R-Ig-fusion proteins comprise a variant LT-β-R extracellular domain as set forth the amino acid sequence of SEQ ID NO: 4 or SEQ ID NO: 23.

In one embodiment, the variant Ig portion comprises a mutation in the hinge region.

In one aspect, the invention pertains to a pharmaceutical composition comprising a population of lymphotoxin-β receptor (LT-β-R)-Ig-fusion proteins which comprise a variant LT-β-R extracellular domain of 193 or 194 amino acids in length and a variant Ig portion of 227 amino acids in length, wherein at least 90% of the LT-β-R-Ig-fusion proteins are missing no more than 5 amino acids from the N-terminus of the mature form of the wild type LT-β-R extracellular domain set forth in SEQ ID NO:21 and wherein the LT-β-R-Ig-fusion proteins lack N-terminal pyroglutamic acid and a pharmaceutically acceptable carrier.

In one embodiment, the N-terminal amino acid of the variant LT-β-R-Ig fusion protein is a non-polar amino acid.

In one embodiment, the non polar amino acid is either a valine (amino acid six of the mature form of the wild type LT-β-R extracellular domain of SEQ ID NO:21) or an alanine (amino acid five of the mature form of the wild type LT-β-R extracellular domain of SEQ ID NO:21).

In one embodiment, the N-terminal amino acid of at least 95% of the LT-β-R-Ig-fusion proteins is either a valine (amino acid six of the mature form of the wild type LT-β-R extracellular domain of SEQ ID NO:21) or an alanine (amino acid five of the mature form of the wild type LT-β-R extracellular domain of SEQ ID NO:21).

In one embodiment, the composition is made by expressing a nucleic acid molecule comprising a nucleotide sequence encoding the extracellular domain of LTBR set forth in SEQ ID NO:4 in a mammalian cell.

In one aspect, the invention pertains to a method of treating an autoimmune disorder comprising administering the pharmaceutical composition of claim 23 to a subject in need thereof.

In one embodiment, the autoimmune disorder is selected from the group consisting of rheumatoid arthritis, Crohn's disease, or systemic lupus erythematosus (SLE).

In one embodiment, the invention pertains to a pharmaceutical composition comprising a population of lymphotoxin-β receptor-immunoglobulin (LT-β-R-Ig)-fusion proteins, the fusion proteins comprising a variant LT-β-R extracellular domain of 193 or 194 amino acids in length and a variant Ig portion, wherein the population has reduced N-terminal pyroglutamic acid formation and reduced C-terminal heterogeneity compared to wild-type LT-β-R-Ig fusion proteins and a pharmaceutically acceptable carrier.

In one embodiment, at least 90% of the LT-β-R-Ig-fusion proteins comprise a variant LT-β-R extracellular domain as set forth the amino acid sequence of SEQ ID NO: 4 or SEQ ID NO: 23.

In one embodiment, the variant Ig portion comprises a mutation in the hinge region.

In one embodiment, the amino acid sequence set forth in SEQ ID NO:5.

In one aspect, the invention pertains to a method of treating an autoimmune disorder comprising administering the pharmaceutical composition of claim 29 to a subject in need thereof.

In one embodiment, the autoimmune disorder is selected from the group consisting of rheumatoid arthritis, Crohn's disease, or systemic lupus erythematosus (SLE).

In one embodiment, the autoimmune disorder is rheumatoid arthritis.

In one embodiment, the pharmaceutical composition is administered to the subject at a dose of from about 0.6 to 3 mg/kg biweekly.

In one embodiment, the pharmaceutical composition is administered subcutaneously.

In one aspect, the invention pertains to an isolated polypeptide comprising a variant LT-β-R extracellular domain of 193 or 194 amino acids in length and a variant Ig portion of 227 amino acids in length, wherein the polypeptide is missing no more than 5 amino acids from the N-terminus of the mature form of the wild type LT-β-R extracellular domain set forth in SEQ ID NO:21 and wherein the polypeptide lacks N-terminal pyroglutamic acid.

In one embodiment, the N-terminal amino acid is a non-polar amino acid.

In one embodiment, the non polar amino acid is either a valine (amino acid six of the mature form of the wild type LT-β-R extracellular domain of SEQ ID NO:21) or an alanine (amino acid five of the mature form of the wild type LT-β-R extracellular domain of SEQ ID NO:21).

In one embodiment, the polypeptide is made by expressing a nucleic acid molecule comprising a nucleotide sequence encoding the extracellular domain of LTBR set forth in SEQ ID NO:4 in a mammalian cell.

In one embodiment, the invention pertains to an isolated nucleic acid molecule encoding the polypeptide of the invention.

In one embodiment, the nucleic acid molecule comprises of the nucleotide sequence set forth in SEQ ID NO:7.

In one embodiment, the mention pertains to a vector comprising the nucleic acid molecule of the invention In one embodiment, the invention pertains to a host cell expressing the vector of the invention.

In one embodiment, the cell is a Chinese Hamster Ovary (CHO) cell.

In one embodiment, the invention pertains to a process for making a composition comprising a population of lymphotoxin-β receptor (LT-β-R)-Ig-fusion proteins which comprise a variant LT-β-R extracellular domain and a variant Ig portion, wherein at least 90% of the LT-β-R-Ig-fusion proteins are missing no more than 5 amino acids from the N-terminus of the mature form of the wild type LT-β-R extracellular domain set forth in SEQ ID NO:21, the process comprising, expressing a nucleic acid molecule encoding the LT-β-R-Ig fusion protein set forth in SEQ ID NO:8 in a mammalian cell, obtaining the population from the culture supernatant, and, optionally, purifying the supernatant, to thereby obtain a composition comprising a population of lymphotoxin-β receptor (LT-β-R)-Ig-fusion proteins which comprise a variant LT-β-R extracellular domain and a variant Ig portion, wherein at least 90% of the LT-β-R-Ig-fusion proteins are missing no more than 5 amino acids from the N-terminus of the mature form of the wild type LT-β-R portion set forth in SEQ ID NO:21.

In one embodiment, the nucleic acid molecule comprises the nucleotide sequence set forth in SEQ ID NO:7.

In one embodiment, the nucleic acid molecule consists of the nucleotide sequence set forth in SEQ ID NO:7.

In one embodiment, the invention pertains to a method of treating rheumatoid arthritis in a human subject, the method comprising administering to the subject a dose of LT-β-R-Ig fusion protein, wherein the dose is sufficient to maintain an average concentration of from about 0.14 ug/ml to about 3.5 ug/ml in the serum of the subject.

In another aspect, the invention pertains to a method of treating rheumatoid arthritis in a human subject, the method comprising administering to the subject a dose of LT-β-R-Ig fusion protein, wherein the dose is sufficient to maintain an average a minimal average concentration of about 0.6 ug/ml in the serum of the subject.

In one embodiment, the LTBR-Ig fusion protein comprises the amino acid sequence set forth in SEQ ID NO:5.

In one embodiment, the concentration is achieved by administering LT-β-R-Ig fusion protein at a dose of from about 0.01 to about 5 mg/kg once every 7-60 days.

In one embodiment, the invention pertains to a method of treating rheumatoid arthritis in a human subject, the method comprising administering to the subject a dose of LT-β-R-Ig fusion protein of from about 0.6 to 3 mg/kg not more than twice every 7-30 days.

In one embodiment, method comprising administering to the subject a dose of LT-β-R-Ig fusion protein of from about 0.6 to 3 mg/kg once every 7-14 days.

In one embodiment, administration is once every 14-30 days.

In one embodiment, administration is once every 28-60 days.

In one embodiment, administration is once every 7-30 days.

In one embodiment, the invention pertains to a method of treating an autoimmune disorder in a human subject, the method comprising administering to the subject a dose of a pharmaceutical composition comprising a population of LT-β-R-Ig fusion proteins comprising a variant LT-β-R extracellular domain of 193 or 194 amino acids in length, wherein at least 90% of the LT-β-R-Ig-fusion proteins are missing no more than 5 amino acids from the N-terminus of the mature form of the wild type LT-β-R extracellular domain set forth in SEQ ID NO:21. and wherein the dose is sufficient to maintain a minimal average concentration of about 0.6 ug/ml in the serum of the subject.

In one embodiment, the LT-β-R-Ig fusion protein further comprises a variant Ig portion.

In one embodiment, the autoimmune disorder is selected from the group consisting of rheumatoid arthritis, Crohn's disease, or systemic lupus erythematosus (SLE).

In one embodiment, the pharmaceutical composition comprises the amino acid sequence set forth in SEQ ID NO:5.

In one embodiment, administration is twice monthly.

In one embodiment, administration once monthly.

In one embodiment, administration is subcutaneous.

In one embodiment, the dose is about 1 mg/kg.

In one embodiment, the dose is about 3 mg/kg.

In one embodiment, the dose is about 1 mg/kg administered about every 7 to 20 days.

In one embodiment, the dose is about 3 mg/kg administered about every 14 to 30 days.

In one embodiment, the dose is about 1 mg/kg administered about every 14 days.

In one embodiment, the autoimmune disorder is rheumatoid arthritis and the subject has been treated with a rheumatoid arthritis drug after being diagnosed with rheumatoid arthritis and prior to administration of the LT-β-R-Ig fusion protein.

In one embodiment, the rheumatoid arthritis drug is chosen from the group consisting of a DMARD, an NSAID, and a corticosteroid.

In one embodiment, the human is a DMARD-inadequate responder.

In one embodiment, the rheumatoid arthritis drug is a TNF inhibitor.

In one embodiment, the rheumatoid arthritis drug is adalimumab (Humira®), etanercept (Enbrel®), or infliximab (Remicade®).

In one embodiment, LT-β-R-Ig is administered in combination with the rheumatoid arthritis drug.

In one embodiment, the human is evaluated to determine if the response to the rheumatoid arthritis drug is inadequate prior to administration of LT-β-R-Ig.

In one embodiment, the human is determined to have an inadequate response to the rheumatoid arthritis drug, and then the human is administered LT-β-R-Ig.

In one embodiment, the human is asymptomatic for a first manifestation of rheumatoid arthritis and is symptomatic for a second manifestation of rheumatoid arthritis.

In one embodiment, LT-β-R-Ig is administered in place of the rheumatoid arthritis drug.

In one embodiment, administration is in combination with a tumor necrosis factor (TNF) inhibitor.

In one embodiment, the TNF inhibitor is adalimumab (Humira®), etanercept (Enbrel®), or infliximab (Remicade®).

In one embodiment, the human is an anti-TNF-inadequate responder.

In one embodiment, administration is in combination with a non-steroidal anti-inflammatory agent (NSAID), a corticosteroid, or a disease modifying antirheumatic drug (DMARD).

In one embodiment, administration is in combination with methotrexate.

In one embodiment, the human is a DMARD-inadequate responder.

BRIEF DESCRIPTION OF DRAWINGS

FIG. 1 describes the changes made from LTBR01 to LTBR06 to improve heterogeneity. The bold letters indicate the secretion sequence, and the italicized/underlines letters indicate the amino acids which are removed in LTBR06 relative to LTBR01, i.e., amino acids 1-4 and the last amino acid (lysine). Three consensus sites for N-linked glycosylation are located at Asn13, 150 and 276. Amino acid positions refer to full length LTBR, i.e., amino acids 1-4 are those which are removed in LTBR06.

FIG. 2 provides an alignment of LTBR01 (SEQ ID NO: 11), LTBR05 (SEQ ID NO: 91, LTBR06 (SEQ ID NO: 5), and LTBR09 (SEQ ID NO: 12). The secretion sequence is omitted from the LTBR sequences.

FIG. 4 describes the amino acid sequence of the LTBR06 construct (mature form of LTBR06 shown in SEQ ID NO: 5). LTBR06 is a disulfide-linked, glycosylated, dimeric protein. There are 28 cysteine residues and 6 glycosylation sites, the latter of which is indicated in bold.

FIG. 5 describes aglycosylated hLTβR hIgG1 (mature form of protein). Asparagine to glutamine mutations in LTβR extracellular domain are shown in bold. The huLTβR is residues 1-204, the huIgG1 Fc is residues 205-431 above (the Fc's glycosylation site is intact).

FIG. 6 describes hinges (SEQ ID NOS: 13-20) of which may be used in the LTBR IgG fusion proteins of the invention.

FIG. 7 describes a table which describes a summary of results from a hinge expression analysis.

DETAILED DESCRIPTION OF INVENTION

Figure 3:
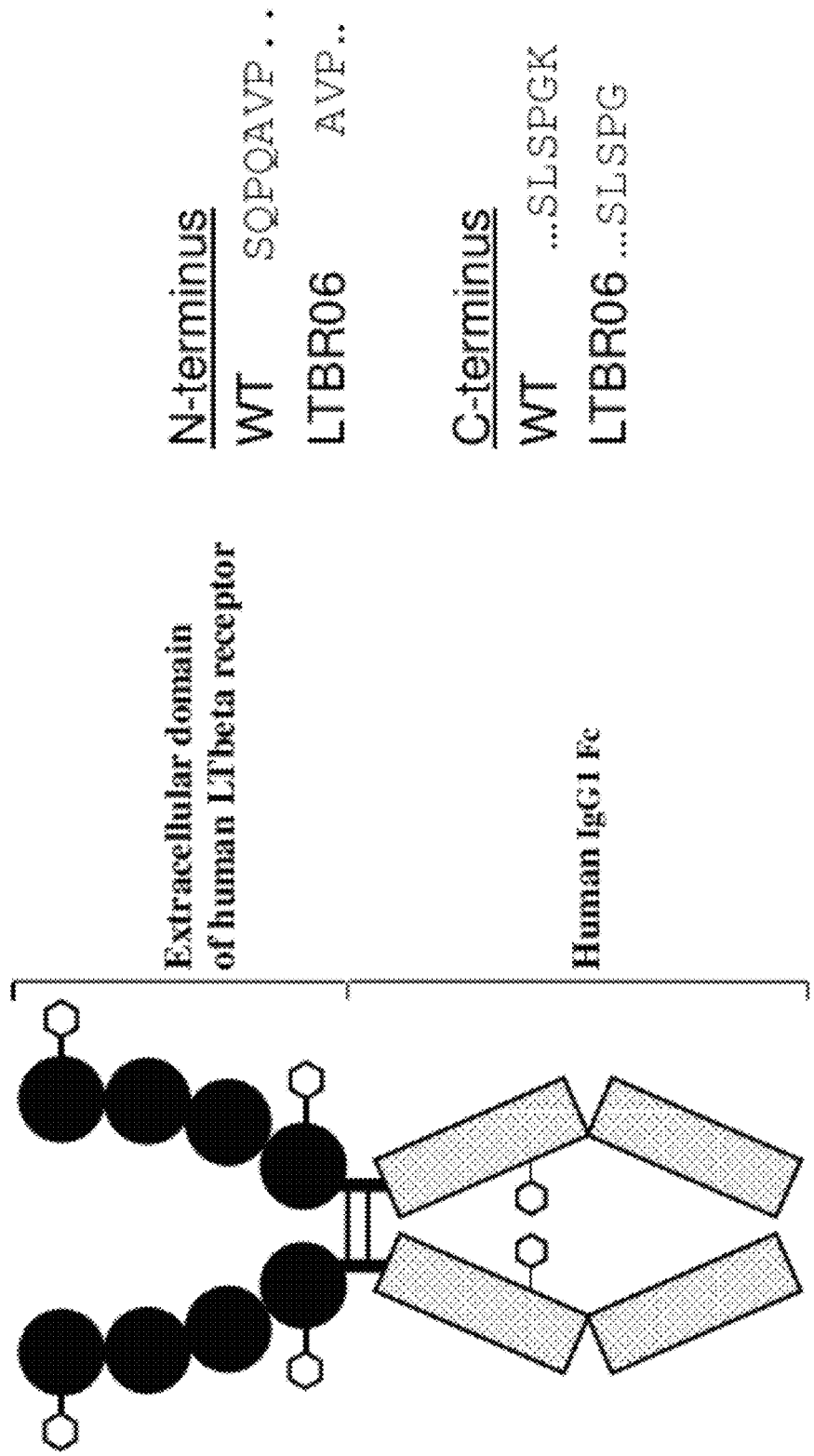
FIG. 3 describes LTBR06 (N-terminus residues 1-3 of SEQ ID NO:5 and C-terminus, residues 417-421 of SEQ ID NO: 5) in comparison to wild type (N-terminus residues 1-7 of SEQ ID NO:11 and C-terminus, residues 421-426 of SEQ ID NO:11) and provides a schematic of the protein.

In order that the present invention may be more readily understood, certain terms are first defined.

The term "fusion protein" refers to a molecule comprising two or more proteins or fragments thereof linked by a covalent bond via their individual peptide backbones, most preferably generated through genetic expression of a polynucleotide molecule encoding those proteins. In a preferred embodiment, the fusion protein includes an immunoglobulin domain.

The generic term "immunoglobulin" comprises five distinct classes of antibody that can be distinguished biochemically. All five classes of antibodies are clearly within the scope of the present invention, the following discussion will generally be directed to the IgG class of immunoglobulin molecules.

The term "immunoglobulin fusion protein" refers to a fusion of a functional portion of a polypeptide (generally comprising the extracellular domain of a cell surface protein) with one or more portions of an immunoglobulin constant region, e.g. the hinge, CH1, CH2 or CH3 domains or portions or combinations thereof. In one embodiment, the polypeptide is a member of the TNF family of receptors. The portions of the Ig molecule may derive from any of the various immunoglobulin isotypes, including, for example, IgG1, IgG2, IgM, IgA etc. Immunoglobulin fusion proteins are referred to herein as Ig for Fc fusion proteins.

In a preferred embodiment, the protein used in the methods and compositions of the invention is an immunoglobulin fusion protein. For example, the fusion protein may comprise a receptor, or ligand binding portion thereof, and a dimerization domain, e.g., an Fc domain.

As used herein, the term "variant LTBR extracellular domain" refers to the mature form of a polypeptide (or protein) having an amino acid sequence that differs from the sequence presented in SEQ ID NO: 1 and SEQ ID NO: 21 (wild type hLTBR) at one or more amino acid positions.

As used herein, the term "variant Ig portion" refers to a polypeptide (or protein) having an amino acid sequence that differs from Fc regions known in the art, including the sequence provided herein as SEQ ID NO: 22, at one or more amino acid positions.

The term "reduced N-terminal heterogeneity" refers to a decrease in the number of proteins in a population having different N-terminal amino acid residues or that occur in different forms relative to a control protein population. For example, expression of a control protein may result in a protein population comprising proteins with missing N-terminal amino acid residues ranging from one amino acid to three amino acids (relative to the predicted translated protein), also described as N-1, N-2, and N-3. In this instance, the population of proteins would include three different types, i.e., N-1, N-2, and N-3. A population of proteins having reduced N-terminal heterogeneity, therefore, would include a population of proteins having less than three different N-terminal amino acid residues, e.g., N-1 and N-2, N-2 and N-3, or N-1 and N-3 types of proteins or reduced percentage of one or more of these types of variant molecules. It should be noted that the N-terminal amino acids themselves may not be different, e.g., for a protein having an N-terminus of N-1 relative to the wild-type form, the N-terminal amino acid may be an alanine and for a protein having an N-terminus of N-3 relative to the wild-type form, the N-terminal amino acid may be also an alanine. Accordingly, in one embodiment, N-terminal heterogeneity has to do with the overall difference in lengths among the proteins within a population (expressed in relative terms to the predicted translated protein). As such, the term "N-#" refers to the number of amino acids deleted from the amino terminus of the wild-type translated protein. For example, if a wild-type predicted protein sequence was AAGTY (SEQ ID NO: 24), an N-1 protein would not comprise the initial A and would instead begin with AGTY (SEQ ID NO: 25), although both proteins begin with A. Similarly, an N-2 protein would begin with GTY.

In another embodiment, N-terminal heterogeneity can be reduced by reducing the potential number of variant forms in a population of proteins. For example, N-terminal glutamine residues can undergo spontaneous cyclization to form pyroglutamic acid which can lead to further heterogeneity. In one embodiment, the formation of pyroglutamic acid is reduced or eliminated compared to that present in wild-type proteins.

The term "reduced C terminal heterogeneity" likewise refers to a decrease in the number of proteins in a population having different C-terminal amino acid residues relative to a control protein population. In addition, the term "C-#" refers to the number of amino acids deleted from the carboxy terminus of a protein.

The term "glycosylation" refers to the covalent linking of one or more carbohydrates to a polypeptide. Typically, glycosylation is a posttranslational event which can occur within the intracellular milieu of a cell or extract therefrom. The term glycosylation includes, for example, N-linked glycosylation (where one or more sugars are linked to an asparagine residue) and/or O-linked glycosylation (where one or more sugars are linked to an amino acid residue having a hydroxyl group (e.g., serine or threonine).

The phrase "TNF family of receptors" refers to any receptor, whether naturally membrane bound or secreted (as in the case of osteoprotegerin), which has the canonical TNF family cysteine bridging patterns or any receptor which binds to a defined member of the TNF family of ligands (e.g. Banner et al 1993). The claimed invention in other embodiments relates to TNF family receptor-Ig fusions obtained by the methods discussed herein, as well as to pharmaceutical preparations comprising them.

A "signal peptide" or "signal sequence" is a peptide sequence that directs a newly synthesized polypeptide to which the signal peptide is attached to the endoplasmic reticulum (ER) for further post-translational processing and distribution. The mature form of a protein refers to the protein without the signal sequence.

As used herein, a "soluble LTBR" is a polypeptide that includes all or a portion of the extracellular domain of human LTBR (e.g., an LTBR immunoglobulin fusion). Preferred soluble LTBRs are soluble molecules which include sufficient sequence from the extracellular region of LTBR that they can bind to a ligand, e.g., LT or LIGHT, with at least 10% and preferably at least 50% of the affinity of the molecule of SEQ ID NO:1.

The term "ligand binding domain" or "ligand binding portion" as used herein refers to any native receptor (e.g., cell surface receptor) or any region or derivative thereof retaining at least a qualitative ligand binding ability, and preferably the biological activity of a corresponding native receptor.

The terms "approximately" and "about", as used herein in reference to a number generally includes numbers that fall within a range of 10% in either direction of the number (greater than or less than the number) unless otherwise stated or otherwise evident from the context (except where such number would exceed 100% of a possible value).

As defined herein, the term "conservative substitutions" denotes the replacement of an amino acid residue by another, biologically similar residue. For example, one would expect conservative amino acid substitutions to have little or no effect on the biological activity, particularly if they represent less than 10% of the total number of residues in the polypeptide or protein. Preferably, conservative amino acids substitutions represent changes in less than 5% of the polypeptide or protein, most preferably less than 2% of the polypeptide or protein (e.g., when calculated in accordance with SEQ ID NO 5, most preferred conservative substitutions would represent fewer than 9 amino acid substitutions in the wild type amino acid sequence). In a particularly preferred embodiment, there is a single amino acid substitution in the sequence, wherein the both the substituted and replacement amino acid are non-cyclic.

Other examples of particularly conservative substitutions include the substitution of one hydrophobic residue such as isoleucine, valine, leucine or methionine for one another, or the substitution of one polar residue for another, such as the substitution of arginine for lysine, glutamic for aspartic acid, or glutamine for asparagine, and the like.

Genetically encoded amino acids generally may be divided into four families: (1) acidic: aspartate, glutamate; (2) basic: lysine, arginine, histidine; (3) nonpolar: alanine, valine, leucine, isoleucine, proline, phenylalanine, methionine, tryptophan; and (4) uncharged polar: glycine, asparagine, glutamine, cysteine, serine, threonine, tyrosine. Phenylalanine, tryptophan, and tyrosine may be classified jointly as aromatic amino acids. In one embodiment, the amino acid at the N-terminal of the polypeptide of the invention is a non-polar, amino acid (i.e., alanine, valine, leucine, isoleucine, phenylalanine, metionine, tryptophan, glycine, and cysteine), excluding imino acids, i.e., proline.

The term "treating" refers to administering a therapy in an amount, manner, and/or mode effective to improve or prevent a condition, symptom, or parameter associated with a disorder or to prevent onset, progression, or exacerbation of the disorder (including secondary damage caused by the disorder), to either a statistically significant degree or to a degree detectable to one skilled in the art. Accordingly, treating can achieve therapeutic and/or prophylactic benefits. An effective amount, manner, or mode can vary depending on the subject and may be tailored to the subject.

The term "inadequate response", "inadequate responder" or "-IR" refers to a patient who, as assessed by the patient or a clinician of ordinary skill, exhibits insufficient efficacy or intolerable or unacceptable toxicity to a particular treatment. Insufficient efficacy can mean a failure to meet a predetermined level of response to treatment. In the case of rheumatoid arthritis (RA), for example, insufficient efficacy may be defined as failure to exhibit at least a 10%, 20%, 25%, 30%, 40%, 50% or more decrease in a clinical parameter of RA, such as tender joint count (TJC), swollen joint count (SJC), patient global assessment of disease activity [PGA visual analog scale (VAS) 0-10 cm], physician global assessment of disease activity (MDGA VAS 0-10 cm) and C-reactive protein (CRP in mg/dl). Intolerable toxicity can be an adverse reaction to an agent that results in medical need or recommendation to discontinue use of the first agent. Examples of intolerable or unacceptable toxicity may include hepatic injury or dysfunction, severe allergic reaction, severe depression or suicidal ideation, anaphylaxis, or injection site reaction.

As used herein, "administered in combination" means that two or more agents (e.g., the soluble LTBR and the second agent) are administered to a subject at the same time or within an interval, such that there is overlap of an effect of each agent on the patient. Preferably the administrations of the first and second agent are spaced sufficiently close together such that a combinatorial effect, e.g., an additive or synergistic effect, is achieved. The interval can be an interval of hours, days or weeks. The agents can be concurrently bioavailable, e.g., detectable, in the subject. In a preferred embodiment at least one administration of one of the agents, e.g., the first agent, is made while the other agent, e.g., the soluble LTBR, is still present at a therapeutic level in the subject.

The term "weekly" means not more than once within a particular 6 to 8 day period, e.g., once every 7 days.

The term "biweekly" means not more than once within a particular 12 to 16 day period, e.g., once every 14 days. The term "monthly" means once a month, e.g, once every 28 to 31 days. The subject is typically a mammal, e.g., human, non-human primate (such as a monkey or ape), dog, cat, rabbit, or agriculture mammal (e.g., horse, cow, pig, and so on). For example, the subject is a human, e.g., a human male or female. The subject can be at least about 18, 25, 30, 45, 50, 55, 60, or 70 years old.

As used herein, the term "minimal average concentration" refers to the mean minimal concentration of drug present in the circulation or in the serum of a subject.

Various aspects of the invention are described in further detail in the following subsections.

I. LTBR-Ig Fusion Proteins and Compositions Thereof

The invention pertains to compositions comprising LBTR-Ig fusion proteins that are improved for therapeutic use in that the population of LTBR-Ig fusions proteins has reduced molecular heterogeneity. The invention provides compositions, including pharmaceutical compositions, comprising LTBR-Ig fusion proteins, as well as proteins, nucleic acids, vectors, host cells, and methods of making the same.

A lymphotoxin-β receptor-immunoglobulin (LTβR-Ig) fusion protein can block signaling between the surface LT ligand and the receptor with consequences on the functional state of follicular dendritic cells (Mackay and Browning 1998). This blocking can furthermore lead to diminished autoimmune disease in rodent models (Mackay et al, 1998, U.S. Ser. No. 08/505,606 filed Jul. 21, 1995 and U.S. Ser. No. 60/029,060 filed Oct. 26, 1996).

Generally, preferred soluble LTBRs of the invention are fusion proteins. A soluble LTBR, as defined herein, is a molecule that includes an LT-binding fragment of the extracellular domain of LTBR. For example, a soluble LTBR can include all or a substantial portion of the extracellular domain of LTBR (e.g., it can include residues 40-200, 35-200, 40-210; 35-220, 32-225, or 28-225 of SEQ ID NO:1). In one embodiment, a soluble LTBR includes residues 32-225 of SEQ ID NO:1. In some embodiments, a soluble LTBR can be modified by covalent attachment of a moiety, e.g., a heterologous polypeptide (e.g., to make an LTBR fusion protein) or a non-polypeptide moiety. In some cases, such moieties can improve a pharmacodynamic or pharmacokinetic parameter, such as solubility or half-life. LTBR fusion proteins can include all or part of the constant region of an antibody (e.g., an Fc domain), transferrin, or albumin, such as human serum albumin (HSA) or bovine serum albumin (BSA). The fusion protein can include a linker region between the LTBR sequence and the non-LTBR protein domain. In some embodiments, a soluble LTBR is modified by covalent attachment to a polymer such as a polyethylene glycol (PEG). While not wishing to be bound by theory or mechanism, such soluble LTBRs can act as decoy receptors to reduce (block) LTBR activity. An exemplary LTBR-Fc has the amino acid sequence of SEQ ID NO:5, 6, 8, 9, or 10.

The soluble LTBR can include all or a fragment of LTBR, e.g., a soluble fragment of LTBR, fused to one or more heterologous protein domains (which domain(s) may increase solubility or lifetime in the blood). An exemplary LTBR moiety is the LTBR sequence of SEQ ID NO:1, or a sequence which differs therefrom by no more than 1, 2, 3, 5, or 10 amino acid residues. The differences can be any difference, e.g., a substitution, deletion or insertion, but is preferably a substitution, e.g., a conservative substitution. Conservative substitutions are usually exchanges of one amino acid for another with similar polarity, steric arrangement, or of the same class (e.g., hydrophobic, acidic or basic). Examples of non-LTBR proteins or domains include all or part of the constant region of an antibody, e.g., an Fc domain, transferrin, or albumin, such as human serum albumin (HSA) or bovine serum albumin (BSA).

In a preferred embodiment, the polypeptide of the invention is an Fc fusion protein containing a polypeptide such as an antibody, and preferably an IgG immunoglobulin, e.g., of the subtype IgG1, IgG2, IgG3, or IgG4, and preferably, of the subtype IgG1 or IgG4. In a preferred embodiment, the foregoing polypeptide binds to a ligand of LTBR. Amino acid numberings herein for portions of an Fc region of a polypeptide correspond to the Kabat numbering system as described, e.g., by Kabat et al., in "Sequences of Proteins of Immunological Interest", U.S. Dept. Health and Human Services, 1983 and 1987. In some embodiments, sequential amino acid numbering, e.g., for sequences presented in the sequence listing, are provided.

In one embodiment, a fusion protein of the invention comprises at least a portion of a hinge region, a CH1, a CH2, and a CH3 region of an immunoglobulin.

Heterogeneity within a protein population may result from post-translational modifications such as variable glycosylation patterns, N-terminal proteolysis, C-terminal proteolysis, and pyroglutamate formation (also referred to herein as pyroglu formation). The invention provides a composition comprising a population of lymphotoxin-β receptor-immunoglobulin (LT-β-R-Ig)-fusion proteins having reduced heterogeneity, including, but not limited to, reduced N-terminal heterogeneity (e.g., with respect to variations in size of molecules or variation in the form of molecules (e.g., pyroglutamic acid containing proteins) or reduced C-terminal heterogeneity, as well as combinations thereof. The reductions in heterogeneity may be attributed to deletions and/or mutations made within the sequence of the LTBR-Ig protein, such that heterogeneity is reduced relative to the wild-type LTBR-Ig fusion protein, i.e., unmutated and/or undeleted LTBR-Ig. An example of a wild-type LTBR-Ig fusion protein is described in SEQ ID NO: 11 (mature form of protein), also referred to as LTBR01. It should be noted that the terms LTβR-Ig and LTBR-Fc are used interchangeably herein.

In a preferred embodiment, an LTβR-Ig fusion protein comprises a variant LTBR extracellular domain and/or a variant Ig portion, e.g., Fc portion of an Ig. In one embodiment of the invention, the LTBR-Ig fusion protein comprises either a LTBR extracellular domain variant, a variant Ig portion, or a combination thereof.

The amino acid and nucleic acid sequences of wild type LTBR are described in the NCBI database as AAH26262 and P36941. The wild type human amino acid sequence of LTBR is also describe as SEQ ID NO: 1. A soluble LTBR can be an LTBR-Fc polypeptide having the sequence of SEQ ID NO:1, or preferably a variant thereof. In a preferred embodiment the soluble LTBR is an LTBR-Fc polypeptide which differs from the sequence of SEQ ID NO:1 by no more than 1, 2, 3, 5, or 10 amino acid residues.

Human LTBR Sequence (GenPept ID No. P36941)

SEQ ID NO: 1 is the immature or nonprocessed human LTBR sequence, i.e., contains the signal sequence. Amino acids in italics indicate signal sequence. Amino acids 28-225 are the extracellular region of LTBR.

```
                                                    (SEQ ID NO: 1)
  1 MLLPWATSAP GLAWGPLVLG LFGLLAASQP QAVPPYASEN QTCRDQEKEY YEPQHRICCS

61 RCPPGTYVSA KCSRIRDTVC ATCAENSYNE HWNYLTICQL CRPCDPVMGL EEIAPCTSKR

121 KTQCRCQPGM FCAAWALECT HCELLSDCPP GTEAELKDEV GKGNNHCVPC KAGHFQNTSS

181 PSARCQPHTR CENQGLVEAA PGTAQSDTTC KNPLEPLPPE MSGTMLMLAV LLPLAFFLLL

241 ATVFSCIWKS HPSLCRKLGS LLKRRPQGEG PNPVAGSWEP PKAHPYFPDL VQPLLPISGD

301 VSPVSTGLPA APVLEAGVPQ QQSPLDLTRE PQLEPGEQSQ VAHGTNGIHV TGGSMTITGN

361 IYIYNGPVLG GPPGPGDLPA TPEPPYPIPE EGDPGPPGLS TPHQEDGKAW HLAETEHCGA

421 TPSNRGPRNQ FITHD
```

The term "wild type LTBR-Ig" as used herein, refers to a fusion protein comprising the extracellular domain of human wild type LTBR, e.g., the extracellular domain of the LTBR sequence presented in SEQ ID NO: 1, and any immunoglobulin sequence known in the art which is not modified, for example, by mutations, deletions, etc. An exemplary wild type Ig amino acid sequence is provided in SEQ ID NO: 22. An example of a wild type LTBR-Ig fusion protein having no modifications is described in SEQ ID NO: 6.

In one aspect, the invention pertains to LTBR-Ig fusion proteins comprising a variant LTBR extracellular domain. For example, the amino acids "SQPQ" (SEQ ID NO: 26) may be deleted from the amino terminal of the wild-type LTBR protein (mature form), as shown in SEQ ID NO: 4 (amino acid sequence of the LTBR extracellular domain of LTBR06). As demonstrated in the Examples provided below, deletion of "SQPQ" (SEQ ID NO: 26) from the amino terminal of LTBR improves the overall heterogeneity within an LTBR-Ig protein population, including N-terminal heterogeneity. As described in the Examples, expression of LTBR06 provides a population of LTBR-Ig fusion proteins where at least 90% of the LT-b-R-Ig-fusion proteins are missing no more than 5 amino acids from the N-terminus of the mature form of the wild type LT-b-R extracellular domain set forth in SEQ ID NO:21. Thus, expression of LTBR06 results in a population of LTBR-Ig proteins, where 90% of the proteins are either N-4 or N-5. In addition, LTBR06 has reduced pyroglutamic acid formation.

In another embodiment, the LTBR-Ig of the invention may include a variant Ig portion having a deletion in the c-terminal amino acid of the Fc portion, i.e., "K". As described in the Examples below, the deletion of the last amino acid of an Fc portion of an LTBR-Ig fusion protein reduces C-terminal heterogeneity. An example of a variant Ig portion where the last amino acid has been deleted to improve, i.e., reduce, C-terminal heterogeneity is described in SEQ ID NO: 2. Examples of LTBR-Ig fusion proteins having variant Ig portions with a deleted last amino acid, i.e., the last lysine, are described in SEQ ID NOs: 5, 8, 9, and 12. The variant Ig portion may comprise an Fc region of an IgG isotype, including, but not limited to, an IgG1 isotype.

The invention also includes an LTBR-Ig fusion protein having both a variant LTBR extracellular domain and a variant Ig portion. LTBR06 is an LTBR-Ig fusion protein comprising a variant LTBR extracellular domain having the first four amino acids removed and a variant Ig portion, wherein the last amino acid (K) is deleted. The N-terminal and C-terminal deletions of LTBR06 reduce both N-terminal and C-terminal heterogeneity. SEQ ID NO: 8 below describes the amino acid sequence of LTBR06, including the signal sequence. Amino acids in italics in the sequence below indicate the signal sequence; underlined amino acids indicate sequence derived from the extracellular region of LTBR; and amino acids in bold indicate IgG Fc sequence.

In one embodiment, the immunoglobulin portion of an Ig fusion protein of the invention comprises at least a portion of an immunoglobulin hinge region. In one embodiment, a variant Fc portion may comprise at least one mutation in the hinge region, e.g., a mutation of the cysteine (at amino acid position 220 (Kabat numbering) also shown as amino acid position one of SEQ ID NO:22) of the Ig upper hinge to a valine. The subject valine is bolded/underlined/italicized below. The underlined sequence is a substantial part of the extracellular domain of LTBR and corresponds to amino acids 32 to 225 of SEQ ID NO:1 (above). During proteolytic processing, the signal sequence of the LTBR protein is cleaved. Thus, the final LTBR protein product for LTBR06 is described in SEQ ID NO: 5.

In addition to the valine mutation described in SEQ ID NO: 8, other suitable amino acids may be used. For example, amino acids including serine, threonine, alanine, leucine, glycine, or isoleucine may be used in place of the valine of LTBR06, and the other LTBR-Ig fusion proteins described herein.

Figure 8:
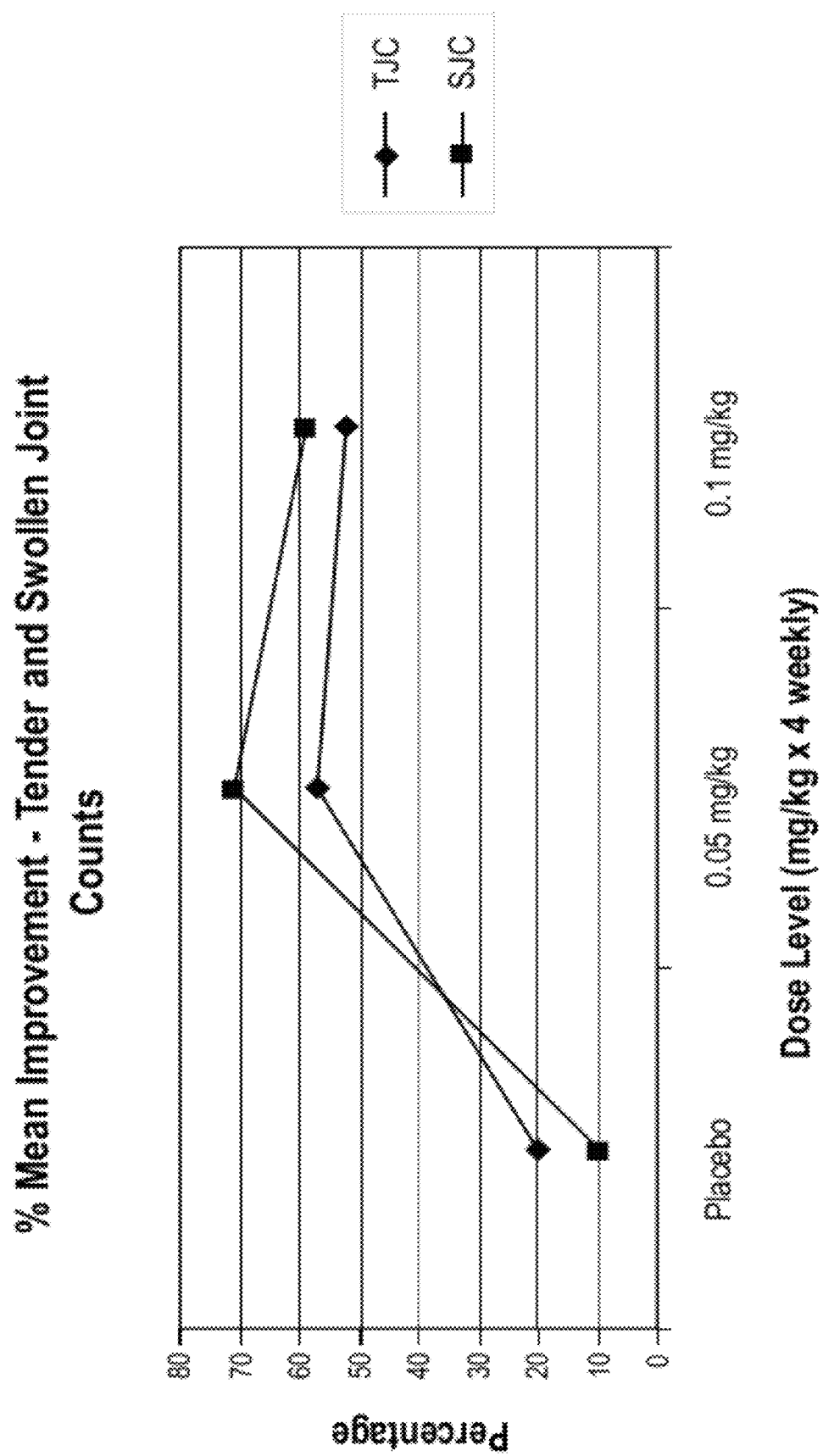
FIG. 8 is a graph depicting the percent improvement in RA symptom scores (tender joint counts (TJC) and swollen joint counts (SJC)) in patients following treatment with LTBR-Fc.

In an optional embodiment, an immunoglobulin hinge be used to link an LTBR extracellular domain to, e.g., the CH1, CH2, and CH3 domains of an immunoglobulin molecule. For example, an IgG hinge region having the sequence CDKTH-TCPPCPAPELLGGP (SEQ ID NO: 27) may be used. In one embodiment, a hinge region having the sequence VDKTH-TCPPCPAPELLGGP (SEQ ID NO: 28) may be used. Other exemplary upper and middle hinge constructs are shown in FIGS. 6 to 8, as well as SEQ ID NOs: 13 to 20. Thus, the variant Ig portion of the LTBR-Ig fusion protein may include an upper and middle hinge region comprising at least 90% to 95% identity to the hinges described in SEQ ID NOs: 13 to 20. The upper and middle hinge region set forth in SEQ ID NO: 13 was used in the variant LTBR-Ig fusion proteins exemplified herein. Accordingly, LTBR-Ig fusion proteins comprising variant hinges, e.g., those described in SEQ ID NOs: 14 to 21, would be constructed by replacing the sequence set forth in SEQ ID NO: 13 with the variant hinge. Other variant hinge molecules that can optionally be used to link an LTBR extracellular domain to, e.g., the CH1, CH2, and CH3 domains of an immunoglobulin molecule are disclosed in 20050163782A1, the contents of which are incorporated by reference herein.

When an LTBR-Ig fusion protein, such as LTBR06, is expressed, the population of proteins which results includes a variety of overall lengths due, at least in part, to N-terminal and/or C-terminal proteolysis, as well as heterogeneity of pyroglu formation. An important aspect of the invention is the discovery that by deleting the first four amino acids of the LTBR-Ig fusion protein (specifically the first four amino acids of the LTBR extracellular domain), heterogeneity can be reduced, including N-terminal heterogeneity. Thus, in one embodiment, the invention features a composition comprising a population of LTβR-Ig-fusion proteins which comprise a variant LTβ-R extracellular domain of 193 or 194 amino acids in length and a variant Ig portion of 227 amino acids in length, wherein at least 90% of the LT-β-R-Ig-fusion proteins

```
                                                          (SEQ ID NO: 8)
M L L P W A T S A P G L A W G P L V L G L F G L L A A A V P P Y A S E

N Q T C R D Q E K E Y Y E P Q H R I C C S R C P P G T Y V S A K C S R

I R D T V C A T C A E N S Y N E H W N Y L T I C Q L C R P C D P V M G

L E E I A P C T S K R K T Q C R C Q P G M F C A A W A L E C T H C E L

L S D C P P G T E A E L K D E V G K G N N H C V P C K A G H F Q N T S

S P S A R C Q P H T R C E N Q G L V E A A P G T A Q S D T T C K N P L

E P L P P E M S G T M V D K T H T C P P C P A P E L L G G P S V F L F

P P K P K D T L M I S R T P E V T C V V V D V S H E D P E V K F N W Y

V D G V E V H N A K T K P R E E Q Y N S T Y R V V S V L T V L H Q D W

L N G K E Y K C K V S N K A L P A P I E K T I S K A K G Q P R E P Q V

Y T L P P S R D E L T K N Q V S L T C L V K G F Y P S D I A V E W E S

N G Q P E N N Y K T T P P V L D S D G S F F L Y S K L T V D K S R W Q

Q G N V F S C S V M H E A L H N H Y T Q K S L S L S P G Stop
``` are missing no more than 5 amino acids from the N-terminus of the mature form of the wild type LT-β-R extracellular domain set forth in SEQ ID NO:21 and wherein the LT-β-R-Ig-fusion proteins lack pyroglutamic acid. The invention also features a composition comprising a population of LT-β-R-Ig fusion proteins comprising a variant LT-β-R extracellular domain of 193 or 194 amino acids in length and a variant Ig portion, wherein the population has reduced N-terminal pyroglutamic acid formation, and reduced C-terminal heterogeneity compared to wild-type LT-β-R-Ig fusion proteins.

The amino terminal amino acid of the variant LTBR-Ig fusion protein may be an alanine, as set forth in SEQ ID NOs: 5 and 12, or, alternatively, may be a non-polar amino acid. Examples of non polar amino acids which may be used as the first amino acid of the LTBR-Ig fusion protein include a valine (amino acid six of the mature form of the wild type LT-β-R portion SEQ ID NO:1) or an alanine (amino acid five of the mature form of the wild type LT-β-R portion SEQ ID NO:1). In addition, to non-polar amino acids, serine or threonine may be used. In one embodiment, the composition of the invention includes a population of LTBR-Ig fusion proteins whereby the N-terminus of at least 95% of the LT-β-R-Ig-fusion proteins is either a valine (amino acid six of the mature form of wild type LT-β-R) or an alanine (amino acid five of the mature form of wild type LT-β-R).

In addition to N- and/or C-terminal heterogeneity, heterogeneity may also result from variable glycosylation. In order to minimize heterogeneity resulting from glycosylation variations within a protein population of LTBR-Ig fusion proteins, the LTBR and/or the Ig may be altered to reduce the amount of glycosylation. In one embodiment, the Ig portion of the LTBR-Ig fusion protein is non-glycosylated.

The invention also contemplates a composition comprising a population of LTβR-Ig fusion proteins comprising a variant LT-β-R extracellular domain and a variant Ig portion, wherein variant LT-β-R extracellular domain is aglycosylated. An example of an aglycosylated extracellular domain of LTBR is provided in the Examples, and is also described in SEQ ID NO: 10 (see amino acids 1 to 194 of SEQ ID NO: 10).

Thus, examples of post-translational heterogeneity that may be decreased using the methods and compositions described herein include N-terminal heterogeneity, C-terminal heterogeneity, and glycosylation heterogeneity. It is within the scope of the invention to provide LTBR-Ig fusion proteins having reduced heterogeneity in each of these parameters, as well as combinations thereof. For example, the invention includes compositions comprising a population of LT-β-R-Ig fusion proteins, wherein the population has reduced N-terminal heterogeneity and reduced C-terminal heterogeneity, compared to a population of wild-type LT-β-R-Ig fusion proteins.

Methods of treating autoimmune disorders using the above compositions and LTBR-Ig fusion proteins, as well as pharmaceutical compositions comprising the same, are described in more detail in sections II and III below.

An LTBR-Ig fusion polypeptide of the invention retains the ligand binding activity of LTBR, and includes those polypeptides which have an amino acid sequence that has at least 70% homology to the LTBR-Ig polypeptides set forth in SEQ ID NOs: 5, 6, 8, 9, 10, 11, 12, and 23 and variants and derivatives of each of the foregoing. The invention also includes isolated polypeptides described in SEQ ID NOs: 3, 4, and 7, which provide either LTBR extracellular domains of the invention or Ig variants of the invention. Preferably the LTBR-Ig polypeptide (or portion thereof) has an amino acid sequence greater than 85% homology, more preferably greater than 90% homology, more preferably greater than 95% homology, most preferably greater than 99% homology, to the foregoing sequences.

In one embodiment, the invention features an isolated polypeptide comprising an amino acid sequence which is at least 90% identical to the full length of the mature form of SEQ ID NO:8 or SEQ ID NO:23, wherein the amino acid sequence of the ligand binding domain is unchanged, the polypeptide further comprising a truncated Fc region. In one embodiment, the polypeptide of the invention comprises an amino acid sequence is at least 95% identical to the full length of the mature form of the polypeptide set forth in SEQ ID NO: 8. In one embodiment, the polypeptide of the invention comprises an amino acid sequence of the mature form of the polypeptide set forth in SEQ ID NO: 8. In one embodiment, the polypeptide of the invention comprises the amino acid sequence set forth in SEQ ID NO: 5.

Variants of the polypeptides described herein are also contemplated by the invention. Thus, variants of the polypeptide having an amino acid sequence that differs from the sequence presented in SEQ ID NO: 5, SEQ ID NO: 6, SEQ ID NO: 8, SEQ ID NO: 9, SEQ ID NO: 10, SEQ ID NO: 11, SEQ ID NO: 12, and SEQ ID NO: 23, as well as portions thereof described in SEQ ID NO: 3, SEQ ID NO: 4, and SEQ ID NO: 7, at one or more amino acid positions, are included in the invention. Such variant polypeptides include the modified polypeptides described above, as well as conservative substitutions, splice variants, isoforms, homologues from other species, and polymorphisms. the Modifications of an LTBR-Ig primary amino acid sequence may result in proteins which have substantially equivalent activity as compared to the unmodified counterpart polypeptide, and thus may be considered functional analogous of the parent proteins. Such modifications may be deliberate, e.g. as by site-directed mutagenesis, or they may occur spontaneous, and include splice variants, isoforms, homologues from other species, and polymorphisms. Such functional analogs are also contemplated according to the invention.

Moreover, modifications of the primary amino acid sequence may result in proteins which do not retain the biological activity of the parent protein, including dominant negative forms, etc. A dominant negative protein may interfere with the wild-type protein by binding to, or otherwise sequestering regulating agents, such as upstream or downstream components, that normally interact functionally with the polypeptide. Such dominant negative forms are also contemplated according to the invention.

The LTBR-Ig proteins of the invention may be made according to standard methods known in the art. A nucleic acid molecule encoding LTBR-Ig may be used to express a LTBR-Ig polypeptide, e.g., by expressing a LTBR-Ig polypeptide in vivo, or by administering a nucleic acid molecule encoding LTBR-Ig to an animal for in vivo expression. Nucleic acid molecules encoding LTBR-Ig may be included within a nucleic acid vector, e.g., an expression vector or a cloning vector. A nucleic acid molecule encoding a LTBR-Ig may, but need not of necessity, be maintained, reproduced, transferred, or expressed as part of a nucleic acid vector. Thus, another aspect of the invention is isolated nucleic acid molecules which encode the LTBR-Ig proteins of the invention described herein. The invention includes a nucleic acid molecule comprising the nucleotide sequence set forth in SEQ ID NO:7 (mature form of LTBR06).

A recombinant expression vector containing a LTBR-Ig polynucleotide sequence can be introduced into and/or maintained within a cell. Cells hosting a LTBR-Ig vector may be prokaryotic. Alternatively, a LTBR-Ig nucleic acid can be introduced into a eukaryotic cell, e.g., a eukaryotic cell that contains the appropriate apparati for post-translational processing of a polypeptide into a mature protein, and/or the appropriate apparati for secreting a polypeptide into the extracellular environment of the cell. Also encompassed within the scope of the invention are vectors comprising nucleic acid molecules encoding the LTBR-Ig fusion proteins of the invention.

Suitable methods of making LTBR-Ig proteins of the invention are known in the art and are described, for example, in WO 97/03687, WO 98/17313, WO 00/21558, WO 99/38525, WO 00/36092. For example, an LTBR immunoglobulin fusion protein can be expressed in cell culture (e.g., mammalian cell culture (such as monkey cos cells or Chinese hamster ovary cells) or yeast cell culture) at a reduced temperature, e.g, to produce an increased amount of properly folded fusion protein. Also included within the scope of the invention are host cells expressing LTBR-Ig fusions proteins of the invention, where the host cell comprises a vector comprising a nucleic acid encoding an LTBR-Ig fusion protein. In one embodiment, the host cell is a Chinese Hamster Ovary (CHO) cell. The expressed fusion protein can be purified, e.g., by affinity or conventional chromatography techniques. See WO 00/36092. Expression of the LTBR-Ig fusion protein may range in scale, including manufacturing scale.

The invention further provides a process for making a composition comprising a population of LTβR-Ig-fusion proteins which comprise a variant LT-β-R extracellular domain and a variant Ig portion, wherein at least 90% of the LTβR-Ig-fusion proteins are missing no more than 5 amino acids from the N-terminus of the mature form of the wild type LT-β-R portion set forth in SEQ ID NO:1, the process comprising, expressing a nucleic acid molecule encoding the LT-β-R-Ig fusion protein set forth in SEQ ID NO:8 in a mammalian cell, obtaining the population from the culture supernatant, and, optionally, purifying the supernatant, to thereby obtain a composition comprising a population of LTβR-Ig-fusion proteins which comprise a variant LT-β-R extracellular domain and a variant Ig portion, wherein at least 90% of the LT-β-R-Ig-fusion proteins are missing no more than 5 amino acids from the N-terminus of the mature form of the wild type LT-β-R portion set forth in SEQ ID NO:1. In one embodiment, the process comprises expressing a nucleic acid molecule set forth in SEQ ID NO:7 in a mammalian cell. In one embodiment, the process comprises expressing a nucleic acid molecule set forth in SEQ ID NO:7 in a mammalian cell. The invention also features expressing a nucleic acid molecule comprising a nucleotide sequence encoding the extracellular domain of LTBR set forth in SEQ ID NO:4, or the nucleic acid sequence set forth in SEQ ID NO: 3 in a mammalian cell. The invention further features a composition which is made by expressing a nucleic acid molecule encoding the LT-β-R-Ig fusion protein set forth in SEQ ID NO:8, or the nucleic acid sequence set forth in SEQ ID NO: 7, in a mammalian cell.

II. Uses of LTBR-IgG of Invention for Treating Autoimmune Disorders

Soluble LTBRs are lymphotoxin (LT) pathway inhibitors useful for treating autoimmune disorders. Autoimmune disorders include, for example, autoimmune arthritides (including rheumatoid arthritis (RA) and Sjögren's syndrome) psoriasis, multiple sclerosis, inflammatory bowel disease (IBD) (including ulcerative colitis and Crohn's disease), insulin-dependent diabetes, uveitis, systemic lupus erythematosus (SLE, or lupus), polychondritis, and transplant rejection. The agents and methods described herein are particularly suitable for treatment of RA.

Rheumatoid arthritis is marked by tenderness in the joints. Synovial thickening eventually occurs in most effected joints. Stiffness lasting >30 minutes upon arising in the morning or after prolonged inactivity is common, as is early afternoon fatigue and malaise. Deformities, particularly flexion contractures may develop rapidly. Carpal tunnel syndrome can result from wrist synovitis. X-rays may reveal soft-tissue swelling in the first months of disease, and subsequently, perarticular osteoporosis, joint space narrowing, and marginal erosions may be present.

Various tests can be employed to assay the efficacy of a soluble LTBR to treat autoimmune disorders. In the case of rheumatoid arthritis (RA), for example, insufficient efficacy may be defined as failure to exhibit at least a 10%, 20%, 25%, 30%, 40%, 50% or more decrease in a clinical parameter of RA, such as tender joint count (TJC), swollen joint count (SJC), patient global assessment of disease activity [PGA visual analogue scale (VAS) 0-10 cm, for measurement of pain], physician global assessment of disease activity (MDGA VAS 0-10 cm), levels of C-reactive protein (CRP in mg/dl), and erythrocyte sedimentation rate (ESR). C-reactive protein is produced by the liver during episodes of acute inflammation or infection. CRP levels in blood serum are an indicator of the severity of RA. A decrease in CRP levels, such as by 5%, 10%, 15%, 20%, or more, can be an indication of effective treatment of autoimmune disorder, such as RA, in response to treatment with a soluble LTBR, such as LTBR-Fc. Erythrocyte sedimentation rate (ESR) is also elevated in 90% of RA cases. Thus a decrease in ESR following treatment with a soluble LTBR can also be an indication of effective treatment.

The high potency of the soluble LTBR demonstrated herein indicates that low dosage regimes would be equally effective for treatment of other autoimmune conditions. Autoimmune conditions suitable for treatment as described herein with a soluble LTBR, e.g., an LTBR-Fc, include, e.g., autoimmune arthritides (including rheumatoid arthritis and Sjögren's syndrome), psoriasis, multiple sclerosis, inflammatory bowel disease (IBD) (including ulcerative colitis and Crohn's disease), insulin-dependent diabetes, uveitis, systemic lupus erythematosus (SLE, or lupus), polychondritis, and transplant rejection.

Exemplary Dosing Regimens

The invention is based, in part, on the discovery that low dosage or frequency regimens of a soluble form of LTBR (e.g., LTBR-Fc) can effectively treat symptoms of an autoimmune disorder, and rheumatoid arthritis (RA) in particular. Accordingly, in one aspect, the invention provides methods of treating autoimmune disease in a subject. The method includes administering to the subject an LTBR blocking agent (e.g., a soluble LTBR fusion protein, e.g., LTBR-Fc) at a low dose and/or frequency.

Figure 14:
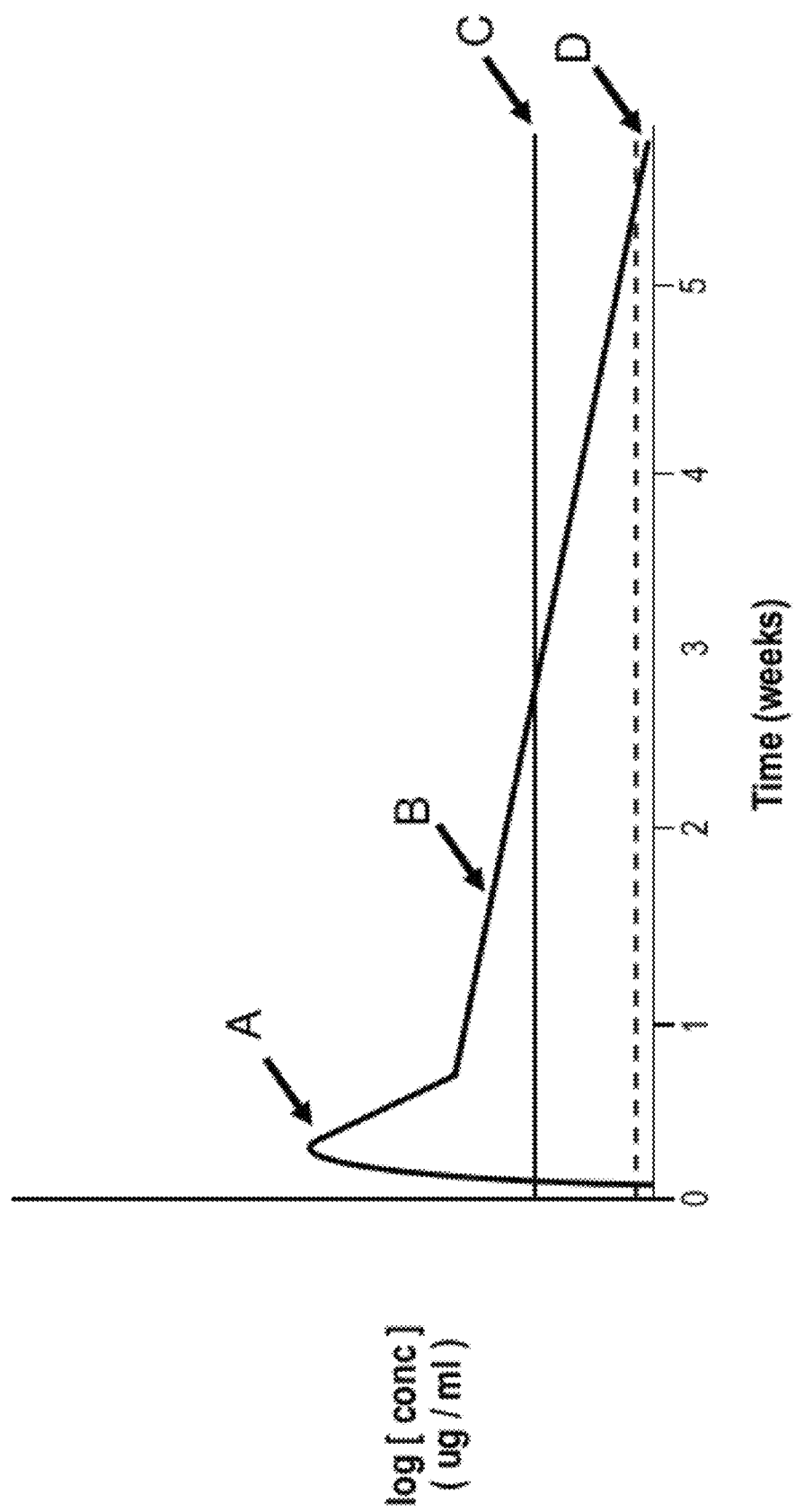
FIG. 14 illustrates a comparison of LTBR-Fc and a typical antibody and shows that at identical dosing significant differences in efficacy are observed for prolonged time frames. Arrows A and B indicate the typical alpha and beta phases for an antibody or Fc-fusion protein, respectively. For an antibody the gray line indicated by arrow C shows typical lower limit concentration for efficacy, whereas arrow D shows LTBR-Fc has efficacy at significantly lower concentrations.

As shown in FIG. 14, comparisons of LTBR-Fc and a typical antibody, show that at identical dosing significant differences in efficacy are observed for prolonged time frames. This results because LTBR-Fc has high affinity for the target ligand, in addition to antibody like pharmacokinetics and is therefore effective at very low doses. Arrows A and B indicate the typical alpha and beta phases for an antibody or Fc-fusion protein, respectively. For an antibody the gray line indicated by arrow C shows typical lower limit concentration for efficacy, whereas arrow D shows LTBR-Fc has efficacy at significantly lower concentrations.

In one embodiment, a soluble LTBR fusion protein is administered to achieve an average concentration of between about 0.14 ug/ml to about 3.5 ug/ml. In one embodiment, a soluble LTBR fusion protein is administered to achieve a minimal average concentration of about 0.3 to about 1.0 ug/m., e.g., of about 0.6 to 0.7 ug/ml. In another embodiment, higher doses of the fusion protein may be administered. For example, the fusion protein may be administered to achieve an average concentration of between about 5 and 15 ug/ml.

In another embodiment, a soluble LTBR fusion protein is administered at a dose of between about 70 and about 200 mg/month to an average subject weighing about 75 kg. In another embodiment, a soluble LTBR fusion protein is administered at a dose of about 100, about 150, or about 175 mg/month to an average subject weighing about 75 kg.

Embodiments of the invention can include administration of a regimen of LTBR blocking agent, e.g., a soluble LTBR, such as an LTBR fusion protein (e.g., LTBR-Ig), for the treatment of autoimmune arthritides (including rheumatoid arthritis and Sjögren's syndrome), psoriasis, multiple sclerosis, inflammatory bowel disease (IBD) (including ulcerative colitis and Crohn's disease), insulin-dependent diabetes, uveitis, systemic lupus erythematosus (SLE, or lupus), polychondritis, and transplant rejection.

In one embodiment, the subject is treated with a soluble LTBR, e.g., an LTBR immunoglobulin fusion. Exemplary LTBR-Ig fusion proteins are described herein.

In one embodiment, the subject has one or more symptoms of RA, e.g., joint swelling, joint pain, joint stiffness, or difficulty moving. For example, the subject has active RA disease (e.g., tender joint count (TJC) or swollen joint count (SJC)≧5 or synovitis). In another embodiment, the subject is at risk for developing RA, e.g., a family history, or an autoimmune disease.

In one embodiment, the soluble LTBR can be administered in an amount and/or for a time sufficient to alleviate the symptoms associated with RA.

In another embodiment, the soluble LTBR, e.g., an LTBR-Fc, is administered in an amount sufficient to improve symptoms in one or more RA assessment criterion, e.g., a criterion described herein. For example, the soluble LTBR is administered in an amount sufficient to improve symptom scores at least about 10%, 20%, 25%, 30%, 40%, 50% or more. Symptom scores refer, for example, to TJC, SJC, patient global assessment of disease activity [PGA visual analog scale (VAS) 0-10 cm], physician global assessment of disease activity (MDGA VAS 0-10 cm) quantities of C-reactive protein (CRP in mg/dl), or Disease Activity Score, 28-joint version (DAS28). Symptom scores can be reported according to criteria set forth by the American College of Rheumatology (ACR). An ACR score is an indication of the percent clinical improvement in RA symptoms. For example, an ACR20 is an indication of a 20% clinical improvement in TJC and SJC, as well as a 20% improvement in three of the following five parameters: (i) patient's global assessment, (ii) physician's global assessment, (iii) patient's assessment of pain, (iv) degree of disability, and (v) level of acute-phase reactant. ACR scores of ACR50 and ACR70 can also be used to indicate a 50% improvement, or a 70% improvement, respectively.

In one embodiment, the soluble LTBR, e.g., LTBR-Fc, is administered more than once, e.g., weekly, biweekly, or monthly. The course of treatment can be maintained for a period of time, such as for 1 or 2 weeks or more; 1, 2, 3, 4, 5, or 6 months or more; 1 year; or longer. In certain embodiments, the soluble LTBR is administered at a dosage of about 0.03 to 3 mg/kg of body weight per administration, e.g., about 0.6 to about 1.4 mg/kg per administration. In another embodiment, the soluble LTBR is administered at a dosage of about 0.3-3, e.g., 1 mg/kg of body weight per administration, e.g., about 0.6 to about 1.4 mg/kg per administration. In other embodiments, the soluble LTBR is administered at a dosage of about 2.5 to 3.5 mg/kg of body weight per administration, e.g., about 2.8 to 3 mg/kg per administration. In yet other embodiments, the soluble LTBR is administered at a dosage of about 0.01 to 3 mg/kg of body weight per administration, e.g., about 0.01 to about 0.05 mg/kg per administration, about 0.01 to about 0.3 mg/kg per administration, about 0.01 to 0.2 mg/kg per administration, or about 0.01 to about 0.1 mg/kg per administration. In some embodiments, the soluble LTBR is administered at about 0.03 mg/kg per administration, about 0.05 mg/kg per administration, about 0.07 mg/kg per administration, about 0.1 mg/kg per administration, or about 0.2 mg/kg per administration. In some embodiments, the soluble LTBR is administered at a dosage shown in Table 1.

TABLE 1

Exemplary dosages of LTBR-Fc (mg per kg of body weight of subject per administration)

| Weekly dosage | Biweekly Dose | Monthly Dose |
| --- | --- | --- |
| 0.01-0.3; | 0.01-0.3; | 0.3-3; |
| 0.011-0.29; | 0.011-0.29; | 0.3-3.5 |
| 0.011-0.25; | 0.011-0.25; | |
| 0.011-0.2; | 0.011-0.2; | |
| 0.02-0.05 | 0.02-0.05 | |
| 0.3-3.5 | 0.3-3.5 | |
| 0.01; | 0.01; | 0.29; |
| 0.011; | 0.011; | 0.3; |
| 0.02; | 0.02; | 0.5; |
| 0.03; | 0.03; | 0.6; |
| 0.04; | 0.04; | 0.7; |
| 0.05; | 0.05; | 0.8; |
| 0.06; | 0.06; | 1; |
| 0.1; | 0.1; | 1.4; |
| 0.2; | 0.2; | 2; |
| 0.29; | 0.29; | 2.5; |
| 0.3; | 0.3; | 3; |
| 0.4; | 0.4; | 3.5 |
| 0.5; | 0.5; | |
| 0.6; | 0.6; | |
| 1; | 0.7; | |
| 1.4; | 1; | |
| 2; | 1.4; | |
| 2.5; | 2; | |
| 3; | 2.5; | |
| 3.5 | 3; | |
| | 3.5 | |

Generally, the lower unit doses disclosed herein can be administered with more frequent dosing (e.g., weekly) while higher unit doses disclosed herein (though still low by relative standards) can be administered with more infrequent dosing (e.g., monthly). In some embodiments, the soluble LTBR, e.g., LTBR-Fc, is administered at a dosage of about 0.3 mg/kg per administration to about 3 mg/kg per administration, e.g., about 0.6 mg/kg per day to about 1.4 mg/kg per day. For example, the dose is about 1 mg/kg, or about 3 mg/kg. In some embodiments, the dose is administered once every 14-20 days, once or twice monthly, e.g., once or twice every 28-31 days. For example, the dose is about 1 mg/kg or about 3 mg/kg administered every 14 to 20 days, e.g., every 12 to 16 days, or about every two weeks. Alternatively, the dose is about 1 mg/kg or about 3 mg/kg administered monthly, e.g., about every 28 to 31 days.

In other embodiments, the soluble LTBR, e.g., LTBR-Fc, is administered at a dosage of about 0.6 mg/kg per administration to about 1.4 mg/kg per administration not more than twice every 20 to 40 days, e.g., not more than twice every 25 to 35 days, or not more than twice every 28-31 days. In other embodiments, the soluble LTBR, e.g., LTBR-Fc, is administered at a dosage of about 2.5 mg/kg per administration to about 3.5 mg/kg per administration not more than twice every 20 to 40 days, e.g., not more than twice every 25 to 35 days, or not more than twice every 28-31 days.

In yet other embodiments, the soluble LTBR, e.g., LTBR-Fc, is administered at a dosage of about 0.01 mg/kg per administration to about 0.3 mg/kg per administration, e.g., about 0.01 mg/kg per day to about 0.25 mg/kg per day, e.g., weekly, or every 3 to 10 days, repeated at least twice. For example, the soluble LTBR is administered at a dosage of about 0.02, 0.03, 0.04, 0.05, 0.06, 0.1, or 0.2 mg/kg, administered weekly or every 3-10 days, e.g., every 4, 5, 6, 7, 8, or 9 days. In some embodiments, the soluble LTBR is administered at a dosage shown in Table 1.

In another embodiment, the soluble LTBR is administered at a dosage of about 0.01 mg/kg per day to about 0.3 mg/kg per day, e.g., 0.02 mg/kg per day to about 0.25 mg/kg per day, e.g., biweekly, or every 5 to 20 days, repeated at least twice. For example, the soluble LTBR is administered at a dosage of about 0.03, 0.05, 0.08, 0.1, or 0.2 mg/kg, administered biweekly, or every 5-20 days, e.g., every 6, 8, 10, 12, 14, 16 or 18 days. In some embodiments, the soluble LTBR is administered at a dosage shown in Table 1.

In another embodiment, the soluble LTBR is administered at a dosage of about 0.3 mg/kg per day to about 3 mg/kg per day, e.g., 1 mg/kg per day, e.g., biweekly, or every 5 to 20 days, repeated at least twice. In some embodiments, the soluble LTBR is administered at a dosage shown in Table 1.

In another embodiment, the soluble LTBR is administered at a dosage of about 0.3 mg/kg per day to about 3 mg/kg per day, e.g., 0.4 mg/kg per day to about 3 mg/kg per day, e.g., monthly, or every 15 to 45 days, repeated at least twice. For example, the soluble LTBR is administered at a dosage of about 0.5, 0.8, 1, 1.5, or 2 mg/kg, administered monthly, or every 15-45 days, e.g., every 16, 18, 20, 25, 30, 35 or 40 days. In some embodiments, the soluble LTBR is administered at a dosage shown in Table 1.

In certain embodiments, the dose of soluble LTBR, e.g., LTBR-Fc, is about 0.4 mg to about 375 mg, about 0.4 mg to about 6.25 mg, about 2 mg to about 6.25 mg, or about 4 mg to about 12.5 mg.

In certain embodiments, the invention provides for the administration of a particularly low dose of a soluble LTBR, e.g., an LTBR-Fc, for treatment of an autoimmune disorder, e.g., RA.

In certain embodiments, the soluble LTBR is administered intravenously or parenterally, e.g., subcutaneously or intramuscularly.

In another embodiment, the soluble LTBR is administered as a monotherapy.

In one aspect, the invention provides methods of treating an autoimmune condition, e.g., RA, in a subject, such as a human. The method includes administering to the human a dose of a soluble LTBR, e.g., LTBR-Fc, wherein the dose is between about 0.01 mg and about 3 mg LTBR-Fc per kg body weight of the human (mg/kg), e.g., between about 0.01 mg/kg and about 0.05 mg/kg. In one embodiment, the human is administered a weekly dose of a soluble LTBR, e.g., LTBR-Fc, over the course of at least two weeks, where the dose is about 0.01 mg/kg per day to about 0.3 mg/kg per day, e.g., about 0.01 mg/kg per day to about 0.25 mg/kg per day, administered weekly, e.g., every 3 to 10 days. For example, the soluble LTBR is administered at a dosage of about 0.02, 0.03, 0.04, 0.05, 0.06, 0.1, or 0.2 mg/kg per day, e.g., every 4, 5, 6, 7, 8, or 9 days. In some embodiments, the soluble LTBR is administered at a dosage shown in Table 1.

In another embodiment, the human is administered a biweekly dose of a soluble LTBR, e.g., LTBR-Fc, over the course of at least four weeks, where the dose is about 0.01 mg/kg per day to about 0.5 mg/kg per day, e.g., about 0.01 mg/kg per day to about 0.3 mg/kg per day repeated every 5 to 20 days. For example, the soluble LTBR is administered at a dosage of about 0.03, 0.05, 0.08, 0.1, 0.2, 0.3 or 0.4 mg/kg, e.g., every 6, 8, 10, 12, 14, 16 or 18 days. In some embodiments, the soluble LTBR is administered at a dosage shown in Table 1.

In another embodiment, the human is administered a monthly dose of a soluble LTBR, e.g., LTBR-Fc, over the course of at least two months, where the dose is about 0.1 mg to about 3 mg soluble LTBR per kg body weight of the human per day. In one embodiment, the dose is about 0.3 mg/kg per day to about 3 mg/kg administered monthly, e.g., every 15 to 45 days. For example, the soluble LTBR is administered at a dosage of about 0.5, 0.8, 1, 1.5, or 2 mg/kg per day, e.g., every 16, 18, 20, 25, 30, 35 or 40 days. In some embodiments, the soluble LTBR is administered at a dosage shown in Table 1.

In some embodiments, a patient exhibiting an inadequate response to a therapy has not shown a clinically acceptable or significant improvement in response to the therapy. In other embodiments, the patient initially showed an improvement in response to a therapy but no longer demonstrates an improvement, as assessed by a standard clinical measure for the specific disorder. A DMARD-IR subject is a subject who has had an inadequate response to a disease modifying antirheumatic drug (DMARD), such as methotrexate, leflunomide (Arava®), anakinra (Kineret®), hydroxycholoquine sulfate (Plaquenil®) antimalarials, gold salts, sulfasalazine (Azulfidine®), minocycline (Minocin®), d-penicillamine, cyclosporin A, cyclosporine (Neoral®), cyclophosphamide and azathioprine (Imuran®).

In one aspect, the invention features a delivery device, e.g., a transcutaneous delivery device, e.g., a syringe, designed for subcutaneous or intramuscular administration, where the device is packaged with or contains at least one unit dose of a soluble LTBR, e.g., LTBR-Fc, such that an appropriately low quantity of the agent will be administered to a human. In one embodiment, the device contains or is packaged with a unit dose of LTBR-Fc such that administration to a human will deliver between about 0.01 mg/kg and 3 mg/kg LTBR-Fc, e.g., about 0.01 to about 0.05 mg/kg LTBR-Fc, or about 0.6 mg/kg and 1.4 mg/kg LTBR-Fc, to the human. In another embodiment, the device contains or is packaged with a unit dose of LTBR-Fc such that administration to a human will deliver between about 2.5 mg/kg and 3.5 mg/kg LTBR-Fc to the human. In certain embodiments the delivery device will deliver about 1 mg/kg or about 3 mg/kg LTBR-Fc to the human. Exemplary unit dose amounts appropriate for humans of various weights is provided in Table 2.

In one embodiment, the liquid in the second compartment is water or a buffer. The liquid can include, e.g., a pharmaceutically acceptable carrier, such as a solvent, dispersion media, antibacterial or antifungal agent, or isotonic or absorption-delaying agent. The liquid may also include a pharmaceutically acceptable salt.

TABLE 2

Exemplary dose of LTBR-Fc (mg) according to weight of human

| Final concentration[a]: | Weight of human: | | | | |
|---|---|---|---|---|---|
| | 40-50 kg | 50-60 kg | 60-75 kg | 75-100 kg | 100-125 kg |
| 0.01 mg/kg | 0.4-0.5 | 0.5-0.6 | 0.6-0.75 | 0.75-1.0 | 1.0-1.25 |
| 0.02 mg/kg | 0.8-1.0 | 1.0-1.2 | 1.2-1.5 | 1.5-2.0 | 2.0-2.5 |
| 0.03 mg/kg | 1.2-1.5 | 1.5-1.8 | 1.8-2.25 | 2.25-3.0 | 3.0-3.75 |
| 0.05 mg/kg | 2-2.5 | 2.5-3 | 3-3.75 | 3.75-5.0 | 5.0-6.25 |
| 0.1 mg/kg | 4-5 | 5-6 | 6-7.5 | 7.5-10 | 10-12.5 |
| 0.2 mg/kg | 8-10 | 10-12 | 12-15 | 15-20 | 20-25 |
| 0.3 mg/kg | 12-15 | 15-18 | 18-22.5 | 22.5-30 | 30-37.5 |
| 0.5 mg/kg | 20-25 | 25-30 | 30-37.5 | 37.5-50 | 50-62.5 |
| 0.7 mg/kg | 28-35 | 35-42 | 42-52.5 | 52.5-70 | 70-87.5 |
| 1.0 mg/kg | 40-50 | 50-60 | 60-75 | 75-100 | 100-125 |
| 1.5 mg/kg | 60-75 | 75-90 | 90-112.5 | 112.5-150 | 150-187.5 |
| 2.0 mg/kg | 80-100 | 100-120 | 120-150 | 150-200 | 200-250 |
| 2.5 mg/kg | 100-125 | 125-150 | 150-187.5 | 187.5-250 | 250-312.5 |
| 3.0 mg/kg | 120-150 | 150-180 | 180-225 | 225-300 | 300-375 |
| 3.5 mg/kg | 140-175 | 175-210 | 210-262.5 | 262.5-350 | 350-437.5 |

[a] mg LTBR-Fc per kg of body weight of human

In certain embodiments, the unit dose of the soluble LTBR, e.g., LTBR-Fc included in a delivery device is about 0.4 mg to about 375 mg, about 0.4 mg to about 6.25 mg, about 2 mg to about 6.25 mg, or about 4 mg to about 12.5 mg. In one embodiment, the device contains lyophilized LTBR-Fc.

In one aspect, the invention features a kit including two or more unit doses of between about 0.4 mg to about 375 mg LTBR-Fc. The unit doses are such that an appropriately low quantity will be administered to a human, as determined by the weight of the human. Exemplary unit dose amounts appropriate for humans of various weights is provided in Table 2.

In another aspect, the invention features a device, e.g., a transcutaneous delivery device, e.g., a syringe having at least two compartments, where a first compartment contains a unit dose of lyophilized LTBR-Fc and a second compartment contains a liquid for reconstituting the LTBR-Fc prior to administration to a subject. For example, the unit dose is such that administration of the LTBR-Fc will deliver between about 0.01 to 3 mg/kg, e.g., 1.0 mg/kg LTBR-Fc to the human. For example, in some embodiments, the unit dose of LTBR-Fc is between about 0.4 mg and about 375 mg LTBR-Fc, e.g., between about 0.4 mg and about 6.25 mg LTBR-Fc. The unit doses are such that an appropriately low quantity will be administered to a human, as determined by the weight of the human. Exemplary unit dose amounts appropriate for humans of various weights is provided in Table 2.

In another aspect, the invention features a method of instructing a patient having rheumatoid arthritis to treat the RA by (i) providing the patient with at least two unit doses of LTBR-Fc; and (ii) instructing the patient to self-administer the unit doses, e.g., subcutaneously, one dose at a time. In certain embodiments, the dose delivered will be between about 0.01 mg and 3 mg LTBR-Fc per kg of body weight of the patient (mg/kg), e.g., between about 0.6 mg/kg and 1.4 mg/kg, or about 0.01 mg/kg and 0.05 mg/kg. In one embodiment, the dose delivered will be between about 2.5 to 3.5 mg/kg LTBR-Fc per kg of body weight of the patient (mg/kg). In certain embodiments, the patient is instructed to self-administer the doses weekly, over the course of at least 2 weeks; biweekly, over the course of at least 4 weeks; or monthly, over the course of at least 2 months. In certain embodiments, the unit dose is about 0.01 to about 3.0 mg/kg LTBR-Fc per administration. In certain embodiments, the unit dose is about 0.01 to about 2.5 mg/kg per administration, about 0.02 to about 0.5 mg/kg per administration, about 0.01 to about 0.3 mg/kg per administration, about 0.01 to about 0.2 mg/kg per administration, about 0.01 to about 0.1 mg/kg per administration, or about 0.01 to about 0.05 mg/kg per administration. In certain embodiments, the unit dose is about 0.03 mg/kg, about 0.05 mg/kg, about 0.07 mg/kg, about 0.1 mg/kg, or about 0.2 mg/kg per administration.

In one embodiment, the patient is instructed to self-administer the doses weekly, over the course of at least 2 weeks, where the unit dose is about 0.01 mg/kg to about 3.0 mg/kg LTBR-Fc per administration, e.g., about 0.01 mg/kg to about 0.25 mg/kg, about 0.01 mg/kg to about 0.05 mg/kg LTBR-Fc per administration. For example, the unit dose is about 0.02, 0.03, 0.04, 0.05, 0.06, 0.1, or 0.2 mg/kg per administration.

In one embodiment, the patient is instructed to self-administer the doses biweekly, over the course of at least 4 weeks, where the unit dose is between about 0.01 and 1.5 mg/kg, e.g., about 0.01 to about 0.3, or about 0.02 mg/kg to about 0.3 mg/kg or about 0.5-1.25 mg/kg LTBR-Fc. For example, the unit dose is about 0.03, 0.05, 0.08, 0.1, 0.2, 0.3, 0.4, 0.5, 0.75, or 1.0 mg/kg per administration.

In one embodiment, the patient is instructed to self-administer the doses monthly, over the course of at least 2 months, where the unit dose is between about 0.03 to about 3 mg LTBR-Fc per kg of body weight of the patient (mg/kg). For example, the unit dose is about 0.2, 0.5, 0.8, 1, 1.5, or 2 mg/kg.

In another aspect, the invention features a method of managing RA in a patient including (i) instructing a patient to stop taking a therapy to treat RA, and (ii) administering to the patient a unit dose of LTBR-Fc. In one embodiment, the unit dose is between about 0.03 to about 3 mg/kg LTBR-Fc, e.g., about 0.6 to about 1.4 mg/kg LTBR-Fc. In another embodiment, the unit dose is about 2.5 to about 3.5 mg/kg LTBR-Fc. In other embodiments, the unit dose is between about 0.01 to about 0.05 mg/kg LTBR-Fc.

In another embodiment, the unit dose is between about 0.3 mg/kg and 3 mg/kg LTBR-Fc, and the unit dose is administered not more than twice every 20-40 days, e.g., every 25-35 days, or 28-31 days. In another embodiment, the unit dose is between about 0.6 mg/kg and about 1.4 mg/kg LTBR-Fc, administered not more than twice every 20-40 days, e.g., every 25-25 days, or every 28-31 days.

In another embodiment, the unit dose is between about 0.01 mg/kg and 0.3 mg/kg LTBR-Fc, and the unit dose is administered not more than once every 3-10 days, e.g., weekly. In another embodiment, the unit dose is between about 0.01 mg/kg and about 0.3 mg/kg LTBR-Fc administered not more than once every 5-20 days, e.g., biweekly. In another embodiment, the unit dose is between about 0.3 mg/kg and about 3 mg/kg LTBR-Fc administered not more than once every 28-31 days, e.g., monthly.

In one embodiment, the unit dose is about 0.01 mg/kg to about 0.25 mg/kg LTBR-Fc, and the unit dose is administered weekly over the course of at least 2 weeks. For example, the unit dose is about 0.02, 0.03, 0.04, 0.05, 0.06, 0.1, or 0.2 mg/kg per administration.

In another embodiment, the unit dose is about 0.02 mg/kg to about 0.5 mg/kg LTBR-Fc, and the unit dose is administered biweekly over the course of at least 4 weeks. For example, the unit dose is about 0.03, 0.05, 0.08, 0.1, 0.2, 0.3 or 0.4 mg/kg per administration.

In another embodiment, the unit dose is about 0.03 to about 3 mg LTBR-Fc, and the unit dose is administered monthly over the course of at least 2 months. For example, the unit dose is about 0.2, 0.5, 0.8, 1, 1.5, or 2 mg/kg per administration.

In one embodiment, the patient is instructed to stop an NSAID, corticosteroid, or DMARD therapy.

In one aspect, the invention features a method of managing RA in a patient that includes administering to the patient a unit dose of a soluble LTBR, e.g., LTBR-Fc, where (i) the unit dose is between about 0.01 mg and about 0.05 mg of the soluble LTBR per kg of body weight of the patient (mg/kg); (ii) the unit dose is between about 0.01 mg/kg and 0.3 mg/kg LTBR-Fc administered not more than once every 3-10 days, e.g., weekly; (iii) the unit dose is between about 0.01 mg/kg and 1 mg/kg LTBR-Fc administered not more than once every 5-20 days, e.g., biweekly; (iv) the unit dose is between about 0.3 mg/kg and 3 mg/kg LTBR-Fc (e.g., between about 0.6 and 1.4 mg/kg LTBR-Fc) administered not more than twice every 20-40 days, e.g., every 25-35 days, or every 28-31 days, or (v) the unit dose is between about 2.5 mg/kg and 3.5 mg/kg LTBR-Fc administered not more than once every 20-40 days, e.g., every 25-35 days, or every 28-31 days. By this method, the patient receives a first therapy, e.g., an NSAID, corticosteroid, or DMARD therapy, to treat RA prior to the administration of the soluble LTBR, and the levels of the first therapy are maintained in the patient at least when the first unit dose of the soluble LTBR is administered to the patient. In one embodiment, the levels of the first therapy are not maintained in the patient after the first or second unit dose of the soluble LTBR. For example, the levels of the first therapeutic agent are diminished, e.g., by administration of lower doses of the first therapeutic agent, or by ceasing administration and allowing the levels of the first therapeutic agent to be cleared from the body. In another embodiment, the patient continues to receive the first therapy during the administration of the soluble LTBR.

Combination Therapies

The methods and compositions described herein can be used in combination with other therapies, such as non-steroidal anti-inflammatory agents (NSAIDs), corticosteroids, and DMARDs.

NSAIDs typically relieve pain by reducing inflammation. Suitable NSAIDs include, for example, aspirin, ibuprofen, naproxen, and ketoprofen. COX-2 inhibitors are a similar class of drugs that can be used in combination with a soluble LTBR for treatment of an autoimmune disorder.

DMARDs typically slow the progression of rheumatoid arthritis. Suitable DMARDS include methotrexate, leflunomide (Arava®), anakinra (Kineret®), hydrocholoquine sulfate (Plaquenil®) antimalarials, gold salts, sulfasalazine (Azulfidine®), minocycline (Minocin®), d-penicillamine, cyclosporin A, cyclosporine (Neoral®), cyclophosphamide and azathioprine (Imuran®). DMARDs also include TNF inhibitors. Tumor necrosis factor alpha (TNF-α) is a proinflammatory cytokine produced by macrophages and lymphocytes. TNF inhibitors help to relieve the proinflammatory effects of this molecule. TNF inhibitors include etanercept (Enbrel™), infliximab (Remicade™), and adalimumab (Humira™).

Corticosteroids typically function as anti-inflammatory agents and can also be used in combination therapy with a soluble LTBR.

In certain embodiments, a soluble LTBR is use as a second line therapy. For example, a patient who is determined to be a DMARD-IR will stop receiving treatment with DMARD and will begin treatment with a soluble LTBR, e.g., LTBR-Fc. In some embodiments, a patient receiving a combination therapy of NSAID and DMARD, will stop receiving the DMARD and will begin receiving a soluble LTBR in combination with the NSAID. The soluble LTBR may be administered in combination with NSAID, or separately. For example, a patient receiving a daily dose of NSAID, may only receive a weekly, or biweekly, or monthly dose of a soluble LTBR. Alternatively, the patient will continue to receive the DMARD and/or NSAID therapies while receiving treatment with the soluble LTBR.

In another embodiment, the soluble LTBR is administered in combination with a second treatment for RA. For example, the combination therapy includes administering a second agent that provides a therapeutic benefit to a patient who has or is at risk for RA. Exemplary second agents include, e.g., non-steroidal anti-inflammatory agents (NSAIDs), corticosteroids, or disease modifying antirheumatic drugs (DMARDs).

In one embodiment, the subject is treated with an RA drug after being diagnosed with RA and prior to administration of a soluble LTBR. The RA drug can be, for example, an NSAID, corticosteroid, or DMARD. In another embodiment, the subject is evaluated to determine if the response to the RA drug is inadequate prior to administration of the soluble LTBR. In certain embodiments, if the subject is determined to have an inadequate response to the RA drug, then the subject is administered a soluble LTBR. In one embodiment, the subject is determined to be asymptomatic, or an adequate responder, for a first manifestation of RA, such as TJC or SJC. In another embodiment, the subject is determined to be asymptomatic, or an adequate responder, for a first manifestation of RA, such as TJC or SJC, and symptomatic, or an inadequate responder for a second manifestation of rheumatoid arthritis, such as synovitis. Synovitis can be detected by any method known in the art, including, for example, by magnetic resonance imaging (MRI).

In one embodiment, the soluble LTBR and the second agent are administered at the same time. In another embodiment, the soluble LTBR is administered first in time and the second agent is administered second in time. In another embodiment, the second agent is administered first in time and the soluble LTBR is administered second in time. The soluble LTBR can replace or augment a previously or currently administered therapy. For example, upon treating with LTBR, administration of the second agent can cease or diminish, e.g., be administered at lower levels. In other embodiments, administration of the previous therapy is maintained. In some embodiments, a previous therapy will be maintained until the level of LTBR reaches a level sufficient to provide a therapeutic effect. The two drugs can be administered in combination.

In one embodiment, a human receiving a first therapy for RA, e.g., an NSAID, corticosteroid, or DMARD, can also be administered a soluble LTBR, e.g., LTBR-Fc. In one embodiment, when the human is administered the soluble LTBR, the first therapy is halted. In another embodiment, the human is monitored for a first preselected result, e.g., an improvement in RA symptoms, e.g., a decrease in TJC or SJC by 10%, 20%, 30%, or more. In one embodiment, when the first preselected result is observed, treatment with the soluble LTBR is decreased or halted. In one embodiment, the human is then monitored for a second preselected result after treatment with the soluble LTBR is halted, e.g., a worsening of an RA symptom, e.g., an increase in TJC or SJC by 10%, 20%, 30% or more. When the second preselected result is observed, administration of the soluble LTBR to the human is reinstated or increased, or administration of the first therapy is reinstated, or the human is administered both a soluble LTBR, or an increased amount of soluble LTBR, and the first therapeutic regimen.

In one embodiment, a human receiving a first therapy for RA, who is then treated with a soluble LTBR, e.g., an LTBR-Fc, continues to receive the first therapy at the same or a reduced amount. In another embodiment, treatment with the first therapy overlaps for a time with treatment with the soluble LTBR, but treatment with the first therapy is subsequently halted.

In one embodiment, the subject is a DMARD inadequate responder (DMARD-IR). For example, the subject is an anti-TNF inadequate responder.

In one embodiment, the method includes evaluating the subject for an improvement in RA symptoms. In some embodiments, the evaluation is performed at least 1 hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after the administration of the soluble LTBR. The subject can be evaluated in one or more of the following periods: prior to beginning of treatment; during treatment; or after one or more elements of the treatment have been administered. Evaluating can include evaluating the need for further treatment with the same soluble LTBR or for additional treatment with additional agents. In a preferred embodiment, if a preselected outcome of the evaluation is obtained, an additional step is taken, e.g., the subject is administered another treatment or another evaluation or test is performed.

III. Pharmaceutical Compositions and Pharmaceutical Administration of Invention

A soluble LTBR, e.g., LTBR-Fc, can be formulated as a pharmaceutical composition, e.g., for administration to a subject to treat an autoimmune disorder, such as RA. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge et al., J. Pharm. Sci. 66:1-19, 1977).

The soluble LTBR can be formulated according to standard methods. Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

In one embodiment, a soluble LTBR (e.g., LTBR-Fc) can be formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the soluble LTBR may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York, 1978.

A soluble LTBR (e.g., LTBR-Fc) can be modified, e.g., with a moiety that improves its stabilization and/or retention in circulation, e.g., in blood, serum, or other tissues, e.g., by at least 1.5, 2, 5, 10, or 50 fold. The modified agent can be evaluated to assess whether it can reach sites of inflammation such as may occur in an autoimmune disorder, such as RA (e.g., by using a labeled form of the agent).

For example, the soluble LTBR can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used.

For example, a soluble LTBR can be conjugated to a water soluble polymer, e.g., a hydrophilic polyvinyl polymer, e.g., polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; and branched or unbranched polysaccharides.

When the soluble LTBR (e.g., LTBR-Fc) is used in combination with a second agent (e.g., a DMARD), the two agents can be formulated separately or together. For example, the respective pharmaceutical compositions can be mixed, e.g., just prior to administration, and administered together or can be administered separately, e.g., at the same or different times.

In one embodiment, a pharmaceutical composition comprises a population of lymphotoxin-β receptor (LT-β-R)-Ig-fusion proteins which comprise a variant LT-β-R extracellular domain of 193 or 194 amino acids in length and a variant Ig portion of 227 amino acids in length, wherein at least 90% of the LT-β-R-Ig-fusion proteins are missing no more than 5 amino acids from the N-terminus of the mature form of the wild type LT-β-R extracellular domain set forth in SEQ ID NO:21 and wherein the LT-β-R-Ig-fusion proteins lack N-terminal pyroglutamic acid and a pharmaceutically acceptable carrier.

In another embodiment, a pharmaceutical composition comprises a population of lymphotoxin-β receptor-immunoglobulin (LT-β-R-Ig)-fusion proteins, the fusion proteins comprising a variant LT-β-R extracellular domain of 193 or 194 amino acids in length and a variant Ig portion, wherein the population has reduced N-terminal pyroglutamic acid formation and reduced C-terminal heterogeneity compared to wild-type LT-β-R-Ig fusion proteins and a pharmaceutically acceptable carrier.

In yet another embodiment a pharmaceutical composition of the invention comprises the amino acid sequence set forth in SEQ ID NO:5.

Administration.

A soluble LTBR (e.g., LTBR-Fc) can be administered to a subject, e.g., a human subject, by a variety of methods. For many applications, the route of administration is one of: intravenous injection or infusion (IV), subcutaneous injection (SC), intraperitoneally (IP), or intramuscular injection. In some cases, administration may be directly into the CNS, e.g., intrathecal, intracerebroventricular (ICV), intracerebral or intracranial. The agent can be administered as a fixed dose, or in a mg/kg dose.

The dose can also be chosen to reduce or avoid production of antibodies against the agent.

The route and/or mode of administration of the soluble LTBR can also be tailored for the individual case, e.g., by monitoring the subject, e.g., using TJC, SJC, CRP levels and standard parameters associated with RA or other autoimmune diseases, e.g., the assessment criteria described herein.

Dosage regimens are adjusted to provide the desired response, e.g., a therapeutic response or a combinatorial therapeutic effect. Generally, a low dose of a soluble LTBR (e.g., LTBR-Fc) optionally formulated separately or together with an appropriate dose of a second therapeutic agent can be used to provide a subject with the soluble LTBR. Exemplary doses of the soluble LTBR are described herein.

Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent. Suitable administration frequencies are described elsewhere herein.

A pharmaceutical composition may include a therapeutically effective amount of a soluble LTBR described herein. Such effective amounts can be determined based on the effect of the administered agent, or the combinatorial effect of an agent and secondary agent if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter, e.g., RA parameter, or amelioration of at least one symptom of the disorder, e.g., RA. A therapeutically effective amount is also one in which any toxic or detrimental effects of the composition is outweighed by the therapeutically beneficial effects. Typically, a therapeutically effective amount is a low dose as described elsewhere herein.

Devices and Kits

Pharmaceutical compositions that include a soluble LTBR (e.g., an LTBR-Fc) can be administered with a medical device. The device can be designed with features such as portability, room temperature storage, and ease of use so that it can be used in emergency situations, e.g., by an untrained subject or by emergency personnel in the field, removed to medical facilities and other medical equipment. The device can include, e.g., one or more housings for storing pharmaceutical preparations that include a soluble LTBR, and can be configured to deliver one or more unit doses of the agent.

For example, the pharmaceutical composition can be administered with a transcutaneous delivery device, such as a syringe, including a hypodermic or multichamber syringe. Other suitable deliver devices include stents, catheters, transcutaneous patches, microneedles, and implantable controlled release devices.

In other examples, the pharmaceutical composition can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other devices, implants, delivery systems, and modules are also known.

A soluble LTBR (e.g., an LTBR-Fc) can be provided in a kit. In one embodiment, the kit includes (a) a container that contains a composition that includes a soluble LTBR, and optionally (b) informational material. The informational material can be descriptive, instructional, marketing or other material that relates to the methods described herein and/or the use of the agents for therapeutic benefit. In one embodiment, the kit also includes a second agent for treating an autoimmune disorder, such as a DMARD for treatment of RA. For example, the kit includes a first container that contains a composition that includes the soluble LTBR, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the soluble LTBR (e.g., LTBR-Fc), e.g., in a suitable dose, dosage form, or mode of administration (e.g., a dose, dosage form, or mode of administration described herein), to treat a subject who has an autoimmune disorder, or who is at risk for experiencing an episode associated with an autoimmune disorder. The information can be provided in a variety of formats, including printed text, computer readable material, video recording, or audio recording, or information that provides a link or address to substantive material.

In addition to the agent, the composition in the kit can include other ingredients, such as a solvent or buffer, a stabilizer, or a preservative. The agent can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the soluble LTBR and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

EXAMPLES

Example 1

Construction and Characterization of LTBR-IgG Constructs to Reduce Heterogeneity The following example describes the characterization of a number of different LTBR immunoglobulin fusion proteins which were created to solve molecular heterogeneities found in the expression of LTBRIgG, including N-terminal heterogeneity, C-terminal heterogeneity, pyroglutamic formation, and sialylation.

N-Terminal Heterogeneity

Predictions of the N-termini encoded by the full length mRNA of LTBR(NP_002333) were done by programs such as SignalP using either neural networks (NN) predictions or with hidden Markov models (HMM) trained on eukaryotes. These two NN and HMM prediction models gave different results for the suggested N-termini of the protein, suggesting S28 or P30 and Q31, respectively (amino acid numbers refer to numbering including the signal sequence). Thus, numerous N-terminal sequence predictions were possible and only by expressing the protein and evaluating the posttranslational modifications could the optimal N-termini with limited variability be determined.

LTBR01 (LTBR-IgG fusion protein version 01) was the initial molecule that was cloned. The N-terminus of LTBR01 started at S28 based on intact LTBR numbering, i.e., including signal sequence. To the LTBR C-termini at M225 was fused the hinge Fc of an IgG1 starting at C220 (Kabat numbering) of an IgG heavy chain. A mutation of the antibody derived cysteine (C220) of the IgG1 hinge to the structurally similar amino acid valine (V199 in LTBR01) was included LTBRIgG. This mutation eliminated the problematic and unwanted formation of a free unpaired thiol in the LTBRIgG, in the IgG1 C220 of the heavy chain is normally disulfide bonded with the C107 of the light chain, lacking the light chain the cysteine (C220) would initially remain unpaired in LTBRIgG it would cause either unwanted scrambling of the CRDs within LTBR or aggregation of the LTBRIgG.

For each LTBRIgG molecule described the genes were constructed, expressed, purified and evaluated for variability in the N-terminal sequence and C-terminal sequence. Results showed that LTBR01 with the S28 N-termini of LTBR was heterogeneous with multiple clipping sites at N-1, N-3 and N-4 as well as a pyroglutamic generated at Q31 (numbering based on full length LTBR sequence described in FIG. 1, including the signal sequence) and was missing the C-terminal K426 from the Fc domain.

Based on these findings, two different constructs, named LTBR05 and LTBR06, were created to improve heterogeneity among the expressed LTBRIgG fusion proteins, particularly with respect to the N and C terminal proteolysis.

LTBR05 was constructed with a C-terminal deletion mutant to avoid having a C-terminal lysine that might undergo proteolysis. Analysis of LTBR05 by mass spectrophotometry (MS) confirmed no further C-terminal truncations upon elimination of the C-terminal lysine, but comparable N-terminal variability to LTBR01.

Therefore, to improve N-terminal heterogeneity, LTBR06 was constructed. LTBR06 was designed to have four amino acids deleted from the N-terminus. This deletion resulted in dramatically decreased N-terminal sequence variability, as described in Table 1. LTBR06 had more than 90% of the desired N-termini (N-4 and N-5 relative to wild type) and N-1 N-termini. The deletions of LTBR06 are also described in FIGS. 1 and 3.

Figure 2A:
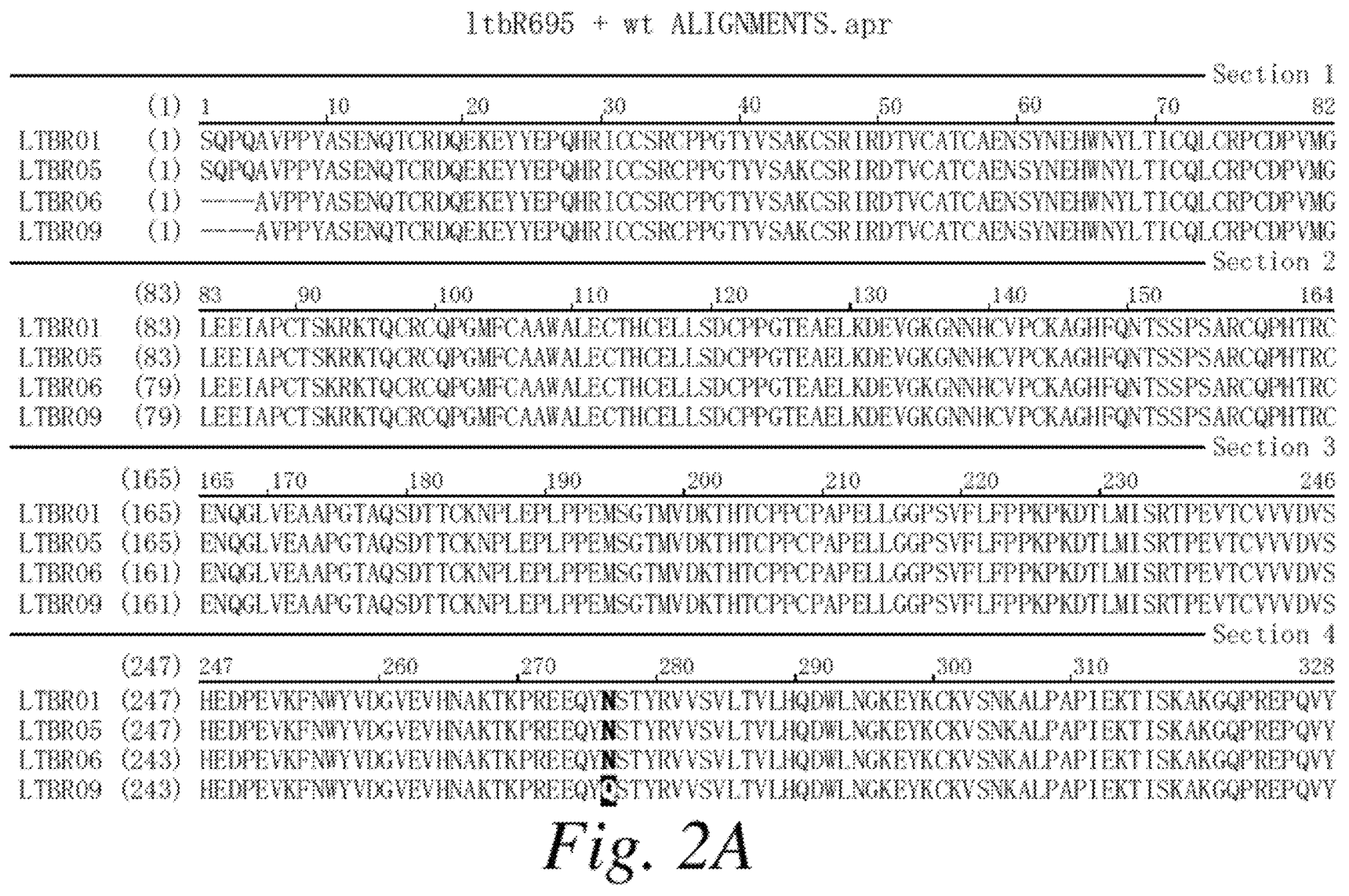

Table 3 provides an overview of the different constructs which were created by deleting portions of the N and C termini of LTBR, as well as the results from such deletions. LTBR05 had a single amino acid removed from the carboxy terminus of LTBR01 (C-1), and LTBR06 had the single C-1 amino acid deletion as well as 4 amino acids deleted from the amino terminus (following the signal sequence—termed N-4). Thus, LTBR06 was engineered to reduce both N- and C-terminal heterogeneity. A comparison of the mature forms of the different constructs is set forth in FIG. 2.

TABLE 3

Comparison of LTBR05 and LTBR06 vs. LTBR01

| Construct name | Features | Purpose | Results |
|---|---|---|---|
| LTBR01 | Wt sequence | 1. Characterization of protein sequence<br>2. Activity | 1. N-terminus N-1, N-3, N-4<br>2. pyroGlu in N-1 and N-3 forms<br>3. C-terminus w/splice variant<br>4. Live and dead material |
| LTBR05 | C-1 | 1. Remove C terminal splice variant of pMDR plasmid | 1. No C-terminal splice variant, C-terminus homogeneous |
| LTBR06 | N-4/C-1 | 1. Reduce N-terminal and C-terminal heterogeneity<br>2. Maintain activity | 1. N-terminus N-4 and N-5, no N terminal pryoGlu<br>2. Fully active ligand binding |

LTBR05 was biochemically characterized, including the N-terminal heterogeneity (results summarized in Table 4). The amino-terminus of LTBR05 was found to exist as N,N-1, and N-3 with the N-1 and N-3 forms converted predominantly to pyroglutamate (<Q).

TABLE 4

Summary of the biochemical characteristics of LTBR05

| Attribute | Test | Result | | |
|---|---|---|---|---|
| Concentration | UV absorbance | 5.0 A280/ml (5.0 mg/ml) | | |
| Purity | SDS-PAGE Red | >90% | | |
|  | SDS-PAGE Nonred. | >90% | | |
| Aggregation | SEC assay | <1% | | |
| % Inactive | HIC assay | ~1% | | |
| Endotoxin | Chromogenic assay | 0.3 EU/mg or 1.5 EU/ml | | |
| N-terminal Sequence | Edman degradation | 33% Sequencing yield (due to <Q)<br>71% N, 29% N-1 | | |
|  |  |  | Theor. | Observed |
| Intact MS | After deglycosylation, reduction and alkylation. | N/C-1 | 50271.55 | 50269 |
|  |  | N-1 < Q/C-1 | 50166.47 | 50166 |
|  |  | N-3 < Q/C-1 | 49941.22 | 49939 |
| Peptide map | LC chromatography of the Endo Lys-C digest | Corresponds to characterized map of LTBR C-1 | | |
| LC/MS | Endo Lys-C digest | 23 peptides identified that account for 95% of the predicted sequence. | | |

LTBR06 was biochemically characterized to determine whether heterogeneity was improved, including whether the N- and C-terminal heterogeneity was improved based on the amino acid substitutions (results summarized in Table 5).

TABLE 5

Summary of the biochemical characteristics of LTBR06

| Attribute | Test | Result |
|---|---|---|
| Concentration | UV absorbance | 25.0 A280/ml (25.0 mg/ml) |
| Purity | SDS-PAGE Red | >90% |
|  | SDS-PAGE Nonred. | >90% |
| Aggregation | SEC assay | <1% |
| % Inactive | HIC assay | <1% |
| Endotoxin | Chromogenic assay | 0.052 EU/mg or 1.3 EU/ml |
| N-terminal Sequence | Edman degradation | 56% N-5, 40% N-4, ~4% N-11 |
| Peptide map | LC chromatography of the Endo Lys-C digest | Corresponds to characterized map of LTBR05 |
| LC/MS | Endo Lys-C digest | 31 peptides identified account for 95% of the predicted amino acid sequence. |

Edman degradation was performed on LTBR06 from LTBR06 expressing cells. As described in Table 5, 56% of the population of LTBR06 proteins were found to be N-5, 40% were N-4, and about 4% were N-11. The sequence of the N-5 species of LTBRIg is described in SEQ ID NO: 23. Using the N-4 and C-1 deletions, the heterogeneity of the protein population was decreased, in comparison to LTBR05 (which represents unmodified extracellular domain of the LTBR fused to a variant).

Example 2

Glycosylation Studies of LTBRIgG Constructs

Glycosylation can also have an impact on protein heterogeneity, as well as activity. To reduce heterogeneity further, therefore, glycosylation mutants were explored to determine whether variable LTBR domain glycosylation impacted binding affinity, expression levels, and folding. LTBR09 was a construct based on LTBR06, with an additional N275Q mutation (amino acid position refers to mature protein—for comparison of sequence and changes between various constructs see FIG. 2).

Table 6 describes the glycosylation occupancy for each of three LTBR constructs at Asn13 and Asn150.

TABLE 6

Glycosylation occupancy

| Construct | % site occupancy Asn13 | % occupancy Asn150 |
|---|---|---|
| LTBR05 | 28* | 86 |
| LTBR06 | 26** | 85 |
| LTBR09 | 22** | 84 |

*Calculated as an average of intact N-terminus, N-1 < Q and N-3 < Q
**Calculated as an average of N-4 and N-5

As shown in Table 6, glycosylation occupancy was relatively invariant within the different constructs for Asn13 and Asn150.

To reduce heterogeneity further, glycosylation mutants were explored in which the N-terminal glycosylation of LTBRIgG was eliminated in either the LTBR extracellular domain or Fc portion of the protein. Elimination of glycosylation sites in the LTBR domain successfully reduced glycosylation and also decreased expression of this protein about ten fold. Table 7 provides an overview of the various mutants and the results from studies which characterized the effect(s) of the deletion of glycosylation sites.

TABLE 7

Additional glycosylation mutants

| Construct name | Features | Purpose | Results |
|---|---|---|---|
| LTBR02 | N13Q | 1. Expression level of 1 glyc. mutation in animal cells 2. Activity assessment | 1. Expression slightly reduced 2. Active in ligand binding |
| LTBR03 | N13Q, N150Q | 1. Expression level of 2 glyc. mutations in animal cells 2. Activity assessment | 1. Expression reduced significantly: about 10% of wt in CHO stable 2. Wildtype ligand binding. 3. No effect on folding. |
| LTBR04 | N13Q, N150Q, N275Q | 1. Expression level of 3 glyc. mutations in animal cells 2. Activity assessment 3. Microbial | 1. Expression reduced a lot. 2. Active in ligand binding 3. Expression from yeast possible. |

LTBR03 is shown in FIG. 5 and SEQ ID NO: 10. Aglycosylated LTBR03 showed binding equivalency to wildtype LTBRIgG (unmodified LTBR extracellular domain and unmodified Fc region) in a competitive FACS assay.

Soluble aglycosylated LTBRIgG was also generated by first capturing the protein using Protein A (primary capture). The captured protein was then run over a phenyl column to remove misfolded and aggregated proteins. Following phenyl chromatography, agly LTBRIgG was purified into a homogenous population using sephacryl S-200. Soluble LTBR was then generated using Asp N digestion, where the digest was subsequently re-exposed to Protein A to remove the Fc portion of the fusion protein. The sLTBR was then purified using DEAE (which removed the Asp N) and gel filtration/characterization, the latter of which is an optional polishing step. Finally, a primary crystal screen was performed.

Example 3

Sialylation Effect on LTBRIgG Pharmacokinetics

In order to study the effects of sialylation on LTBRIgG pharmacokinetics, sialyation of LTBRIgG was forced using α-2,6-Sialyltransferase from rat liver (Boehringer Mannheim). α-2,6-Sialyltransferase is specific for Gaβ1→4GlcNAc, and will sialylate 75-100% of terminal N-linked galactose residues. Sialylation of LTBRIgG achieved various levels of sialylated protein, which were then evaluated for pharmacokinetics. Pharmacokinetic data of low, medium, and high sialylated LTBRIg (version LTBR05) was analyzed in mouse sera. The results are described below in Tables 8 and 9.

TABLE 8

Sialylation (SA) of LTBR-Ig PK Data (concentrations in ug/ml)

| sialylation | mouse # | time (hr) 0 | time (hr) 0.25 | time (hr) 7 | time (hr) 24 | time (hr) 72 | time (hr) 168 |
|---|---|---|---|---|---|---|---|
| low | 1 | blq | 75 | 23 | 17 | 1.4 | 0.11 |
| low | 2 | blq | 130* | 30 | 22 | 2.5 | 0.62 |
| low | 3 | blq | 62 | 23 | 19 | 1.6 | <0.02 |
| middle | 4 | blq | 92 | 42 | 29 | 3.2 | 0.94 |
| middle | 5 | blq | 89 | 38 | 26 | 3.8 | 0.050 |
| middle | 6 | blq | 73 | 41 | 29 | 2.9 | 0.087 |
| high | 7 | blq | 110 | 47 | 32 | 3.9 | 0.3 |
| high | 8 | blq | 110 | 50 | 34 | 3.9 | 0.49 |
| high | 9 | blq | 110 | 42 | 34 | 4.3 | 0.64 | blq = below limit of quantitation
*not included in average described in Table 8

TABLE 9

Average SA from Table 8

| | time (hr) 0 | time (hr) 0.25 | time (hr) 7 | time (hr) 24 | time (hr) 72 | time (hr) 168 |
|---|---|---|---|---|---|---|
| low | 0 | 69 | 25 | 19 | 2 | 0 |
| middle | 0 | 85 | 40 | 28 | 3 | 0 |
| high | 0 | 110 | 40 | 33 | 4 | 0 |

Figure 13:
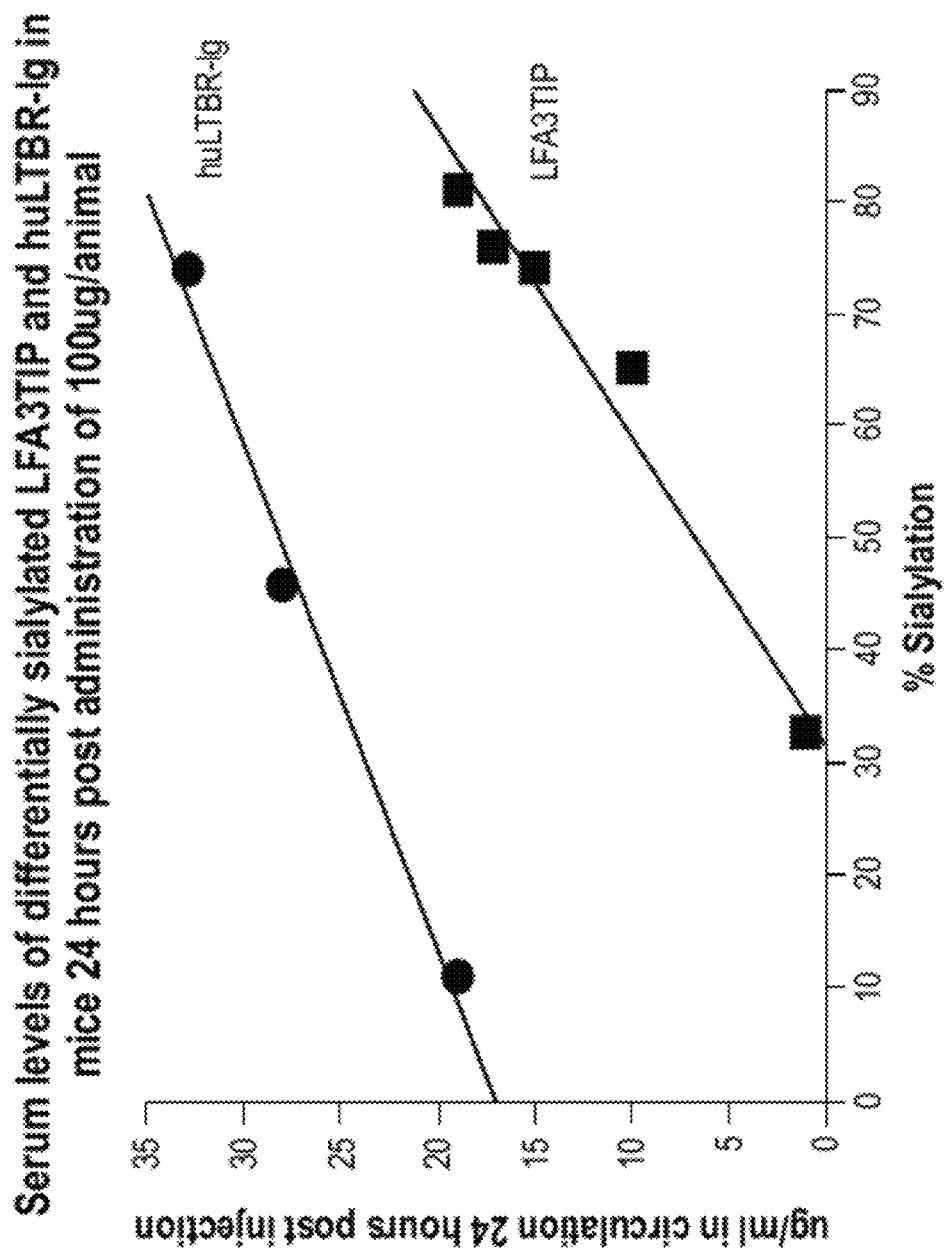
FIG. 13 graphically depicts serum levels of differentially sialylated LFA3TIP and hu-LTBR-Ig (LTBR05) in mice 24 hours post administration with 100 ug/animal.

FIG. 13 describes the difference in pharmacokinetics between huLTBRIgG and LFA3TIP (dimeric fusion protein that consists of the extracellular CD2-binding portion of the human leukocyte function antigen-3 (LFA-3) linked to the Fc (hinge, CH2 and CH3 domains) portion of human IgG1). As shown in FIG. 13, LTBRIgG had increased serum levels regardless of sialylation in comparison to LFA3TIP.

Example 4

Effects of Domain Truncation of LTBRIgG

The TNFRIgG product entanercept has significant misfolding heterogenities within the protein, a situation similar to LTBRIgG. To help decrease the extent of misfolding within the TNFR portion a based on the contact areas shown in the cocrystal structure of TNFR/TNF, a truncated version of TNFRFc was created using 2.6 domains of TNFR. The truncated TNF receptor molecule retained full binding activity to the TNFa ligand. Based on the CRD structural alignment of LTBR and TNFR domains 4 and the C-terminal half of domain 3, as well as several other variations, truncated versions of LTBRIgG were expressed and evaluated for their affinity to LTa1b2 (see Table 2 above).

Binding affinities of the various truncations (including D 3-1, D 2-1 (wt=D1-4)) were determined. None of the purified truncated LTBRIgG molecules retained high affinity for the LTa1b2 showing modeling contacts between LTBR/LTa1b2. Thus, TNFR/TNFa was poor predictor of contact residues between LTBR and LTa1b2.

Example 5

Design of Hinges for LTBRIgG

A number of different hinge constructs were created which could be used to connect LTBR and IgG. A description of the different hinges is described in FIG. 6, including the following hinge sequences. If used, the sequences below would be placed following the C-terminal amino acid of the LTBR extracellular domain, i.e., M.

```
                                         (SEQ ID NO: 13)
LTBR06 hinge: VDKTHTCPPCPAP (SEQ ID NO: 14)
Hinge 2211 (D169N): VNKTHTCPPCPAP (SEQ ID NO: 15)
Hinge 2212 (T198N): VDKNHTCPPCPAP (SEQ ID NO: 16)
Hinge 2221 (valine deletion): DKTHTCPPCPAP (SEQ ID NO: 17)
Hinge 2217 (full length): EPKSCDKTHTCPPCPAP (SEQ ID NO: 18)
Hinge 2219 (G4-hinge-G4Fc): ESCDKYGPPCPPCPAP (SEQ ID NO: 19)
Hinge 2218 (G2-hinge-G2Fc): CCVECPPCPAPPVAGP (SEQ ID NO: 20)
Hinge 2220 (short hinge-G1Fc): CPPCPAP
```

Analysis of the expression for each of the hinges in LTBRIgG in comparison to LTBR06 is described in FIG. 7.

Examples 6 to 8 describe clinical studies showing the efficacy of LTBRIgG (more specifically LTBR06) for the treatment of an autoimmune disorder.

Example 6

Low Doses of LTBR-Fc are Effective to Treat Rheumatoid Arthritis

A dose of 0.05 mg/kg LTBR-Fc (version LTBR06) was chosen as the lowest of five dose cohorts in randomized, blinded, placebo-controlled, drug escalating clinical study to evaluate the safety, tolerability and pharmacokinetics of multiple doses of LTBR-Fc in RA patients. 0.05 mg/kg was chosen as the lowest dose cohort because it was expected to be a no-effect dose with regard to safety and pharmacokinetic findings. Indeed this was a no-effect dose with regard to acute phase response in earlier studies. Assessing efficacy was not a primary or secondary objective of the study. Dosing was performed once weekly for 4 weeks. All members of the cohort were DMARD-IR. The patients received methotrexate therapy while receiving the LTBR-Fc of the study.

Exemplary results are shown in FIG. 8. This figure illustrates data for a placebo cohort (n=4); a cohort receiving 0.05 mg/kg LTBR-Fc (n=6); and a cohort receiving 0.1 mg/kg LTBR-Fc (n=3). Tender joint counts (TJC) and swollen joint counts (SJC) were evaluated for each subject.

Remarkably, the 0.05 mg/kg cohort showed a dramatic (50-70%) improvement in TJC and SJC compared to placebo. Similar improvement was also seen with the next higher dose cohort (0.1 mg/kg). This surprising observation resulted in a complete redesign of the study, necessitating the addition of an additional dose cohort lower than 0.05 mg/kg (so that a lower dosage range could be tested, and a linear dose response could be seen and a lower dose response determined), and in the cancellation of the highest dose cohort (3 mg/kg) from the study.

Example 7

Clinical Study of LTBR-Fc (LTBR06) for Treatment of RA (Phase IIA Data)

The following example describes results from a phase IIa clinical study which examined the efficacy of a range of doses of LTBR-Fc (version LTBR06) administered to patients for the treatment of rheumatoid arthritis (RA).

The study was a blinded, randomized, placebo-controlled, dose-ranging study in 47 DMARD-IR RA patients. Screening for the study included identifying patients with active RA who were methotrexate (mtx)-IR. Cohort doses included the following groups: 0.01 mg/kg, 0.05 mg/kg, 0.1 mg/kg, 0.3 mg/kg, 1.0 mg/kg or 3.0 mg/kg. LTBR-Fc was administered in combination with mtx. The randomized to LTBR-Fc or placebo ratio was 3:1. Subcutaneous injection once weekly for 4 weeks followed by 8 weeks of observation. Baseline demographics and disease characteristics were similar throughout the placebo and experimental groups (11 placebo, 36 LTBR06 patients). The average duration of RA including all of the patients was 3.1 years. 39 of the patients (83%) had had prior DMARD treatment, and 3 of 6% had had prior anti-TNF treatment. The median dose of methotrexate (mtx) at baseline was 15 mg/week. For the total number of patients, the median of ACR core set of measurements was 16 SJC, 21 TJC, and 1.33 HAQ.

Figure 9:
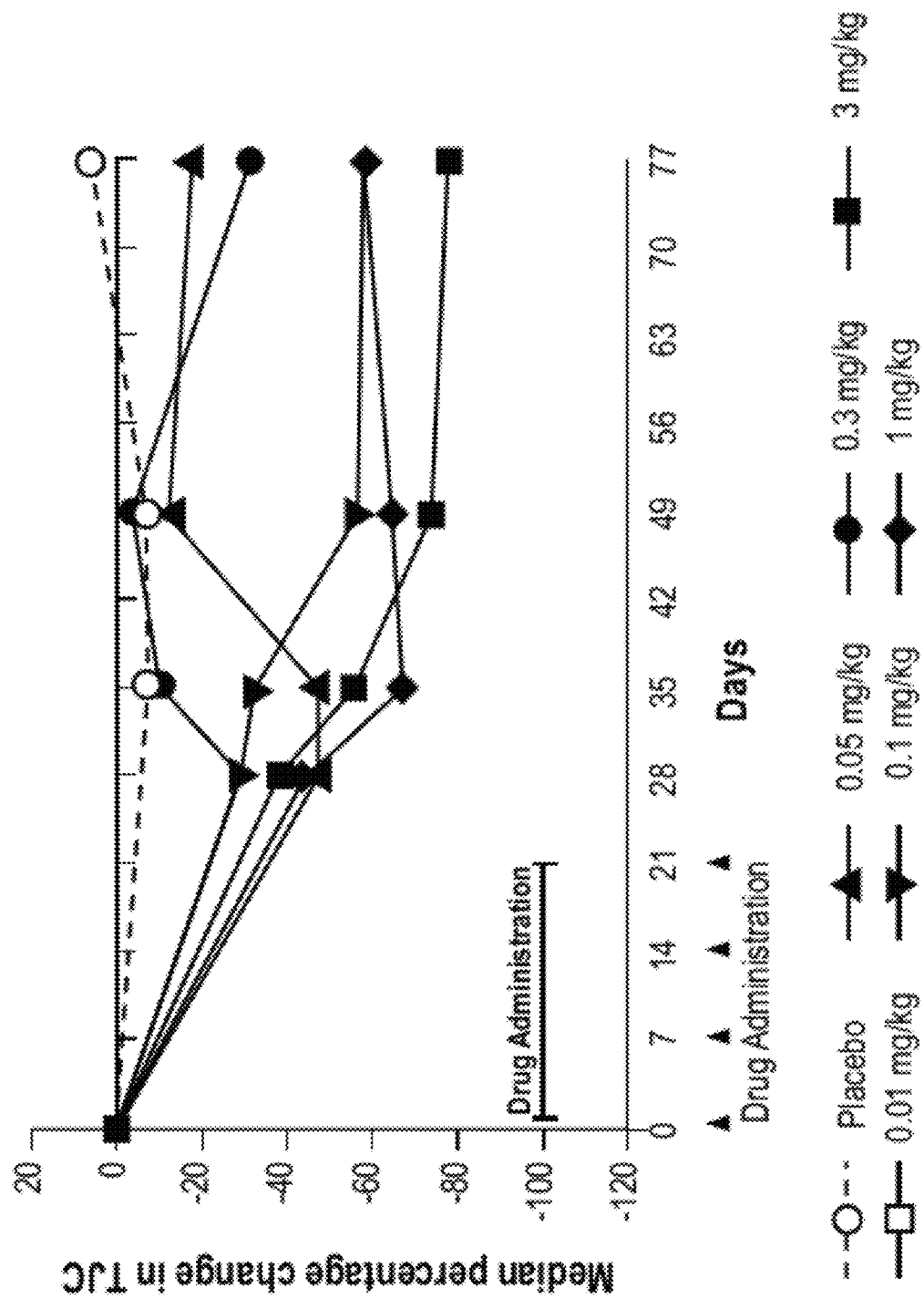
FIG. 9 provides a graph which depicts a decrease in Tender Joint Counts (TJC) in patients following treatment with LTBR-Fc (LTBR06).
Figure 10:
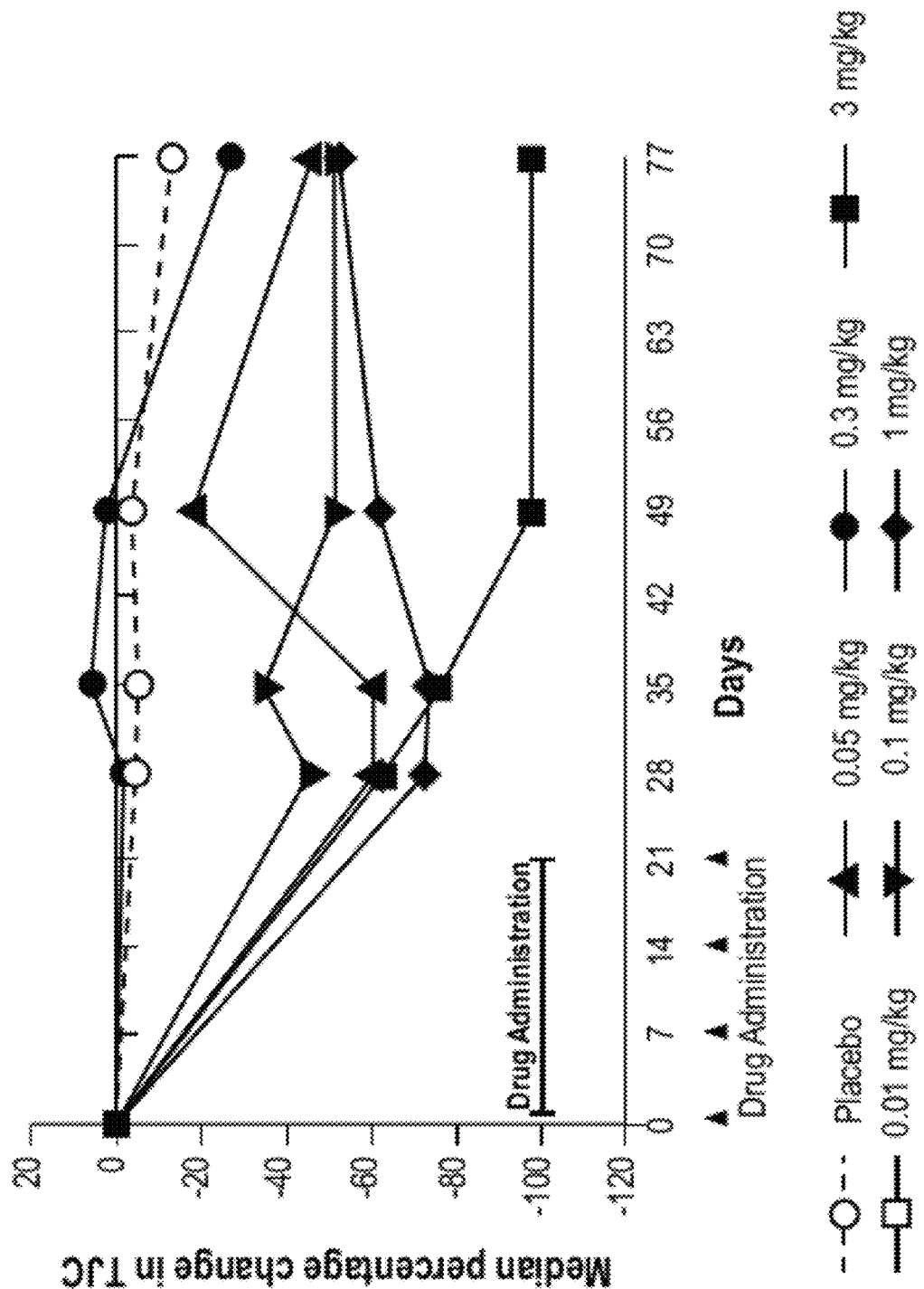
FIG. 10 provides a graph which depicts a decrease in Swollen Joint Counts n (SJC) in patients following treatment with LTBR-Fc (LTBR06).
Figure 11:
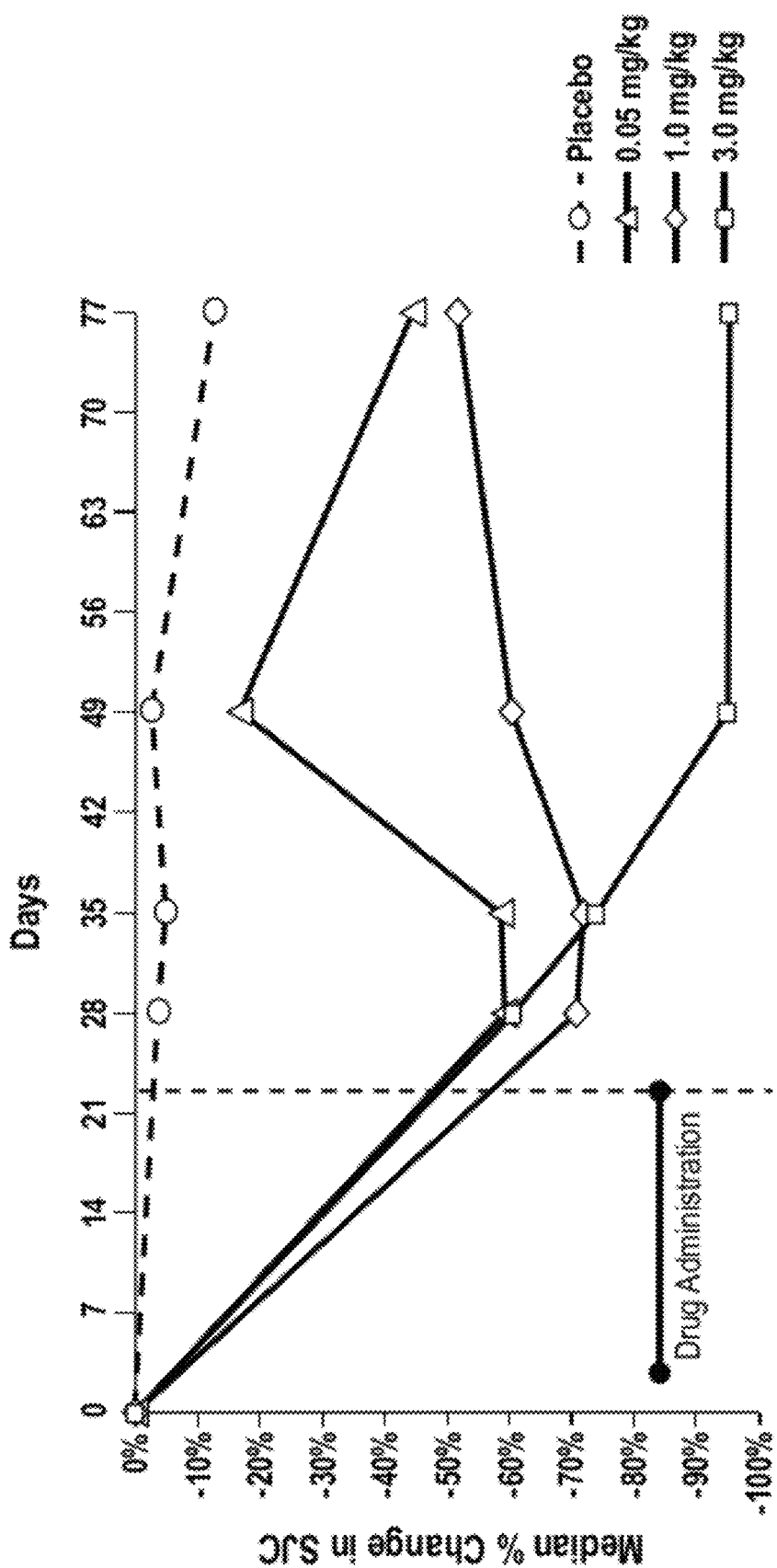
FIG. 11 provides a graph which depicts the median % change in Swollen Joint Counts n (SJC) in patients following treatment with LTBR-Fc (LTBR06).
Figure 12:
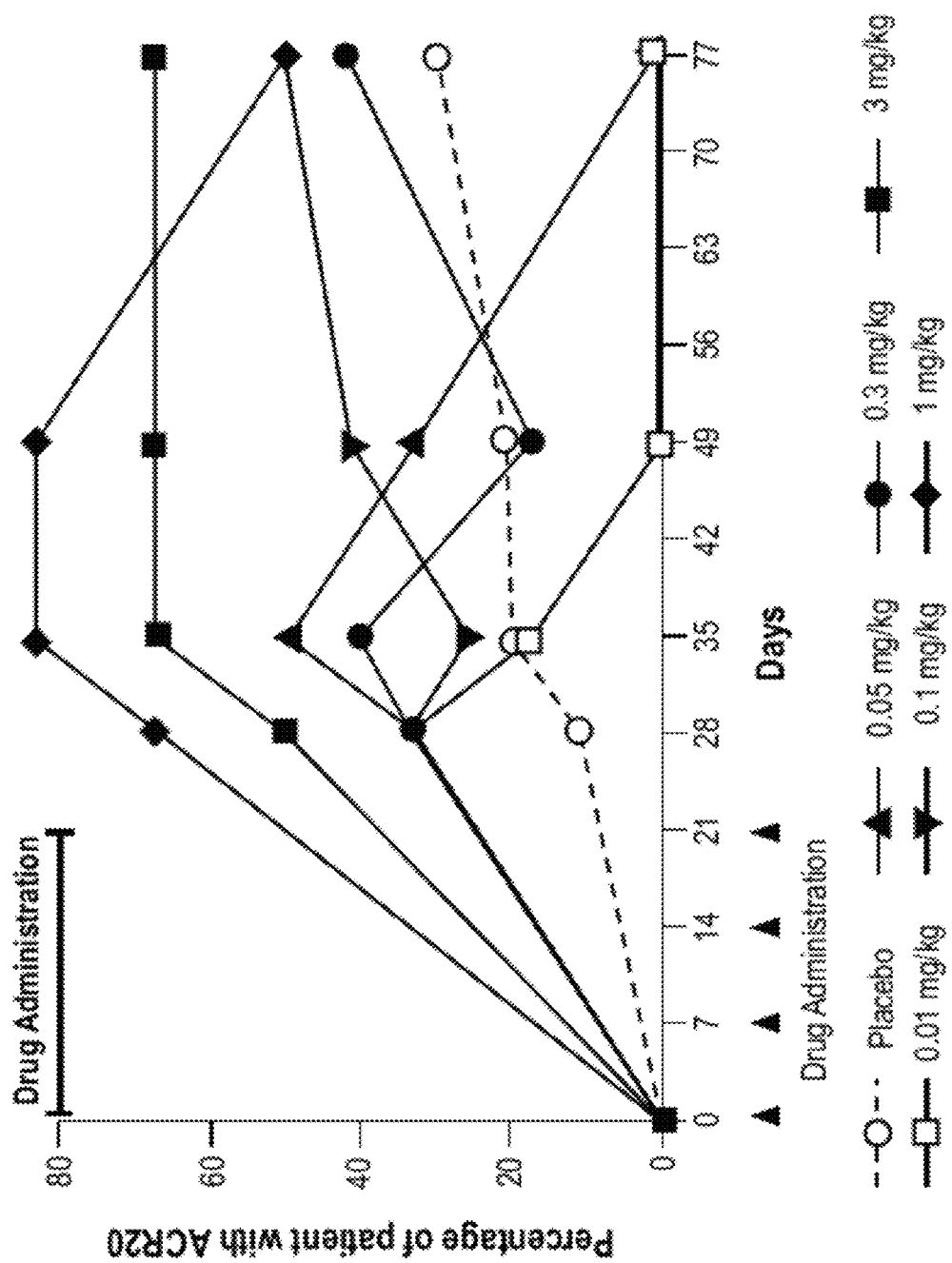
FIG. 12 provides a graph which depicts ACR20 improvements in patients following treatment with LTBR-Fc (LTBR06).

LTBR-Fc proved effective at treating RA in patients. The results showed substantial improvement in the majority of ACR core set measurements in a dose dependent manner. At Day 35 (2 weeks after the last dose), mean improvement was SJC 60% vs 4.6% (LTBR-Fc vs placebo) and TJC 47% vs 6.7% (LTBR-Fc vs placebo) (see FIGS. 10 to 12). As shown in FIGS. 9-11, improvements in SJC and TJC were durable, persisting 8 weeks after the final LTBR-Fc dose through Day 77. The greatest improvements were reported in the LTBR-Fc 1.0 mg/kg and 3.0 mg/kg groups, as the ACR20 response rates for these two dosing groups was 65% and 85% at Day 77, respectively. Improvement in the ACR20 response was also greater than placebo for all dose groups, as shown in FIG. 12 and Table 10.

TABLE 10

ACR20/50/70 response rates (% of patients) at Day 77

| Doses | ACR20 | ACR50 | ACR70 |
|---|---|---|---|
| Placebo (n = 10) | 30 | 0 | 0 |
| 0.01 mg/kg (n = 6) | 0 | 0 | 0 |
| 0.05 mg/kg (n = 6) | 0 | 0 | 0 |
| 0.1 mg/kg (n = 4) | 50 | 25 | 25 |
| 0.3 mg/kg (n = 5) | 40 | 40 | 20 |
| 1.0 mg/kg (n = 6) | 50 | 33 | 17 |
| 3.0 mg/kg (n = 6) | 67 | 50 | 33 |

ACR20 (ACR50, ACR70) response is defined as a 20% (50%, 70%) improvement in SJC and TJC, with a 20% (50%, 70%) improvement in at least 3 of the following indices: IGA, PGA, pain-VAS, HAQ, CRP (ESR if CRP is missing).

Overall, LTBR-Fc proved safe in patients who received treatment. 55% of patients (6/11) receiving placebo and 67% of patients (24/36) receiving LTBR-Fc (LTBR06) experienced adverse events (AEs) (e.g., headaches, chills, fatigue) although none were severe. The most common AE in patients receiving LTBR-Fc (LTBR06) was headache, reported in 19% of patients vs 9% of patient receiving placebo. No drug-related serious infections or drug-related serious AEs were reported during the study period. One serious infection was reported in the 3.0 mg/kg group on Day 91 (acute bronchitis, unlikely related to treatment). Transient mild-to-moderate flu-like symptoms were observed in 25% of patients within 24 h after the first dose of LTBR-Fc. These symptoms responded well to acetaminophen and did not usually recur after subsequent doses (decreased on subsequent doses—reported in 8%, 9% and 6% of patients after the second, third, and fourth doses, respectively). Decreased immunogenicity was observed with increased dose, there were no effects on PK, AE's or efficacy.

Overall, the results showed that LTBR-Fc was effective at treating RA in doses ranging from 0.01 mg/kg to 3 mg/kg.

Example 8

Clinical Study of LTBR-Fc (LTBR06) for Treatment of RA

A long term extension study is used to further evaluate the safety, tolerability, and efficacy of LTBR-Fc (LTBR06) in subjects with RA. Patients from previous studies, such as the study described in Example 7 may be included in the study. The study design includes administering LTBR-Fc (LTBR06) to RA patients in one of the following doses subcutaneously: 70 mg every other week; 200 mg every other week; 70 mg monthly; 200 mg monthly; or a placebo dose. Patients are evaluated for improvements in the responses/scores of the following efficacy parameters will be determined: American College of Rheumatology (ACR) Core Set of measurements, DAS28, Short Form (SF-36), Functional Assessment of Chronic Illness Therapy (FACIT) questionnaires, Sjogren's Assessment. Statistically significant improvements in such parameters in comparison to the placebo control group will indicate efficacy.

EQUIVALENTS

All patents, patent applications, and references are hereby incorporated by reference in their entirety. In the case of conflict, the present application controls.

Each of the limitations of the invention can encompass various embodiments of the invention. It is, therefore anticipated that each of the limitations of the invention involving any one element or combinations of elements can be included in each aspect of the invention.

Forming part of the present disclosure is the appended Sequence Listing, the contents of which are summarized in the table below:

| SEQ ID NO: | DESCRIPTION |
|---|---|
| 1 | Wild type human LTBR sequence (amino acid) |
| 2 | LTBR06 Ig (Fc) domain (amino acid) |
| 3 | LTBR06, variant LTBR extracellular domain (nucleic acid) |
| 4 | LTBR06, variant LTBR extracellular domain (amino acid) |
| 5 | LTBR06, mature form (amino acid) |
| 6 | LTBR01 (amino acid) |
| 7 | LTBR06 (nucleic acid) |
| 8 | LTBR06 (amino acid) |
| 9 | LTBR05, mature form (amino acid) |
| 10 | non-glycosylated LTBR-IgG (amino acid) (pEAG 1980) |
| 11 | LTBR01, mature form (amino acid) |
| 12 | LTBR09, mature form (amino acid) |
| 13 | Hinge (amino acid) |
| 14 | 2211 hinge (amino acid) |
| 15 | 2212 hinge (amino acid) |
| 16 | 2221 hinge (amino acid) |
| 17 | 2217 hinge (amino acid) |
| 18 | 2219 hinge (amino acid) |
| 19 | 2218 hinge (amino acid) |
| 20 | 2220 hinge (amino acid) |
| 21 | Wild type human LTBR, extracellular domain (amino acid) |
| 22 | Ig (Fc) domain unmodified (amino acid) |
| 23 | N-5 variant LTBR extracellular domain (amino acid) |

What is claimed is:

1. A composition comprising a population of lymphotoxin-β receptor (LT-β-R)-Ig-fusion proteins which comprise a variant LT-β-R extracellular domain of 193 or 194 amino acids in length and a variant Ig portion of 227 amino acids in length, wherein at least 90% of the LT-β-R-Ig-fusion proteins are missing no more than 5 amino acids from the N-terminus of the mature form of the wild type LT-β-R extracellular domain, which extracellular domain is set forth in SEQ ID NO:21, and wherein the LT-β-R-Ig-fusion proteins lack N-terminal pyroglutamic acid.

2. The composition of claim 1, wherein the N-terminal amino acid of the variant LT-β-R-Ig fusion protein is a non-polar amino acid.

3. The composition of claim 2, wherein the non polar amino acid is either a valine, which corresponds to amino acid six of the mature form of the wild type LT-β-R extracellular domain of SEQ ID NO:21 or an alanine, which corresponds to amino acid five of the mature form of the wild type LT-β-R extracellular domain of SEQ ID NO:21.

4. The composition of claim 1, wherein the N-terminal amino acid of at least 95% of the LT-β-R-Ig-fusion proteins is either a valine, which corresponds to amino acid six of the mature form of the wild type LT-β-R extracellular domain of SEQ ID NO:21or an alanine, which corresponds to amino acid five of the mature form of the wild type LT-β-R extracellular domain of SEQ ID NO:21.

5. The composition of any one of claim 1, 3 and 4, wherein the LT-β-R-Ig fusion proteins are made by expressing a nucleic acid molecule comprising a nucleotide sequence encoding the extracellular domain of LT-β-R set forth in SEQ ID NO:4 or SEQ ID NO:23 in a mammalian cell.

6. The composition of claim 5, wherein variant Ig portion comprises Fc regions of an IgG1 isotype.

7. The composition of claim 5, wherein the variant Ig portion comprises the amino acid sequence set forth in SEQ ID NO:2.

8. The composition of claim 5, wherein the Ig portion is non-glycosylated.

9. The composition of claim 5, wherein the LT-β-R-Ig fusion proteins are made by expressing a nucleic acid molecule encoding the LT-β-R-Ig fusion protein set forth in SEQ ID NO:5 in a mammalian cell.

10. The composition of claim 9, wherein the nucleic acid molecule comprises the sequence set forth in SEQ ID NO:7.

11. The composition of claim 10, wherein the step of expressing is done at manufacturing scale.

12. A composition comprising a population of lymphotoxin-β receptor-immunoglobulin (LT-β-R-Ig)-fusion proteins comprising a variant LT-β-R extracellular domain and a variant Ig portion, wherein at least 90% of the LT-β-R-Ig-fusion proteins are missing no more than 5 amino acids from the N-terminus of the mature form of the wild type LT-β-R extracellular domain, which extracellular domain is set forth in SEQ ID NO:21, and wherein the variant LT-β-R extracellular domain is aglycosylated.

13. A composition comprising a population of lymphotoxin-β receptor-immunoglobulin (LT-β-R-Ig)-fusion proteins, the fusion proteins comprising a variant LT-β-R extracellular domain of 193 or 194 amino acids in length and a variant Ig portion, wherein at least 90% of the LT-β-R-Ig-fusion proteins are missing no more than 5 amino acids from the N-terminus of the mature form of the wild type LT-β-R extracellular domain, which extracellular domain is set forth in SEQ ID NO:21, and wherein the population has reduced N-terminal pyroglutamic acid formation, and reduced C-terminal heterogeneity compared to wild-type LT-β-R-Ig fusion proteins.

14. The composition of claim 13, wherein at least 90% of the LT-β-R-Ig-fusion proteins comprise a variant LT-β-R extracellular domain as set forth the amino acid sequence of SEQ ID NO:4 or SEQ ID NO: 23.

15. The composition of claim 13, wherein the variant Ig portion comprises a mutation in the hinge region.

16. A pharmaceutical composition comprising a population of lymphotoxin-β receptor (LT-β-R)-Ig-fusion proteins which comprise a variant LT-β-R extracellular domain of 193 or 194 amino acids in length and a variant Ig portion of 227 amino acids in length, wherein at least 90% of the LT-β-R-Ig-fusion proteins are missing no more than 5 amino acids from the N-terminus of the mature form of the wild type LT-β-R extracellular domain, which extracellular domain is set forth in SEQ ID NO:21, and wherein the LT-β-R-Ig-fusion proteins lack N-terminal pyroglutamic acid and a pharmaceutically acceptable carrier.

17. The composition of claim 16, wherein the N-terminal amino acid of the variant LT-β-R-Ig fusion protein is a non-polar amino acid.

18. The composition of claim 17, wherein the non polar amino acid is either a valine, which corresponds to amino acid six of the mature form of the wild type LT-β-R extracellular domain of SEQ ID NO:21 or an alanine, which corresponds to amino acid five of the mature form of the wild type LT-β-R extracellular domain of SEQ ID NO:21.

19. The composition of claim 16, wherein the N-terminal amino acid of at least 95% of the LT-β-R-Ig-fusion proteins is either a valine, which corresponds to amino acid six of the mature form of the wild type LT-β-R extracellular domain of SEQ ID NO:2 or an alanine, which corresponds to amino acid five of the mature form of the wild type LT-β-R extracellular domain of SEQ ID NO:21.

20. The composition of claim 16, 18, or 19, wherein the LT-β-R-Ig fusion proteins are made by expressing a nucleic acid molecule comprising a nucleotide sequence encoding the extracellular domain of LT-β-R set forth in SEQ ID NO:4 in a mammalian cell.

21. A method of treating an autoimmune disorder comprising administering the pharmaceutical composition of claim 20 to a subject in need thereof, wherein the autoimmune disorder is rheumatoid arthritis.

22. A pharmaceutical composition comprising a population of lymphotoxin-β receptor-immunoglobulin (LT-β-R-Ig)-fusion proteins, the fusion proteins comprising a variant LT-β-R extracellular domain of 193 or 194 amino acids in length and a variant Ig portion, wherein at least 90% of the LT-β-R-Ig-fusion proteins are missing no more than 5 amino acids from the N-terminus of the mature form of the wild type LT-β-R extracellular domain, which extracellular domain is set forth in SEQ ID NO:21, and wherein the population has reduced N-terminal pyroglutamic acid formation and reduced C-terminal heterogeneity compared to wild-type LT-β-R-Ig fusion proteins and a pharmaceutically acceptable carrier.

23. The pharmaceutical composition of claim 22, wherein at least 90% of the LT-β-R-Ig-fusion proteins comprise a variant LT-β-R extracellular domain as set forth the amino acid sequence of SEQ ID NO:4 or SEQ ID NO: 23.

24. The pharmaceutical composition of claim 22, wherein the variant Ig portion comprises a mutation in the hinge region.

25. A pharmaceutical composition, comprising a polypeptide comprising the amino acid sequence set forth in SEQ ID NO:5.

26. A method of treating an autoimmune disorder comprising administering the pharmaceutical composition of claim 25 to a subject in need thereof, wherein the autoimmune disorder is rheumatoid arthritis.

27. The method of claim 26, wherein the pharmaceutical composition is administered to the subject at a dose of from about 0.6 to 3 mg/kg biweekly.

28. The method of claim 26, wherein the pharmaceutical composition is administered subcutaneously.

29. An isolated polypeptide comprising a variant LT-β-R extracellular domain of 193 or 194 amino acids in length and a variant Ig portion of 227 amino acids in length, wherein the polypeptide is missing no more than 5 amino acids from the N-terminus of the mature form of the wild type LT-β-R extracellular domain, which extracellular domain is set forth in SEQ ID NO:21 and wherein the polypeptide lacks N-terminal pyroglutamic acid.

30. The isolated polypeptide of claim 29, wherein the N-terminal amino acid is a non-polar amino acid.

31. The isolated polypeptide of claim 30, wherein the non polar amino acid is either a valine, which corresponds to amino acid six of the mature form of the wild type LT-β-R extracellular domain of SEQ ID NO:21 or an alanine, which corresponds to amino acid five of the mature form of the wild type LT-β-R extracellular domain of SEQ ID NO:21.

32. The isolated polypeptide of claim 29, which is made by expressing a nucleic acid molecule comprising a nucleotide sequence encoding the extracellular domain of LT-β-R set forth in SEQ ID NO:23 SEQ ID NO:4 or in a mammalian cell.

33. An isolated nucleic acid molecule encoding the polypeptide of any one of claims 29-32.

34. The isolated nucleic acid molecule of claim 33, which nucleic acid molecule comprises of the nucleotide sequence set forth in SEQ ID NO:7.

35. A vector comprising the nucleic acid molecule of claim 34.

36. An isolated or cultured host cell expressing the vector of claim 35.

37. The cell of claim 36, which is a Chinese Hamster Ovary (CHO) cell.

38. A process for making a composition comprising a population of lymphotoxin-β receptor (LT-β-R)-Ig-fusion proteins which comprise a variant LT-β-R extracellular domain and a variant Ig portion, wherein at least 90% of the LT-β-R-Ig-fusion proteins are missing no more than 5 amino acids from the N-terminus of the mature form of the wild type LT-β-R extracellular domain set forth in SEQ ID NO:21, the process comprising, expressing a nucleic acid molecule encoding the LT-β-R-Ig fusion protein set forth in SEQ ID NO:8 in a mammalian cell, obtaining the population from the culture supernatant, and, optionally, purifying the supernatant, to thereby obtain a composition comprising a population of lymphotoxin-β receptor (LT-β-R)-Ig-fusion proteins which comprise a variant LT-β-R extracellular domain and a variant Ig portion, wherein at least 90% of the LT-β-R-Ig-fusion proteins are missing no more than 5 amino acids from the N-terminus of the mature form of the wild type LT-β-R portion set forth in SEQ ID NO:21.

39. The process of claim 38, wherein the nucleic acid molecule comprises the nucleotide sequence set forth in SEQ ID NO:7.

40. The process of claim 38, wherein the nucleic acid molecule consists of the nucleotide sequence set forth in SEQ ID NO:7.

41. A method of treating rheumatoid arthritis in a human subject, in need thereof, the method comprising administering to the subject a dose of LT-β-R-Ig fusion protein, wherein the dose is sufficient to maintain an average concentration of from about 0.14 ug/ml to about 3.5 ug/ml in the serum of the subject.

42. A method of treating rheumatoid arthritis in a human subject, in need thereof, the method comprising administering to the subject a dose of LT-β-R-Ig fusion protein, wherein the dose is sufficient to maintain an average a minimal average concentration of about 0.6 ug/ml in the serum of the subject.

43. The method of claim 42, wherein the LT-β-R-Ig fusion protein comprises the amino acid sequence set forth in SEQ ID NO:5.

44. The method of claim 42, wherein the concentration is achieved by administering LT-β-R-Ig fusion protein at a dose of from about 0.01 to about 5 mg/kg once every 7-60 days.

45. A method of treating rheumatoid arthritis in a human subject, in need thereof, the method comprising administering to the subject a dose of LT-β-R-Ig fusion protein of from about 0.6 to 3 mg/kg not more than twice every 7-30 days.

46. The method of claim 45, the method comprising administering to the subject a dose of LT-β-R-Ig fusion protein of from about 0.6 to 3 mg/kg once every 7-14 days.

47. The method of claim 45, wherein administration is once every 14-30 days.

48. The method of claim 45, wherein administration is once every 28-60 days.

49. The method of claim 45, wherein administration is once every 7-30 days.

50. A method of treating an autoimmune disorder in a human subject, the method comprising administering to the subject a dose of a pharmaceutical composition comprising a population of LT-β-R-Ig fusion proteins comprising a variant LT-β-R extracellular domain of 193 or 194 amino acids in length, wherein at least 90% of the LT-β-R-Ig-fusion proteins are missing no more than 5 amino acids from the N-terminus of the mature form of the wild type LT-β-R extracellular domain set forth in SEQ ID NO:21 and wherein the dose is sufficient to maintain a minimal average concentration of about 0.6 ug/ml in the serum of the subject, wherein the autoimmune disorder is rheumatoid arthritis.

51. The method of claim 50, wherein the LT-β-R-Ig fusion protein further comprises a variant Ig portion.

52. The method of claim 50, wherein the pharmaceutical composition comprises the amino acid sequence set forth in SEQ ID NO:5.

53. The method of claim 52, wherein administration is twice monthly.

54. The method of claim 52, wherein administration once monthly.

55. The method of claim 52, wherein administration is subcutaneous.

56. The method of claim 52, wherein the dose is about 1 mg/kg.

57. The method of claim 52, wherein the dose is about 3 mg/kg.

58. The method of claim 52, wherein the dose is about 1 mg/kg administered about every 7 to 20 days.

59. The method of claim 52, wherein the dose is about 3 mg/kg administered about every 14 to 30 days.

60. The method of claim 52, wherein the dose is about 1 mg/kg administered about every 14 days.

61. The method of claim 52, wherein the subject has been treated with a rheumatoid arthritis drug after being diagnosed with rheumatoid arthritis and prior to administration of the LT-β-R-Ig fusion protein.

62. The method of claim 61, wherein the rheumatoid arthritis drug is chosen from the group consisting of a DMARD, an NSAID, and a corticosteroid.

63. The method of claim 61, wherein the human is a DMARD-inadequate responder.

64. The method of claim 61, wherein the rheumatoid arthritis drug is a TNF inhibitor.

65. The method of claim 61, wherein the rheumatoid arthritis drug is adalimumab (Humira®), etanercept (Enbrel®), or infliximab (Remicade®).

66. The method of claim 61, wherein LT-β-R-Ig is administered in combination with the rheumatoid arthritis drug.

67. The method of claim 61, wherein the human is evaluated to determine if the response to the rheumatoid arthritis drug is inadequate prior to administration of LT-β-R-Ig.

68. The method of claim 67, wherein the human is determined to have an inadequate response to the rheumatoid arthritis drug, and then the human is administered LT-β-R-Ig.

69. The method of claim 61, wherein the human is asymptomatic for a first manifestation of rheumatoid arthritis and is symptomatic for a second manifestation of rheumatoid arthritis.

70. The method of claim 61, wherein LT-β-R-Ig is administered in place of the rheumatoid arthritis drug.

71. The method of claim 61, wherein administration is in combination with a tumor necrosis factor (TNF) inhibitor.

72. The method of claim 71, wherein the TNF inhibitor is adalimumab (Humira®), etanercept (Enbrel®), or infliximab (Remicade®).

73. The method of claim 61, wherein the human is an anti-TNF-inadequate responder.

74. The method of claim 61, wherein administration is in combination with a non-steroidal anti-inflammatory agent (NSAID), a corticosteroid, or a disease modifying antirheumatic drug (DMARD).

75. The method of claim 61, wherein administration is in combination with methotrexate.

76. The method of claim 74, wherein the human is a DMARD-inadequate responder.

77. The isolated polypeptide of claim 29, wherein the polypeptide comprises the amino acid sequence set forth in SEQ ID NO:5.

* * * * *

UNITED STATES PATENT AND TRADEMARK OFFICE
CERTIFICATE OF CORRECTION

PATENT NO.       : 8,338,376 B2
APPLICATION NO.  : 12/560257
DATED            : December 25, 2012
INVENTOR(S)      : Evan Beckman et al.

Page 1 of 1

It is certified that error appears in the above-identified patent and that said Letters Patent is hereby corrected as shown below:

In the Claims:

At column 74, claim number 19, line number 63, "SEQ ID NO:2" should read --SEQ ID NO: 21--

At column 75, claim number 20, line number 2, "the extracellular domain of LT-β-R set forth in SEQ ID NO:4" should read --the extracellular domain of LT-β-R set forth in SEQ ID NO:4 or SEQ ID NO:23--

At column 75, claim number 23, line number 22, "variant LT-β-R extracellular domain as set forth the amino" should read --variant LT-β-R extracellular domain as set forth in_the amino--

At column 75, claim number 32, line number 58, "forth in SEQ ID NO:23 SEQ ID NO:4 or in a mammalian cell" should read --forth in SEQ ID NO:23 or SEQ ID NO:4 in a mammalian cell--

At column 78, claim number 76, line number 30, "The method of claim 74" should read --The method of claim 61--

Signed and Sealed this
Twentieth Day of August, 2013

Teresa Stanek Rea
*Acting Director of the United States Patent and Trademark Office*

SEQUENCE LISTING

<160> NUMBER OF SEQ ID NOS: 28

<210> SEQ ID NO 1
<211> LENGTH: 435
<212> TYPE: PRT
<213> ORGANISM: Homo sapiens -continued
<220> FEATURE:
<221> NAME/KEY: misc_feature
<223> OTHER INFORMATION: Full length human wild type LTBR amino acid
      sequence (immature form) corresponding to GenPept ID No. P36941

<400> SEQUENCE: 1

```
Met Leu Leu Pro Trp Ala Thr Ser Ala Pro Gly Leu Ala Trp Gly Pro
1               5                   10                  15

Leu Val Leu Gly Leu Phe Gly Leu Leu Ala Ala Ser Gln Pro Gln Ala
            20                  25                  30

Val Pro Pro Tyr Ala Ser Glu Asn Gln Thr Cys Arg Asp Gln Glu Lys
        35                  40                  45

Glu Tyr Tyr Glu Pro Gln His Arg Ile Cys Cys Ser Arg Cys Pro Pro
    50                  55                  60

Gly Thr Tyr Val Ser Ala Lys Cys Ser Arg Ile Arg Asp Thr Val Cys
65                  70                  75                  80

Ala Thr Cys Ala Glu Asn Ser Tyr Asn Glu His Trp Asn Tyr Leu Thr
                85                  90                  95

Ile Cys Gln Leu Cys Arg Pro Cys Asp Pro Val Met Gly Leu Glu Glu
            100                 105                 110

Ile Ala Pro Cys Thr Ser Lys Arg Lys Thr Gln Cys Arg Cys Gln Pro
        115                 120                 125

Gly Met Phe Cys Ala Ala Trp Ala Leu Glu Cys Thr His Cys Glu Leu
    130                 135                 140

Leu Ser Asp Cys Pro Pro Gly Thr Glu Ala Glu Leu Lys Asp Glu Val
145                 150                 155                 160

Gly Lys Gly Asn Asn His Cys Val Pro Cys Lys Ala Gly His Phe Gln
                165                 170                 175

Asn Thr Ser Ser Pro Ser Ala Arg Cys Gln Pro His Thr Arg Cys Glu
            180                 185                 190

Asn Gln Gly Leu Val Glu Ala Ala Pro Gly Thr Ala Gln Ser Asp Thr
        195                 200                 205

Thr Cys Lys Asn Pro Leu Glu Pro Leu Pro Pro Glu Met Ser Gly Thr
    210                 215                 220

Met Leu Met Leu Ala Val Leu Leu Pro Leu Ala Phe Phe Leu Leu Leu
225                 230                 235                 240

Ala Thr Val Phe Ser Cys Ile Trp Lys Ser His Pro Ser Leu Cys Arg
                245                 250                 255

Lys Leu Gly Ser Leu Leu Lys Arg Arg Pro Gln Gly Glu Gly Pro Asn
            260                 265                 270

Pro Val Ala Gly Ser Trp Glu Pro Pro Lys Ala His Pro Tyr Phe Pro
        275                 280                 285

Asp Leu Val Gln Pro Leu Leu Pro Ile Ser Gly Asp Val Ser Pro Val
    290                 295                 300

Ser Thr Gly Leu Pro Ala Ala Pro Val Leu Glu Ala Gly Val Pro Gln
305                 310                 315                 320

Gln Gln Ser Pro Leu Asp Leu Thr Arg Glu Pro Gln Leu Glu Pro Gly
                325                 330                 335

Glu Gln Ser Gln Val Ala His Gly Thr Asn Gly Ile His Val Thr Gly
            340                 345                 350

Gly Ser Met Thr Ile Thr Gly Asn Ile Tyr Ile Tyr Asn Gly Pro Val
        355                 360                 365

Leu Gly Gly Pro Pro Gly Pro Gly Asp Leu Pro Ala Thr Pro Glu Pro
    370                 375                 380
```

```
Pro Tyr Pro Ile Pro Glu Glu Gly Asp Pro Gly Pro Pro Gly Leu Ser
385                 390                 395                 400

Thr Pro His Gln Glu Asp Gly Lys Ala Trp His Leu Ala Glu Thr Glu
                405                 410                 415

His Cys Gly Ala Thr Pro Ser Asn Arg Gly Pro Arg Asn Gln Phe Ile
            420                 425                 430

Thr His Asp
        435

<210> SEQ ID NO 2
<211> LENGTH: 227
<212> TYPE: PRT
<213> ORGANISM: Artificial Sequence
<220> FEATURE:
<223> OTHER INFORMATION: Chemically synthesized Fc portion of LTBR06,
      including valine mutation

<400> SEQUENCE: 2

Val Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225

<210> SEQ ID NO 3
<211> LENGTH: 663
<212> TYPE: DNA
<213> ORGANISM: Artificial Sequence
<220> FEATURE:
<223> OTHER INFORMATION: Chemically synthesized extracellular domain of
      LTBR06
```

-continued

<400> SEQUENCE: 3

```
atgctcctgc cttgggccac ctctgccccc ggcctggcct gggggcctct ggtgctgggc      60
ctcttcgggc tcctggcagc agcggtgcct ccatatgcgt cggagaacca gacctgcagg     120
gaccaggaaa aggaatacta tgagccccag caccgcatct gctgctcccg ctgcccgcca     180
ggcacctatg tctcagctaa atgtagccgc atccgggaca cagtttgtgc cacatgtgcc     240
gagaattcct acaacgagca ctggaactac ctgaccatct gccagctgtg ccgcccctgt     300
gacccagtga tgggcctcga ggagattgcc cctgcacaa gcaaacggaa gacccagtgc      360
cgctgccagc cgggaatgtt ctgtgctgcc tgggccctcg agtgtacaca ctgcgagcta     420
ctttctgact gcccgcctgg cactgaagcc gagctcaaag atgaagttgg aagggtaac     480
aaccactgcg tccctgcaa ggcagggcac ttccagaata cctcctcccc cagcgcccgc      540
tgccagcccc acaccaggtg tgagaaccaa ggtctggtgg aggcagctcc aggcactgcc     600
cagtccgaca acctgcaa aaatccatta gagccactgc ccagagat gtcaggaacc        660
atg                                                                   663
```

<210> SEQ ID NO 4
<211> LENGTH: 194
<212> TYPE: PRT
<213> ORGANISM: Artificial Sequence
<220> FEATURE:
<223> OTHER INFORMATION: Chemically synthesized extracellular domain of LTBR06

<400> SEQUENCE: 4

```
Ala Val Pro Pro Tyr Ala Ser Glu Asn Gln Thr Cys Arg Asp Gln Glu
1               5                   10                  15
Lys Glu Tyr Tyr Glu Pro Gln His Arg Ile Cys Cys Ser Arg Cys Pro
            20                  25                  30
Pro Gly Thr Tyr Val Ser Ala Lys Cys Ser Arg Ile Arg Asp Thr Val
        35                  40                  45
Cys Ala Thr Cys Ala Glu Asn Ser Tyr Asn Glu His Trp Asn Tyr Leu
    50                  55                  60
Thr Ile Cys Gln Leu Cys Arg Pro Cys Asp Pro Val Met Gly Leu Glu
65                  70                  75                  80
Glu Ile Ala Pro Cys Thr Ser Arg Lys Thr Gln Cys Arg Cys Gln
                85                  90                  95
Pro Gly Met Phe Cys Ala Ala Trp Ala Leu Glu Cys Thr His Cys Glu
            100                 105                 110
Leu Leu Ser Asp Cys Pro Pro Gly Thr Glu Ala Glu Leu Lys Asp Glu
        115                 120                 125
Val Gly Lys Gly Asn Asn His Cys Val Pro Cys Lys Ala Gly His Phe
    130                 135                 140
Gln Asn Thr Ser Ser Pro Ser Ala Arg Cys Gln Pro His Thr Arg Cys
145                 150                 155                 160
Glu Asn Gln Gly Leu Val Glu Ala Ala Pro Gly Thr Ala Gln Ser Asp
                165                 170                 175
Thr Thr Cys Lys Asn Pro Leu Glu Pro Leu Pro Glu Met Ser Gly
            180                 185                 190
Thr Met
```

<210> SEQ ID NO 5
<211> LENGTH: 421
<212> TYPE: PRT
<213> ORGANISM: Artificial Sequence
<220> FEATURE:
<223> OTHER INFORMATION: Chemically synthesized amino acid sequence of the mature form of LTBR06

<400> SEQUENCE: 5

```
Ala Val Pro Pro Tyr Ala Ser Glu Asn Gln Thr Cys Arg Asp Gln Glu
1               5                   10                  15

Lys Glu Tyr Tyr Glu Pro Gln His Arg Ile Cys Cys Ser Arg Cys Pro
            20                  25                  30

Pro Gly Thr Tyr Val Ser Ala Lys Cys Ser Arg Ile Arg Asp Thr Val
        35                  40                  45

Cys Ala Thr Cys Ala Glu Asn Ser Tyr Asn Glu His Trp Asn Tyr Leu
50                  55                  60

Thr Ile Cys Gln Leu Cys Arg Pro Cys Asp Pro Val Met Gly Leu Glu
65                  70                  75                  80

Glu Ile Ala Pro Cys Thr Ser Lys Arg Lys Thr Gln Cys Arg Cys Gln
                85                  90                  95

Pro Gly Met Phe Cys Ala Ala Trp Ala Leu Glu Cys Thr His Cys Glu
            100                 105                 110

Leu Leu Ser Asp Cys Pro Pro Gly Thr Glu Ala Glu Leu Lys Asp Glu
        115                 120                 125

Val Gly Lys Gly Asn Asn His Cys Val Pro Cys Lys Ala Gly His Phe
130                 135                 140

Gln Asn Thr Ser Ser Pro Ser Ala Arg Cys Gln Pro His Thr Arg Cys
145                 150                 155                 160

Glu Asn Gln Gly Leu Val Glu Ala Ala Pro Gly Thr Ala Gln Ser Asp
                165                 170                 175

Thr Thr Cys Lys Asn Pro Leu Glu Pro Leu Pro Pro Glu Met Ser Gly
            180                 185                 190

Thr Met Val Asp Lys Thr His Thr Cys Pro Pro Cys Pro Ala Pro Glu
        195                 200                 205

Leu Leu Gly Gly Pro Ser Val Phe Leu Phe Pro Pro Lys Pro Lys Asp
210                 215                 220

Thr Leu Met Ile Ser Arg Thr Pro Glu Val Thr Cys Val Val Val Asp
225                 230                 235                 240

Val Ser His Glu Asp Pro Glu Val Lys Phe Asn Trp Tyr Val Asp Gly
                245                 250                 255

Val Glu Val His Asn Ala Lys Thr Lys Pro Arg Glu Glu Gln Tyr Asn
            260                 265                 270

Ser Thr Tyr Arg Val Val Ser Val Leu Thr Val Leu His Gln Asp Trp
        275                 280                 285

Leu Asn Gly Lys Glu Tyr Lys Cys Lys Val Ser Asn Lys Ala Leu Pro
290                 295                 300

Ala Pro Ile Glu Lys Thr Ile Ser Lys Ala Lys Gly Gln Pro Arg Glu
305                 310                 315                 320

Pro Gln Val Tyr Thr Leu Pro Pro Ser Arg Asp Glu Leu Thr Lys Asn
                325                 330                 335

Gln Val Ser Leu Thr Cys Leu Val Lys Gly Phe Tyr Pro Ser Asp Ile
            340                 345                 350

Ala Val Glu Trp Glu Ser Asn Gly Gln Pro Glu Asn Asn Tyr Lys Thr
        355                 360                 365

Thr Pro Pro Val Leu Asp Ser Asp Gly Ser Phe Phe Leu Tyr Ser Lys
    370                 375                 380

Leu Thr Val Asp Lys Ser Arg Trp Gln Gln Gly Asn Val Phe Ser Cys
385                 390                 395                 400
```

```
Ser Val Met His Glu Ala Leu His Asn His Tyr Thr Gln Lys Ser Leu
            405                 410                 415

Ser Leu Ser Pro Gly
            420

<210> SEQ ID NO 6
<211> LENGTH: 453
<212> TYPE: PRT
<213> ORGANISM: Artificial Sequence
<220> FEATURE:
<223> OTHER INFORMATION: Chemically synthesized wild type LTBR-Ig fusion
      protein

<400> SEQUENCE: 6

Met Leu Leu Pro Trp Ala Thr Ser Ala Pro Gly Leu Ala Trp Gly Pro
1               5                   10                  15

Leu Val Leu Gly Leu Phe Gly Leu Leu Ala Ala Ser Gln Pro Gln Ala
            20                  25                  30

Val Pro Pro Tyr Ala Ser Glu Asn Gln Thr Cys Arg Asp Gln Glu Lys
        35                  40                  45

Glu Tyr Tyr Glu Pro Gln His Arg Ile Cys Cys Ser Arg Cys Pro Pro
    50                  55                  60

Gly Thr Tyr Val Ser Ala Lys Cys Ser Arg Ile Arg Asp Thr Val Cys
65                  70                  75                  80

Ala Thr Cys Ala Glu Asn Ser Tyr Asn Glu His Trp Asn Tyr Leu Thr
                85                  90                  95

Ile Cys Gln Leu Cys Arg Pro Cys Asp Pro Val Met Gly Leu Glu Glu
            100                 105                 110

Ile Ala Pro Cys Thr Ser Lys Arg Lys Thr Gln Cys Arg Cys Gln Pro
        115                 120                 125

Gly Met Phe Cys Ala Ala Trp Ala Leu Glu Cys Thr His Cys Glu Leu
    130                 135                 140

Leu Ser Asp Cys Pro Pro Gly Thr Glu Ala Glu Leu Lys Asp Glu Val
145                 150                 155                 160

Gly Lys Gly Asn Asn His Cys Val Pro Cys Lys Ala Gly His Phe Gln
                165                 170                 175

Asn Thr Ser Ser Pro Ser Ala Arg Cys Gln Pro His Thr Arg Cys Glu
            180                 185                 190

Asn Gln Gly Leu Val Glu Ala Ala Pro Gly Thr Ala Gln Ser Asp Thr
        195                 200                 205

Thr Cys Lys Asn Pro Leu Glu Pro Leu Pro Pro Glu Met Ser Gly Thr
    210                 215                 220

Met Val Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
435                 440                 445

Leu Ser Pro Gly Lys
    450

<210> SEQ ID NO 7
<211> LENGTH: 1344
<212> TYPE: DNA
<213> ORGANISM: Artificial Sequence
<220> FEATURE:
<223> OTHER INFORMATION: Chemically synthesized LTBR06

<400> SEQUENCE: 7
atgctcctgc cttgggccac ctctgccccc ggcctggcct ggggccctct ggtgctgggc      60
ctcttcgggc tcctggcagc agcggtgcct ccatatgcgt cggagaacca gacctgcagg     120
gaccaggaaa aggaatacta tgagcccag caccgcatct gctgctcccg ctgcccgcca     180
ggcacctatg tctcagctaa atgtagccgc atccgggaca cagtttgtgc acatgtgcc     240 gagaattcct acaacgagca ctggaactac ctgaccatct gccagctgtg ccgcccctgt     300
gacccagtga tgggcctcga ggagattgcc cctgcacaa gcaaacggaa gacccagtgc     360
cgctgccagc cgggaatgtt ctgtgctgcc tgggccctcg agtgtacaca ctgcgagcta     420
ctttctgact gcccgcctgg cactgaagcc gagctcaaag atgaagttgg aagggtaac     480 aaccactgcg tccctgcaa ggcagggcac ttccagaata cctcctcccc cagcgcccgc     540
tgccagcccc acaccaggtg tgagaaccaa ggtctggtgg aggcagctcc aggcactgcc     600
cagtccgaca caacctgcaa aaatccatta gagccactgc ccccagagat gtcaggaacc     660
atggtcgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagacctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc cccatcccg ggatgagctg     1080 accaagaacc aggtcagcct gacctgcctg gtcaaaggct tctatcccag cgacatcgcc    1140
gtggagtggg agagcaatgg gcagccggag aacaactaca gaccacgcc tcccgtgttg    1200 gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggt                                           1344
```

<210> SEQ ID NO 8
<211> LENGTH: 448
<212> TYPE: PRT
<213> ORGANISM: Artificial Sequence
<220> FEATURE:
<223> OTHER INFORMATION: Chemically synthesized LTBR06 amino acid sequence, including signal sequence

<400> SEQUENCE: 8

```
Met Leu Leu Pro Trp Ala Thr Ser Ala Pro Gly Leu Ala Trp Gly Pro
1               5                   10                  15

Leu Val Leu Gly Leu Phe Gly Leu Leu Ala Ala Val Pro Pro Tyr
            20                  25                  30

Ala Ser Glu Asn Gln Thr Cys Arg Asp Gln Glu Lys Glu Tyr Tyr Glu
            35                  40                  45

Pro Gln His Arg Ile Cys Cys Ser Arg Cys Pro Pro Gly Thr Tyr Val
        50                  55                  60

Ser Ala Lys Cys Ser Arg Ile Arg Asp Thr Val Cys Ala Thr Cys Ala
65                  70                  75                  80

Glu Asn Ser Tyr Asn Glu His Trp Asn Tyr Leu Thr Ile Cys Gln Leu
                85                  90                  95

Cys Arg Pro Cys Asp Pro Val Met Gly Leu Glu Ile Ala Pro Cys
            100                 105                 110

Thr Ser Lys Arg Lys Thr Gln Cys Arg Cys Gln Pro Gly Met Phe Cys
        115                 120                 125

Ala Ala Trp Ala Leu Glu Cys Thr His Cys Glu Leu Leu Ser Asp Cys
130                 135                 140

Pro Pro Gly Thr Glu Ala Glu Leu Lys Asp Glu Val Gly Lys Gly Asn
145                 150                 155                 160

Asn His Cys Val Pro Cys Lys Ala Gly His Phe Gln Asn Thr Ser Ser
                165                 170                 175

Pro Ser Ala Arg Cys Gln Pro His Thr Arg Cys Glu Asn Gln Gly Leu
            180                 185                 190

Val Glu Ala Ala Pro Gly Thr Ala Gln Ser Asp Thr Thr Cys Lys Asn
        195                 200                 205

Pro Leu Glu Pro Leu Pro Pro Glu Met Ser Gly Thr Met Val Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 9
<211> LENGTH: 425
<212> TYPE: PRT
<213> ORGANISM: Artificial Sequence
<220> FEATURE:
<223> OTHER INFORMATION: Chemically synthesized LTBR05, mature form
      amino acid sequence

<400> SEQUENCE: 9

Ser Gln Pro Gln Ala Val Pro Pro Tyr Ala Ser Glu Asn Gln Thr Cys
1               5                   10                  15

Arg Asp Gln Glu Lys Glu Tyr Tyr Glu Pro Gln His Arg Ile Cys Cys
            20                  25                  30

Ser Arg Cys Pro Pro Gly Thr Tyr Val Ser Ala Lys Cys Ser Arg Ile
        35                  40                  45

Arg Asp Thr Val Cys Ala Thr Cys Ala Glu Asn Ser Tyr Asn Glu His
    50                  55                  60

Trp Asn Tyr Leu Thr Ile Cys Gln Leu Cys Arg Pro Cys Asp Pro Val
65                  70                  75                  80

Met Gly Leu Glu Glu Ile Ala Pro Cys Thr Ser Lys Arg Lys Thr Gln
                85                  90                  95

Cys Arg Cys Gln Pro Gly Met Phe Cys Ala Ala Trp Ala Leu Glu Cys
            100                 105                 110

Thr His Cys Glu Leu Leu Ser Asp Cys Pro Pro Gly Thr Glu Ala Glu
        115                 120                 125

Leu Lys Asp Glu Val Gly Lys Gly Asn Asn His Cys Val Pro Cys Lys
    130                 135                 140

Ala Gly His Phe Gln Asn Thr Ser Ser Pro Ser Ala Arg Cys Gln Pro
145                 150                 155                 160

His Thr Arg Cys Glu Asn Gln Gly Leu Val Glu Ala Ala Pro Gly Thr
                165                 170                 175

Ala Gln Ser Asp Thr Thr Cys Lys Asn Pro Leu Glu Pro Leu Pro Pro
            180                 185                 190

Glu Met Ser Gly Thr Met Val Asp Lys Thr His Thr Cys Pro Pro Cys
        195                 200                 205

Pro Ala Pro Glu Leu Leu Gly Gly Pro Ser Val Phe Leu Phe Pro Pro
    210                 215                 220

Lys Pro Lys Asp Thr Leu Met Ile Ser Arg Thr Pro Glu Val Thr Cys
225                 230                 235                 240

Val Val Val Asp Val Ser His Glu Asp Pro Glu Val Lys Phe Asn Trp
                245                 250                 255

Tyr Val Asp Gly Val Glu Val His Asn Ala Lys Thr Lys Pro Arg Glu
            260                 265                 270

Glu Gln Tyr Asn Ser Thr Tyr Arg Val Val Ser Val Leu Thr Val Leu
        275                 280                 285
```

-continued

```
His Gln Asp Trp Leu Asn Gly Lys Glu Tyr Lys Cys Lys Val Ser Asn
    290                 295                 300

Lys Ala Leu Pro Ala Pro Ile Glu Lys Thr Ile Ser Lys Ala Lys Gly
305                 310                 315                 320

Gln Pro Arg Glu Pro Gln Val Tyr Thr Leu Pro Pro Ser Arg Asp Glu
                325                 330                 335

Leu Thr Lys Asn Gln Val Ser Leu Thr Cys Leu Val Lys Gly Phe Tyr
            340                 345                 350

Pro Ser Asp Ile Ala Val Glu Trp Glu Ser Asn Gly Gln Pro Glu Asn
        355                 360                 365

Asn Tyr Lys Thr Thr Pro Pro Val Leu Asp Ser Asp Gly Ser Phe Phe
    370                 375                 380

Leu Tyr Ser Lys Leu Thr Val Asp Lys Ser Arg Trp Gln Gln Gly Asn
385                 390                 395                 400

Val Phe Ser Cys Ser Val Met His Glu Ala Leu His Asn His Tyr Thr
                405                 410                 415

Gln Lys Ser Leu Ser Leu Ser Pro Gly
            420                 425

<210> SEQ ID NO 10
<211> LENGTH: 421
<212> TYPE: PRT
<213> ORGANISM: Artificial Sequence
<220> FEATURE:
<223> OTHER INFORMATION: Chemically synthesized non-glycosylated
      LTBR-IgG

<400> SEQUENCE: 10

Ala Val Pro Pro Tyr Ala Ser Glu Gln Gln Thr Cys Arg Asp Gln Glu
1               5                   10                  15

Lys Glu Tyr Tyr Glu Pro Gln His Arg Ile Cys Cys Ser Arg Cys Pro
                20                  25                  30

Pro Gly Thr Tyr Val Ser Ala Lys Cys Ser Arg Ile Arg Asp Thr Val
            35                  40                  45

Cys Ala Thr Cys Ala Glu Asn Ser Tyr Asn Glu His Trp Asn Tyr Leu
50                  55                  60

Thr Ile Cys Gln Leu Cys Arg Pro Cys Asp Pro Val Met Gly Leu Glu
65                  70                  75                  80

Glu Ile Ala Pro Cys Thr Ser Lys Arg Lys Thr Gln Cys Arg Cys Gln
                85                  90                  95

Pro Gly Met Phe Cys Ala Ala Trp Ala Leu Glu Cys Thr His Cys Glu
            100                 105                 110

Leu Leu Ser Asp Cys Pro Pro Gly Thr Glu Ala Glu Leu Lys Asp Glu
        115                 120                 125

Val Gly Lys Gly Asn Asn His Cys Val Pro Cys Lys Ala Gly His Phe
    130                 135                 140

Gln Gln Thr Ser Ser Pro Ser Ala Arg Cys Gln Pro His Thr Arg Cys
145                 150                 155                 160

Glu Asn Gln Gly Leu Val Glu Ala Ala Pro Gly Thr Ala Gln Ser Asp
                165                 170                 175

Thr Thr Cys Lys Asn Pro Leu Glu Pro Leu Pro Pro Glu Met Ser Gly
            180                 185                 190

Thr Met Val Asp Lys Thr His Thr Cys Pro Pro Cys Pro Ala Pro Glu
        195                 200                 205

Leu Leu Gly Gly Pro Ser Val Phe Leu Phe Pro Pro Lys Pro Lys Asp
    210                 215                 220
```

```
Thr Leu Met Ile Ser Arg Thr Pro Glu Val Thr Cys Val Val Asp
225                 230                 235                 240

Val Ser His Glu Asp Pro Glu Val Lys Phe Asn Trp Tyr Val Asp Gly
                245                 250                 255

Val Glu Val His Asn Ala Lys Thr Lys Pro Arg Glu Glu Gln Tyr Asn
            260                 265                 270

Ser Thr Tyr Arg Val Val Ser Val Leu Thr Val Leu His Gln Asp Trp
        275                 280                 285

Leu Asn Gly Lys Glu Tyr Lys Cys Lys Val Ser Asn Lys Ala Leu Pro
    290                 295                 300

Ala Pro Ile Glu Lys Thr Ile Ser Lys Ala Lys Gly Gln Pro Arg Glu
305                 310                 315                 320

Pro Gln Val Tyr Thr Leu Pro Pro Ser Arg Asp Glu Leu Thr Lys Asn
                325                 330                 335

Gln Val Ser Leu Thr Cys Leu Val Lys Gly Phe Tyr Pro Ser Asp Ile
            340                 345                 350

Ala Val Glu Trp Glu Ser Asn Gly Gln Pro Glu Asn Asn Tyr Lys Thr
        355                 360                 365

Thr Pro Pro Val Leu Asp Ser Asp Gly Ser Phe Phe Leu Tyr Ser Lys
    370                 375                 380

Leu Thr Val Asp Lys Ser Arg Trp Gln Gln Gly Asn Val Phe Ser Cys
385                 390                 395                 400

Ser Val Met His Glu Ala Leu His Asn His Tyr Thr Gln Lys Ser Leu
                405                 410                 415

Ser Leu Ser Pro Gly
            420

<210> SEQ ID NO 11
<211> LENGTH: 426
<212> TYPE: PRT
<213> ORGANISM: Artificial Sequence
<220> FEATURE:
<223> OTHER INFORMATION: Chemically synthesized LTBR01, mature form
      amino acid sequence

<400> SEQUENCE: 11

Ser Gln Pro Gln Ala Val Pro Pro Tyr Ala Ser Glu Asn Gln Thr Cys
1               5                   10                  15

Arg Asp Gln Glu Lys Glu Tyr Tyr Glu Pro Gln His Arg Ile Cys Cys
                20                  25                  30

Ser Arg Cys Pro Pro Gly Thr Tyr Val Ser Ala Lys Cys Ser Arg Ile
            35                  40                  45

Arg Asp Thr Val Cys Ala Thr Cys Ala Glu Asn Ser Tyr Asn Glu His
        50                  55                  60

Trp Asn Tyr Leu Thr Ile Cys Gln Leu Cys Arg Pro Cys Asp Pro Val
65                  70                  75                  80

Met Gly Leu Glu Glu Ile Ala Pro Cys Thr Ser Lys Arg Lys Thr Gln
                85                  90                  95

Cys Arg Cys Gln Pro Gly Met Phe Cys Ala Ala Trp Ala Leu Glu Cys
            100                 105                 110

Thr His Cys Glu Leu Leu Ser Asp Cys Pro Pro Gly Thr Glu Ala Glu
        115                 120                 125

Leu Lys Asp Glu Val Gly Lys Gly Asn Asn His Cys Val Pro Cys Lys
130                 135                 140

Ala Gly His Phe Gln Asn Thr Ser Ser Pro Ser Ala Arg Cys Gln Pro
145                 150                 155                 160
```

His Thr Arg Cys Glu Asn Gln Gly Leu Val Glu Ala Ala Pro Gly Thr
165                 170                 175

Ala Gln Ser Asp Thr Thr Cys Lys Asn Pro Leu Glu Pro Leu Pro Pro
        180                 185                 190

Glu Met Ser Gly Thr Met Val Asp Lys Thr His Thr Cys Pro Pro Cys
            195                 200                 205

Pro Ala Pro Glu Leu Leu Gly Gly Pro Ser Val Phe Leu Phe Pro Pro
        210                 215                 220

Lys Pro Lys Asp Thr Leu Met Ile Ser Arg Thr Pro Glu Val Thr Cys
225                 230                 235                 240

Val Val Val Asp Val Ser His Glu Asp Pro Glu Val Lys Phe Asn Trp
                245                 250                 255

Tyr Val Asp Gly Val Glu Val His Asn Ala Lys Thr Lys Pro Arg Glu
            260                 265                 270

Glu Gln Tyr Asn Ser Thr Tyr Arg Val Val Ser Val Leu Thr Val Leu
        275                 280                 285

His Gln Asp Trp Leu Asn Gly Lys Glu Tyr Lys Cys Lys Val Ser Asn
    290                 295                 300

Lys Ala Leu Pro Ala Pro Ile Glu Lys Thr Ile Ser Lys Ala Lys Gly
305                 310                 315                 320

Gln Pro Arg Glu Pro Gln Val Tyr Thr Leu Pro Pro Ser Arg Asp Glu
                325                 330                 335

Leu Thr Lys Asn Gln Val Ser Leu Thr Cys Leu Val Lys Gly Phe Tyr
            340                 345                 350

Pro Ser Asp Ile Ala Val Glu Trp Glu Ser Asn Gly Gln Pro Glu Asn
        355                 360                 365

Asn Tyr Lys Thr Thr Pro Pro Val Leu Asp Ser Asp Gly Ser Phe Phe
    370                 375                 380

Leu Tyr Ser Lys Leu Thr Val Asp Lys Ser Arg Trp Gln Gln Gly Asn
385                 390                 395                 400

Val Phe Ser Cys Ser Val Met His Glu Ala Leu His Asn His Tyr Thr
                405                 410                 415

Gln Lys Ser Leu Ser Leu Ser Pro Gly Lys
            420                 425

<210> SEQ ID NO 12
<211> LENGTH: 421
<212> TYPE: PRT
<213> ORGANISM: Artificial Sequence
<220> FEATURE:
<223> OTHER INFORMATION: Chemically synthesized LTBR09, mature form
      amino acid sequence

<400> SEQUENCE: 12

Ala Val Pro Pro Tyr Ala Ser Glu Asn Gln Thr Cys Arg Asp Gln Glu
1               5                   10                  15

Lys Glu Tyr Tyr Glu Pro Gln His Arg Ile Cys Cys Ser Arg Cys Pro
            20                  25                  30

Pro Gly Thr Tyr Val Ser Ala Lys Cys Ser Arg Ile Arg Asp Thr Val
        35                  40                  45

Cys Ala Thr Cys Ala Glu Asn Ser Tyr Asn Glu His Trp Asn Tyr Leu
    50                  55                  60

Thr Ile Cys Gln Leu Cys Arg Pro Cys Asp Pro Val Met Gly Leu Glu
65                  70                  75                  80

Glu Ile Ala Pro Cys Thr Ser Lys Arg Lys Thr Gln Cys Arg Cys Gln
                85                  90                  95

Pro Gly Met Phe Cys Ala Ala Trp Ala Leu Glu Cys Thr His Cys Glu
             100                 105                 110

Leu Leu Ser Asp Cys Pro Pro Gly Thr Glu Ala Glu Leu Lys Asp Glu
             115                 120                 125

Val Gly Lys Gly Asn Asn His Cys Val Pro Cys Lys Ala Gly His Phe
        130                 135                 140

Gln Asn Thr Ser Ser Pro Ser Ala Arg Cys Gln Pro His Thr Arg Cys
145                 150                 155                 160

Glu Asn Gln Gly Leu Val Glu Ala Ala Pro Gly Thr Ala Gln Ser Asp
                165                 170                 175

Thr Thr Cys Lys Asn Pro Leu Glu Pro Leu Pro Pro Glu Met Ser Gly
            180                 185                 190

Thr Met Val Asp Lys Thr His Thr Cys Pro Pro Cys Pro Ala Pro Glu
        195                 200                 205

Leu Leu Gly Gly Pro Ser Val Phe Leu Phe Pro Pro Lys Pro Lys Asp
210                 215                 220

Thr Leu Met Ile Ser Arg Thr Pro Glu Val Thr Cys Val Val Val Asp
225                 230                 235                 240

Val Ser His Glu Asp Pro Glu Val Lys Phe Asn Trp Tyr Val Asp Gly
                245                 250                 255

Val Glu Val His Asn Ala Lys Thr Lys Pro Arg Glu Glu Gln Tyr Gln
            260                 265                 270

Ser Thr Tyr Arg Val Val Ser Val Leu Thr Val Leu His Gln Asp Trp
        275                 280                 285

Leu Asn Gly Lys Glu Tyr Lys Cys Lys Val Ser Asn Lys Ala Leu Pro
290                 295                 300

Ala Pro Ile Glu Lys Thr Ile Ser Lys Ala Lys Gly Gln Pro Arg Glu
305                 310                 315                 320

Pro Gln Val Tyr Thr Leu Pro Pro Ser Arg Asp Glu Leu Thr Lys Asn
                325                 330                 335

Gln Val Ser Leu Thr Cys Leu Val Lys Gly Phe Tyr Pro Ser Asp Ile
            340                 345                 350

Ala Val Glu Trp Glu Ser Asn Gly Gln Pro Glu Asn Asn Tyr Lys Thr
        355                 360                 365

Thr Pro Pro Val Leu Asp Ser Asp Gly Ser Phe Phe Leu Tyr Ser Lys
        370                 375                 380

Leu Thr Val Asp Lys Ser Arg Trp Gln Gln Gly Asn Val Phe Ser Cys
385                 390                 395                 400

Ser Val Met His Glu Ala Leu His Asn His Tyr Thr Gln Lys Ser Leu
                405                 410                 415

Ser Leu Ser Pro Gly
            420

<210> SEQ ID NO 13
<211> LENGTH: 13
<212> TYPE: PRT
<213> ORGANISM: Artificial Sequence
<220> FEATURE:
<223> OTHER INFORMATION: Chemically synthesized LTBR06 hinge sequence

<400> SEQUENCE: 13

Val Asp Lys Thr His Thr Cys Pro Pro Cys Pro Ala Pro
1               5                   10

```
<210> SEQ ID NO 14
<211> LENGTH: 13
<212> TYPE: PRT
<213> ORGANISM: Artificial Sequence
<220> FEATURE:
<223> OTHER INFORMATION: Chemically synthesized Hinge 2211 (D169N)
      sequence

<400> SEQUENCE: 14

Val Asn Lys Thr His Thr Cys Pro Pro Cys Pro Ala Pro
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Chemically synthesized Hinge 2212 (T198N)
      sequence

<400> SEQUENCE: 15

Val Asp Lys Asn His Thr Cys Pro Pro Cys Pro Ala Pro
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Chemically synthesized Hinge 2221 (valine
      deletion) sequence

<400> SEQUENCE: 16

Asp Lys Thr His Thr Cys Pro Pro Cys Pro Ala Pro
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Chemically synthesized Hinge 2217 (full length)
      sequence

<400> SEQUENCE: 17

Glu Pro Lys Ser Cys Asp Lys Thr His Thr Cys Pro Pro Cys Pro Ala
1               5                   10                  15

Pro

<210> SEQ ID NO 18
<211> LENGTH: 14
<212> TYPE: PRT
<213> ORGANISM: Artificial Sequence
<220> FEATURE:
<223> OTHER INFORMATION: Chemically synthesized Hinge 2219 (G4-hinge-
      G4Fc) sequence

<400> SEQUENCE: 18

Glu Ser Lys Tyr Gly Pro Pro Cys Pro Pro Cys Pro Ala Pro
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Chemically synthesized Hinge 2218 (G2-hinge-
      G2Fc) sequence
```

```
<400> SEQUENCE: 19

Cys Cys Val Glu Cys Pro Pro Cys Pro Ala Pro Val Ala Gly Pro
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: Chemically synthesized Hinge 2220 (short
      hinge - G1Fc) sequence

<400> SEQUENCE: 20

Cys Pro Pro Cys Pro Ala Pro
1               5

<210> SEQ ID NO 21
<211> LENGTH: 225
<212> TYPE: PRT
<213> ORGANISM: Homo sapiens
<220> FEATURE:
<221> NAME/KEY: misc_feature
<223> OTHER INFORMATION: Extracellular domain of human wild type LTBR
      amino acid sequence (immature form) corresponding to GenPept ID
      No. P36941

<400> SEQUENCE: 21

Met Leu Leu Pro Trp Ala Thr Ser Ala Pro Gly Leu Ala Trp Gly Pro
1               5                   10                  15

Leu Val Leu Gly Leu Phe Gly Leu Leu Ala Ala Ser Gln Pro Gln Ala
                20                  25                  30

Val Pro Pro Tyr Ala Ser Glu Asn Gln Thr Cys Arg Asp Gln Glu Lys
            35                  40                  45

Glu Tyr Tyr Glu Pro Gln His Arg Ile Cys Cys Ser Arg Cys Pro Pro
        50                  55                  60

Gly Thr Tyr Val Ser Ala Lys Cys Ser Arg Ile Arg Asp Thr Val Cys
65                  70                  75                  80

Ala Thr Cys Ala Glu Asn Ser Tyr Asn Glu His Trp Asn Tyr Leu Thr
                85                  90                  95

Ile Cys Gln Leu Cys Arg Pro Cys Asp Pro Val Met Gly Leu Glu Glu
            100                 105                 110

Ile Ala Pro Cys Thr Ser Lys Arg Lys Thr Gln Cys Arg Cys Gln Pro
        115                 120                 125

Gly Met Phe Cys Ala Ala Trp Ala Leu Glu Cys Thr His Cys Glu Leu
130                 135                 140

Leu Ser Asp Cys Pro Pro Gly Thr Glu Ala Glu Leu Lys Asp Glu Val
145                 150                 155                 160

Gly Lys Gly Asn Asn His Cys Val Pro Cys Lys Ala Gly His Phe Gln
                165                 170                 175

Asn Thr Ser Ser Pro Ser Ala Arg Cys Gln Pro His Thr Arg Cys Glu
            180                 185                 190

Asn Gln Gly Leu Val Glu Ala Ala Pro Gly Thr Ala Gln Ser Asp Thr
        195                 200                 205

Thr Cys Lys Asn Pro Leu Glu Pro Leu Pro Pro Glu Met Ser Gly Thr
    210                 215                 220

Met
225
```

<210> SEQ ID NO 22
<211> LENGTH: 227
<212> TYPE: PRT
<213> ORGANISM: Homo Sapiens
<220> FEATURE:
<221> NAME/KEY: misc_feature
<223> OTHER INFORMATION: Human Ig (Fc) domain

<400> SEQUENCE: 22

Cys Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225

<210> SEQ ID NO 23
<211> LENGTH: 193
<212> TYPE: PRT
<213> ORGANISM: Artificial Sequence
<220> FEATURE:
<223> OTHER INFORMATION: Chemically synthesized N-5 extracellular domain
      of LTBR06

<400> SEQUENCE: 23

Val Pro Pro Tyr Ala Ser Glu Asn Gln Thr Cys Arg Asp Gln Glu Lys
1               5                   10                  15

Glu Tyr Tyr Glu Pro Gln His Arg Ile Cys Cys Ser Arg Cys Pro Pro
            20                  25                  30

Gly Thr Tyr Val Ser Ala Lys Cys Ser Arg Ile Arg Asp Thr Val Cys
        35                  40                  45

Ala Thr Cys Ala Glu Asn Ser Tyr Asn Glu His Trp Asn Tyr Leu Thr
    50                  55                  60

Ile Cys Gln Leu Cys Arg Pro Cys Asp Pro Val Met Gly Leu Glu Glu
65                  70                  75                  80

```
Ile Ala Pro Cys Thr Ser Lys Arg Lys Thr Gln Cys Arg Cys Gln Pro
                85                  90                  95

Gly Met Phe Cys Ala Ala Trp Ala Leu Glu Cys Thr His Cys Glu Leu
            100                 105                 110

Leu Ser Asp Cys Pro Pro Gly Thr Glu Ala Glu Leu Lys Asp Glu Val
        115                 120                 125

Gly Lys Gly Asn Asn His Cys Val Pro Cys Lys Ala Gly His Phe Gln
    130                 135                 140

Asn Thr Ser Ser Pro Ser Ala Arg Cys Gln Pro His Thr Arg Cys Glu
145                 150                 155                 160

Asn Gln Gly Leu Val Glu Ala Ala Pro Gly Thr Ala Gln Ser Asp Thr
                165                 170                 175

Thr Cys Lys Asn Pro Leu Glu Pro Leu Pro Pro Glu Met Ser Gly Thr
            180                 185                 190

Met
```

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide

<400> SEQUENCE: 24

```
Ala Ala Gly Thr Tyr
1               5
```

<210> SEQ ID NO 25
<211> LENGTH: 4
<212> TYPE: PRT
<213> ORGANISM: Artificial Sequence
<220> FEATURE:
<223> OTHER INFORMATION: Synthetic peptide

<400> SEQUENCE: 25

```
Ala Gly Thr Tyr
1
```

<210> SEQ ID NO 26
<211> LENGTH: 4
<212> TYPE: PRT
<213> ORGANISM: Artificial Sequence
<220> FEATURE:
<223> OTHER INFORMATION: Synthetic peptide

<400> SEQUENCE: 26

```
Ser Gln Pro Gln
1
```

<210> SEQ ID NO 27
<211> LENGTH: 19
<212> TYPE: PRT
<213> ORGANISM: Artificial Sequence
<220> FEATURE:
<223> OTHER INFORMATION: Chemically synthesized IgG hinge peptide

<400> SEQUENCE: 27

```
Cys Asp Lys Thr His Thr Cys Pro Pro Cys Pro Ala Pro Glu Leu Leu
1               5                   10                  15

Gly Gly Pro
```

-continued

```
<210> SEQ ID NO 28
<211> LENGTH: 19
<212> TYPE: PRT
<213> ORGANISM: Artificial Sequence
<220> FEATURE:
<223> OTHER INFORMATION: Chemically synthesized hinge peptide

<400> SEQUENCE: 28

Val Asp Lys Thr His Thr Cys Pro Pro Cys Pro Ala Pro Glu Leu Leu
1               5                   10                  15

Gly Gly Pro
```